(12) United States Patent
Brasca et al.

(10) Patent No.: US 9,283,224 B2
(45) Date of Patent: Mar. 15, 2016

(54) SUBSTITUTED PYRIMIDINYL-PYRROLES ACTIVE AS KINASE INHIBITORS

(75) Inventors: Maria Gabriella Brasca, Nerviano (IT); Tiziano Bandiera, Gambolo (IT); Jay Aaron Bertrand, Didcot (GB); Paola Gnocchi, Stresa (IT); Danilo Mirizzi, Nerviano (IT); Marcella Nesi, Saronno (IT); Achille Panzeri, Merate (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 14/112,559

(22) PCT Filed: Apr. 5, 2012

(86) PCT No.: PCT/EP2012/056266
§ 371 (c)(1),
(2), (4) Date: Oct. 18, 2013

(87) PCT Pub. No.: WO2012/143248
PCT Pub. Date: Oct. 26, 2012

(65) Prior Publication Data
US 2014/0155421 A1  Jun. 5, 2014

(51) Int. Cl.
*A61K 31/506* (2006.01)
*C07D 403/04* (2006.01)
*C07D 405/14* (2006.01)
*C07F 5/02* (2006.01)

(52) U.S. Cl.
CPC ............ *A61K 31/506* (2013.01); *C07D 403/04* (2013.01); *C07D 405/14* (2013.01); *C07F 5/025* (2013.01)

(58) Field of Classification Search
CPC .. A61K 31/506; C07D 403/04; C07D 405/14; C07F 5/025
USPC ................................................ 544/331, 333
See application file for complete search history.

(56) References Cited

U.S. PATENT DOCUMENTS

| | | | | |
|---|---|---|---|---|
| 7,419,984 B2 * | 9/2008 | Bhatt et al. | ..................... | 514/275 |
| 8,263,604 B2 * | 9/2012 | Vanotti et al. | ................. | 514/275 |
| 8,399,668 B2 * | 3/2013 | D'Anello et al. | ............ | 544/331 |
| 8,592,583 B2 * | 11/2013 | D'Anello et al. | ............ | 544/331 |
| 8,658,662 B2 * | 2/2014 | Zampieri et al. | ............ | 514/275 |
| 2009/0099221 A1 * | 4/2009 | Vanotti et al. | ................. | 514/275 |
| 2012/0065192 A1 * | 3/2012 | Caldarelli et al. | ........... | 514/218 |
| 2012/0220771 A1 * | 8/2012 | D'Anello et al. | ............ | 544/331 |
| 2012/0245189 A1 * | 9/2012 | Zampieri et al. | ............ | 514/275 |
| 2014/0194406 A1 * | 7/2014 | Brasca et al. | ............ | 514/210.18 |

FOREIGN PATENT DOCUMENTS

| | | |
|---|---|---|
| WO | WO 2007/110344 A1 | 10/2007 |
| WO | WO 2007110344 A1 * | 10/2007 |
| WO | WO 2009/133170 A1 | 11/2009 |
| WO | WO 2009133170 A1 * | 11/2009 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
R.J. Riese et al., 24 Best Practice & Research Clinical Rheumatology, 513-526 (2010).*
N.K. Williams et al., 387 Journal of Molecular Biology, 219-232 (2009).*
B.H. Kim et al., 7 Molecular Cancer Therapeutics, 2672-2680 (2008).*
S.N. Constantinescu et al., 33 Trends in Biochemical Sciences, 122-131 (2007).*
T. Diaz et al., 6 PLoS One, (2011); E. Derezini et al., 1 Blood Cancer Journal, 1-11 (2011).*
L. Hertzberg et al., 115 Blood, 1006-1017 (2010).*
J. Jelinek et al., 106 Blood, 3370-3373 (2005).*
J.M. Kremer et al., 60 Arthritis & Rheumatism, 1895-1905 (2009).*
G.W. Booz et al., 34 Journal of molecular and cellular cardiology, 1443-1453 (2002).*
A. Kirabo et al., 3, Pharmaceuticals, 3478-3493 (2010).*
M. Kurdi et al., 297 American Journal of Physiology—Heart and Circulatory Physiology, 1545-1556 (2009).*
Luo et al., 36 Cell, 823-837 (2009).*
National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
S. Yamada et al., 242 The Journal of Pharmacology and Experimental Therapeutics, 326-330 (1987).*

(Continued)

*Primary Examiner* — Alexander R Pagano
(74) *Attorney, Agent, or Firm* — Scully, Scott, Murphy & Presser, P.C.

(57) ABSTRACT

The present invention relates to substituted pyrimidinyl-pyrrole compounds of formula (I) which modulate the activity of protein kinases and are therefore useful in treating diseases caused by dysregulated protein kinase activity, in particular Janus kinases. The present invention also provides methods for preparing these compounds, pharmaceutical compositions comprising these compounds, and methods of treating diseases utilizing such compounds or the pharmaceutical compositions containing them.

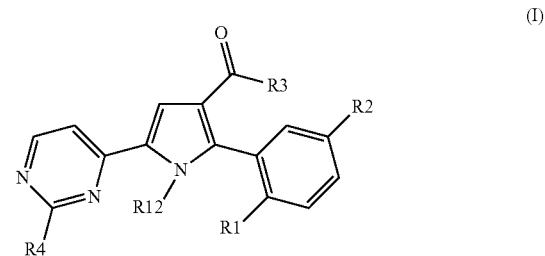

(I)

14 Claims, No Drawings

(56) References Cited

OTHER PUBLICATIONS

Kim et al., 150 Endocrinology, 3576-3583 (2009).*
B. Muller et al., Antiviral Strategies in, Antiviral Strategies 1-24, 4 (H.-G. Krausslich et al., eds., 2009).*
L. Emert-Sedlak et al., 4 ACS Chemical Biology, 939-947 (2009).*
S.K. Bhatia et al., Autoimmunity and autoimmune disease in 6 Principles of Medical Biology 239-263, 244 (1996).*
S.M. Hayter et al., Autoimmunity Reviews, 754-765, 756 (2012).*
H. Girouard et al., 100 Journal of Applied Physiology, 328-335, 332 (2006).*
R. S. Shah et al., 52 Biomedicine & Pharmacotherapy, 199-207 (2008).*
J.T. O'Brien et al., 2 The Lancet Neurology, 89-98, 96 (2003).*
I.V. Turko et al., Pharmacological Reviews, 619-634 (2002).*
F.A. Scappaticci et al., 99 Journal of the National Cancer Institute, 1232-1239 (2007).*
C. Ha et al., 104 The American Journal of Gastroenterology, 1445-1451 (2009).*
Kinase Inhibitors, Methods in Molecular Biology 795 (B. Kuster ed., 2012).*
L. Vijayakrishnan et al., 32 Trends in Pharmacological Sciences, 25-34 (2011).*
U. McDermott et al., 27 Journal of Clinical Oncology, 5650-5659 (2009).*
C.L. Sawyer, Nature, 548-552 (2008).*
C.M. Coughlin et al., Breast Cancer Research Treatment, 1-11 (2010).*
CAS Reg. No. 1162257-08-0 (Jul. 13, 2009).*
International Search Report dated May 14, 2012 issued in PCT/EP2012/056266.
Cohen P., "The Development and Therapeutic Potential of Protein Kinase Inhibitors", Current Opinion in Chemical Biology 3:459-465 (1999).
Cohen P., "Protein Kinases—The Major Drug Targets of the Twenty-First Century", Nature Reviews—Drug Discovery 1:309-315 (Apr. 2002).
Domagala J.M. et al., "New 7-Substituted Quinolone Antibacterial Agents. II. The Synthesis of 1-Ethyl-1,4-Dihydro-4-Oxo-7-(Pyrazolyl, Isoxazolyl, and Pyrimidinyl)-1,8-Naphthyridine and Quinolone-3-Carboxylic Acids", J. Heterocyclic Chem. 26:1147-1158 (Jul.-Aug. 1989).
Ghoreschi K. et al., "Janus Kinases in Immune Cell Signaling", Immunol Rev. 228(1):273-287 (Mar. 2009).
Gupton J.T. et al., "The Preparation of Heterocyclic Appended Vinylogous Iminium Salts and Their Application to the Regioselective Preparation of Biheterocyclic Systems", Heterocycles 47(2):689-702 (1998).
Ihle J.N., "Cytokine Receptor Signalling", Nature 377:591-594 (Oct. 19, 1995).
Leonard W.J. et al., "JAKS and STATS: Biological Implications", Annu. Rev. Immunol. 16:293-322 (1998).
Miyaura N. et al., "Palladium-Catalyzed Cross-Coupling Reactions of Organoboron Compounds", Chem. Rev. 95:2457-2483 (1995).
Moorthy J.N. et al., "Facile and Highly Selective Conversion of Nitriles to Amides Via Indirect Acid-Catalyzed Hydration Using TFA or AcOH-H2SO4", J. Org. Chem. 70(5):1926-1929 (Jan. 29, 2005).
Moorthy J.N. et al., Supporting Information—"Facile and Highly Selective Conversion of Nitriles to Amides Via Indirect Acid-Catalyzed Hydration Using TFA or AcOH-H2SO4", pp. S1-S9, Department of Chemistry, Indian Institute of Technology, Kanpur 208 016, India.
Suzuki A., "Cross-Coupling Reactions of Organoboron Compounds with Organic Halides", Metal-Catalyzed Cross-Coupling Reactions, 1st edition, pp. 49-97 (1998).
Veitch G.E. et al., "Magnesium Nitride as a Convenient Source of Ammonia: Preparation of Primary Amides", Organic Letters 10(16):3623-3625 (2008).
Veitch G.E. et al., Supporting Information—"Magnesium Nitride as a Convenient Source of Ammonia: Preparation of Primary Amides from Esters", pp. S1-S29, Department of Chemistry, Lensfield Rd, University of Cambridge, UK.
Velculescu V.E., "Defining the Blueprint of the Cancer Genome", Carcinogenesis 29(6):1087-1091 (2008).
Webert J-M, "Reactivity of Biheterocyclic Phenanthrene Analogs Toward Acetylation and Lithiation Agents", Journal of Heterocyclic Chemistry 20(1):61-64 (Jan.-Feb. 1983), together with an English-language abstract.
Yadav J.S. et al., "Zinc-Mediated Acylation and Sulfonation of Pyrrole and its Derivatives", Tetrahedron Letters 43:8133-8135 (2002).

* cited by examiner

SUBSTITUTED PYRIMIDINYL-PYRROLES ACTIVE AS KINASE INHIBITORS

INCORPORATION BY REFERENCE OF SEQUENCE LISTING

The Sequence Listing in an ASCII text file, named as 30482_SequenceListing.txt of 1 KB, created on Oct. 16, 2013, and submitted to the United States Patent and Trademark Office via EFS-Web, is incorporated herein by reference.

The present invention relates to certain substituted pyrimidinyl-pyrrole compounds, which modulate the activity of protein kinases. The compounds of this invention are therefore useful in treating diseases related to dysregulated kinases activity, for example cancer, cell proliferative disorders, viral infections, immune disorders, neurodegenerative disorders and cardiovascular diseases.

The present invention also provides methods for preparing these compounds, pharmaceutical compositions comprising these compounds and methods of treating diseases utilizing pharmaceutical compositions comprising these compounds.

Protein kinases mediate intracellular signaling by affecting a phosphoryl transfer from a nucleoside triphosphate to a protein acceptor that is involved in a signaling pathway. These phosphorylation events act as molecular on/off switches that can modulate or regulate the target protein's biological function and are ultimately triggered in response to a variety of extracellular and other stimuli. Examples of such stimuli include environmental and chemical stress signals (e.g. osmotic shock, heat shock, ultraviolet radiation, bacterial endotoxin and $H_2O_2$), cytokines (e.g., interleukin-3 (IL-3), IL-2) and growth factors (e.g., granulocyte macrophage-colony-stimulating factor (GM-CSF), fibroblast growth factor (FGF) and Erythropoietin (EPO). An extracellular stimulus may affect one or more cellular responses related to cell growth, migration, differentiation, secretion of hormones, activation of transcription factors, muscle contraction, glucose metabolism, control of protein synthesis and regulation of the cell cycle.

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases that include, but are not limited to, autoimmune diseases, inflammatory diseases, psoriasis, bone diseases, metabolic diseases, neurological and neurodegenerative diseases, cardiovascular diseases, allergies and asthma, Alzheimer's disease and hormone-related diseases. Accordingly, there has been a substantial effort in medicinal chemistry to find protein kinase inhibitors that are effective as therapeutic agents. For a general reference to PKs malfunctioning or deregulation see Current Opinions in Chemical Biology 1999, 3: 459-465, Nature Rev. Drug Discov. 2002; 1: 309-315 and Carcinogenesis 2008, 29: 1087-191.

The JAKs are a family of non-receptor tyrosine kinases consisting of JAK1, JAK2, JAK3 and TYK2. Whereas JAK1, JAK2 and TYK2 are expressed ubiquitously in mammals, JAK3 is primarily expressed in hematopoietic cells. The JAKs play a crucial role in hematopoietic cytokine and growth factors signaling (Nature 1995; 377: 591-594, Annu. Rev. Immunol. 1998; 16: 293-322) and are critically involved in cell growth, survival, development and differentiation of myeloid and immune cells. Effective innate and adaptive immune responses require functional JAK signaling to protect the organism from infections or tumors and mutations leading to loss of function make up some of the most common inherited severe immunodeficiencies. As a consequence JAK/STAT signaling has been implicated in the mediation of many abnormal immune responses such as allergies, asthma, autoimmune diseases, transplant rejection, rheumatoid arthritis, amyotrophic lateral sclerosis and multiple sclerosis as well as in solid and hematological malignancies like leukemias and lymphomas (Immunol Rev. 2009; 228: 273-287).

In particular JAK2 kinase is exclusively involved in the signal transduction mediated by Erythropoietin (EPO), Thrombopoietin (TPO), Growth Hormone (GH), Prolactin (PR) and by cytokines that signal through the common beta chain receptor IL-3, granulocyte-macrophage colony-stimulating factor (GM-CSF) and IL-5. In addition, JAK2 together with Jak1 and/or Tyk2 are important for the cytokines that signal through gp130 receptors (e.g. IL-6, IL-11), Type II cytokine receptors like IL-10, IL-19, IL-20 and IL-22, p40-containing containing cytokine receptors IL-12 and IL-23 and for the signal of Type I and II IFNs receptors (Immunol Rev. 2009; 228: 273-287). JAK3 kinase is primarily expressed in hematopoietic cells and is selectively associated with the common γ chain (γc), which is a shared component of the receptors for IL-2, IL-4, IL-7, IL-9, IL-15, and IL-21 that are cytokine involved in lymphoid development and function, and homeostasis of the immune system. TYK2 is primarily associated with Interferons, IL-12 and IL-23, but also with IL-10 and IL-6 signalling. All these growth factors and cytokines are mainly involved in proliferation and differentiation of Myeloid cells, inflammatory response and cancer (Blood. 2009; 114: 1289-1298, Clin Cancer Res. 2006; 12: 6270s-6273s, J Leukoc Biol. 2010; 88:1145-1156, Eur J Cancer. 2010; 46: 1223).

The binding of the ligand to the specific receptor seems to induce a conformational change in the receptor that allows trans- and/or autophosphorylation of the two bound JAK2 molecules. Activated JAK2 then phosphorylates specific tyrosine residues on the cytoplasmic tails of the receptors, creating docking sites for the SH2 domain of Signal Transducers and Activators of Transcription proteins (STAT). Once bound to the receptors, STATs are themselves phosphorylated by JAK2 on tyrosine residues. Phosphorylated STATs dimerize and translocate into the nucleus, where they regulate gene transcription. Thus, JAK2 is responsible for transducing a signal from the cell surface to the nucleus through a tyrosine phosphorylation signalling mechanism (J. Immun. 2007, 178:2623-2629, Oncogene 2007, 26: 6724-6737 and Cell Biochem Biophys. 2006, 44: 213-222)

JAK2, like the other JAKs, is characterized by a kinase domain (JH1) immediately adjacent to a pseudo-kinase domain (JH2) within the C-terminal half of the protein. The function of the pseudo-kinase domain is to negatively regulate the activity of the kinase domain (N. Engl. J. Med 2006, 355: 2452-2466). An activating point mutation of JAK2 (Valine to Phenylalanine substitution, JAK2-V617F) in the pseudo-kinase domain together with other activating mutations, in the JAK2 exon12 and in the TPO Receptor (MPLW515L/K), have been identified in Hematopoietic cells of patients with myeloproliferative disorders or MPD (Nature 2005; 434: 1144-8, N Engl J Med 2005; 352: 1779-90, Lancet 2005; 365: 1054-61, Cancer Cell 2005; 7: 387-97, Blood 2006, 108: 1427-1428 and Leukemia 2008, 22: 87-95). All of this data suggests that JAK2 is a suitable target for the development of a MPD specific therapy (Curr. Onc. Reports 2009, 11: 117-124). In addition JAK2 and in general the JAKs/STAT pathway, have been shown to be activated (e.g. mutation, amplification, translocation) in hematological malignancies like, but not limited to, AML, ALL, Hodgkin's Lymphoma, Diffuse large B cell Lymphoma and Mediastinal large B-Cell Lymphoma (Science 1997, 278:1309-1312, Trends in Biochemical Sciences 2007; 33: 122-131) and in a variety of solid tumors (e.g. mutation, STATs Phosphorylation, silencing of JAKs/STAT pathway inhibitors SOCS proteins, amplification). The pharmaceutical intervention in the JAKs/STAT pathway has been reviewed in AJP 2004; 165: 1449-1460, Cancer Res 2006; 66: 3162-3168, Clin Cancer Res. 2008; 14:3716-3721 and Immunol Rev. 2009; 228: 273-287.

Pyrimidinyl-pyrrole derivatives for the treatment of diseases associated by a dysregulated protein activity such as cancer are disclosed in WO2007/110344, in the name of the applicant itself. Some specific compounds of the aforementioned international patent application are excluded from the present general formula.

The present inventors have now discovered that compounds of formula (I), described below, are potent and selective JAK inhibitors and are thus useful in therapy of cancer, cell proliferative disorders, viral infections, immune disorders, neurodegenerative disorders and cardiovascular diseases.

Accordingly, a first object of the present invention is to provide a substituted pyrimidinyl-pyrrole compound represented by formula (I)

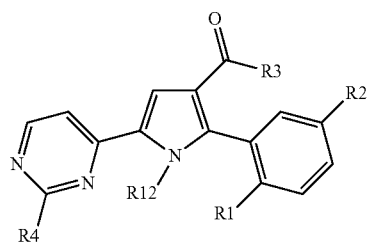

(I)

wherein:
R1 and R2 are independently halogen, nitro, cyano, OR5, NR6R7 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, arylalkyl, heterocyclyl and heterocyclyl-alkyl, wherein:
  R5 is hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, arylalkyl, heterocyclyl and heterocyclyl-alkyl;
  R6 and R7 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, arylalkyl, heterocyclyl and heterocyclyl-alkyl or R6 and R7, taken together with the nitrogen atom to which they are bonded, may form an optionally substituted 5 to 6 membered heteroaryl or heterocyclyl group optionally containing one additional heteroatom selected from N, O and S;
R3 is NR8R9 wherein:
  R8 and R9 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, arylalkyl, heterocyclyl and heterocyclyl-alkyl or R8 and R9, taken together with the nitrogen atom to which they are bonded, may form an optionally substituted 5 to 6 membered heteroaryl or heterocyclyl group optionally containing one additional heteroatom selected from N, O and S;
R4 is hydrogen, an optionally substituted straight or branched $C_1$-$C_6$ alkyl or NR10R11, wherein:
  R10 and R11 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, arylalkyl, heterocyclyl and heterocyclyl-alkyl or R10 and R11, taken together with the nitrogen atom to which they are bonded, may form an optionally substituted 5 to 6 membered heteroaryl or heterocyclyl group optionally containing one additional heteroatom selected from N, O and S;
R12 is hydrogen or an optionally substituted straight or branched $C_1$-$C_6$ alkyl;
or a pharmaceutically acceptable salt thereof, with the proviso that the following compounds are excluded:
5-(2-amino-pyrimidin-4-yl)-2-(5-fluoro-2-methyl-phenyl)-1H-pyrrole-3-carboxamide,
5-(2-amino-pyrimidin-4-yl)-2-(2,5-difluoro-phenyl)-1H-pyrrole-3-carboxamide,
5-(2-amino-pyrimidin-4-yl)-2-(2,5-dimethyl-phenyl)-1H-pyrrole-3-carboxamide,
5-(2-amino-pyrimidin-4-yl)-2-(5-chloro-2-methyl-phenyl)-1H-pyrrole-3-carboxamide,
5-(2-amino-pyrimidin-4-yl)-2-(5-chloro-2-fluoro-phenyl)-1H-pyrrole-3-carboxamide,
5-(2-amino-pyrimidin-4-yl)-2-(2-fluoro-5-methyl-phenyl)-1H-pyrrole-3-carboxamide and
5-(2-amino-pyrimidin-4-yl)-2-(2-chloro-5-fluoro-phenyl)-1H-pyrrole-3-carboxamide.

The present invention also provides methods of preparing the substituted pyrimidinyl-pyrrole compounds, represented by formula (I), prepared through a process consisting of standard synthetic transformations.

The present invention also provides a method for treating a disease caused by and/or associated with dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK4, PDGFR, PDK1, PERK, PIM1, PIM2, PKAalpha, PKCbeta, PLK1, RET, ROS1, SULU1, Syk, TLK2, TRKA, TYK2, VEGFR2, VEGFR3, ZAP70, more particularly the JAK family, which comprises administering to a mammal, in need thereof, an effective amount of a substituted pyrimidinyl-pyrrole compound represented by formula (I) as defined above. The mammal in need thereof may be for example a human.

A preferred method of the present invention is to treat a disease caused by and/or associated with dysregulated protein kinase activity selected from the group consisting of cancer, cell proliferative disorders, viral infections, immune-related disorders, neurodegenerative disorders and cardiovascular diseases.

Another preferred method of the present invention is to treat specific types of cancer including but not limited to: carcinoma such as bladder, breast, brain, colon, kidney, liver, lung, including small cell lung cancer, head and neck, esophagus, gall-bladder, ovary, uterine, pancreas, stomach, cervix, thyroid, prostate and skin, including squamous cell carcinoma; hematopoietic tumors of lymphoid lineage including leukaemia, T and B acute lymphoblastic leukemia (ALL), including DS-ALL, B-cell lymphoma, T-cell-lymphoma, Hodgkin's lymphoma, non-Hodgkin's lymphoma, Multiple Myeloma, Burkett's lymphoma and mantle cell lymphoma; hematopoietic tumors of myeloid lineage, including acute and chronic myelogenous leukemias, acute megakaryoblastic leukaemia, myelodysplastic syndrome and promyelocytic leukaemia, myeloproliferative disorders like Polycythemia Vera (PV), Essential Thrombocythemia (ET), Primary myelofibrosis and myelofibrosis secondary to PV and ET, chronic myelomonocytic leukemia; tumors of mesenchymal origin, including sarcoma, fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma, mesothelioma.

Another preferred method of the present invention is to treat specific types of cell proliferative disorders including but not limited to: benign prostate hyperplasia, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, comprising the prevention of AIDS development in HIV-infected individuals.

A preferred method of the present invention is to treat immune-related disorders including but not limited to: transplant rejection, skin disorders like psoriasis, allergies, asthma and autoimmune-mediated diseases such as rheumatoid arthritis (RA), systemic lupus erythematosus (SLE), Crohn's disease and amyotrophic lateral sclerosis.

Another preferred method of the present invention is to treat neurodegenerative disorders including but not limited to: Alzheimer's disease, degenerative nerve diseases, encephalitis, Stroke, Parkinson's Disease, Multiple Sclerosis, Amyotrophic Lateral Sclerosis (ALS or Lou Gehrig's Disease), Huntington's Disease and Pick's Disease.

Another preferred method of the present invention is to treat cardiovascular diseases including but not limited to: atherosclerosis primary or secondary to diabetes, heart attack and stroke.

In addition, the method of the present invention also provides tumor angiogenesis and metastasis inhibition as well as the treatment of organ transplant rejection and host versus graft disease.

Moreover, the method of the present invention further comprises subjecting the mammal in need thereof to a radiation therapy or chemotherapy regimen in combination with at least one cytostatic or cytotoxic agent.

The present invention also provides a pharmaceutical composition comprising a therapeutically effective amount of a compound of formula (I) or a pharmaceutically acceptable salt thereof and at least one pharmaceutically acceptable excipient, carrier and/or diluent.

In addition the present invention provides a pharmaceutical composition of a compound of the formula (I) further comprising one or more chemotherapeutic—e.g. cytostatic or cytotoxic-agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents like anti-HER agents, anti-EGFR agents, anti-Abl, anti-angiogenesis agents (e.g. angiogenesis inhibitors), farnesyl transferase inhibitors, ras-raf signal transduction pathway inhibitors, Akt pathway inhibitors, cell cycle inhibitors, other cdks inhibitors, tubulin binding agents, topoisomerase I inhibitors, topoisomerase II inhibitors and the like.

The present invention further provides an in vitro method for inhibiting JAK1, JAK2, JAK3 kinase protein activity which comprises contacting the kinase with an effective amount of a compound of formula (I) as defined above.

The present invention further provides a JAK2 dependent human megakaryoblastic leukemia cell line SET-2 assay which comprises contacting the cells with an effective amount of a compound of formula (I) as defined above.

Furthermore the present invention provides an in vivo model where acute megakaryoblastic leukemia cell line SET-2 was inoculated s.c. in 5-6 weeks old female severe combined immunodeficient (SCID) mice. Mice bearing a palpable tumor were treated with a compound of formula (I) for 10 days, bid. Tumor dimensions were measured regularly using Vernier calipers and tumor growth inhibition (TGI) was calculated.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

Unless otherwise specified, when referring to the compounds of the formula (I) per se as well as to any pharmaceutical composition thereof or to any therapeutic treatment comprising them, the present invention includes all of the hydrates, solvates, complexes, metabolites, pharmaceutically acceptable prodrug, pharmaceutically acceptable bio-precursors, carriers, N-oxides and pharmaceutically acceptable salts of the compounds of this invention.

A "metabolite" of a compound of the formula (I) is any compound into which this same compound of the formula (I) is converted in vivo, for instance upon administration to a mammal in need thereof. Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of the formula (I).

"Pharmaceutically acceptable prodrug" and "pharmaceutically acceptable bio-precursors" are any covalently bonded compounds, which release in vivo the active parent drug according to the formula (I).

The terms "pharmaceutically acceptable prodrug" and "pharmaceutically acceptable bio-precursors" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable benefit/risk ratio and effective for their intended use, as well as the zwitterionic forms, where possible, of the compounds of the invention. The term "prodrug" refers to compounds that are rapidly transformed in vivo to yield the active parent drug, according to formula (I), for example by hydrolysis in blood. A discussion is provided in T. Higuchi and V. Stella, Pro-drugs as Novel Delivery Systems, Vol. 14 of the A.C.S. Symposium Series and in Edward B. Roche, Bioreversible Carriers in Drug Design, American Pharmaceutical Association and Pergamon Press, 1987.

"N-oxides" are compounds of the formula (I) wherein nitrogen and oxygen are tethered through a dative bond.

Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid.

Pharmaceutically acceptable salts of the compounds of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

In the present description, unless otherwise specified, the following terms have the following meanings.

The term "aryl" includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms selected from N, O and S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "straight or branched $C_1$-$C_6$ alkyl", hence comprehensive of $C_1$-$C_4$ alkyl or $C_2$-$C_6$ alkyl, we intend any of the groups such as, for instance, methyl, ethyl, n-propyl, isopropyl, n-butyl, isobutyl, tert-butyl, sec-butyl, n-pentyl, n-hexyl and the like.

With the term "$C_3$-$C_7$ cycloalkyl" we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl and the like.

With the term "straight or branched $C_2$-$C_6$ alkynyl" we intend any of the groups such as, for instance, ethynyl, 2-propynyl, 4-pentynyl and the like.

According to the present invention and unless otherwise provided, any of the above R1, R2, R3, R4, R12 group may be optionally substituted, in any of their free positions, by one or more groups, for instance 1 to 6 groups, independently selected from: halogen atom, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term "halogen atom" we intend a fluorine, chlorine, bromine or iodine atom.

With the term "cyano" we intend a —CN residue.

With the term "nitro" we intend a —$NO_2$ group.

With the term "polyfluorinated alkyl or alkoxy" we intend any of the above straight or branched $C_1$-$C_6$ alkyl or alkoxy groups which are substituted by more than one fluorine atom such as, for instance, trifluoromethyl, trifluoroethyl, 1,1,1,3, 3,3-hexafluoropropyl, trifluoromethoxy and the like.

With the term "alkoxy", "aryloxy", "heterocyclyloxy" and derivatives thereof we intend any of the above $C_1$-$C_6$ alkyl, aryl or heterocyclyl groups linked to the rest of the molecule through an oxygen atom (—O—).

From all of the above, it is clear to the skilled person that any group which name is a composite name such as, for instance, "arylamino" has to be intended as conventionally constructed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Preferably, a compound of the formula (I) is characterized in that R4 is NR10R11, wherein R10 and R11 are independently hydrogen or an optionally substituted straight or branched $C_1$-$C_6$ alkyl; and R1, R2, R3 and R12 are as defined above.

More preferably, a compound of the formula (I) is characterized in that R3 is NR8R9, wherein R8 and R9 are independently hydrogen or an optionally substituted straight or branched $C_1$-$C_6$ alkyl; and R1, R2, R4 and R12 are as defined above.

Even more preferably, a compound of the formula (I) is characterized in that R12 is hydrogen; and R1, R2, R3 and R4 are as defined above.

Specific, not limiting, preferred compounds (cmpds.) of the invention, whenever appropriate in the form of pharmaceutically acceptable salts, are the following:

1. 5-(2-Aminopyrimidin-4-yl)-2-[2-chloro-5-(trifluoromethyl)phenyl]-1H-pyrrole-3-carboxamide,
2. 5-(2-Aminopyrimidin-4-yl)-2-(2,5-dichlorophenyl)-1H-pyrrole-3-carboxamide,
3. 5-(2-Aminopyrimidin-4-yl)-2-(5-chloro-2-methoxyphenyl)-1H-pyrrole-3-carboxamide,
4. 5-(2-Aminopyrimidin-4-yl)-2-(2-chloro-5-ethylphenyl)-1H-pyrrole-3-carboxamide,
5. 5-(2-Aminopyrimidin-4-yl)-2-(5-chloro-2-ethylphenyl)-1H-pyrrole-3-carboxamide,
6. 5-(2-Aminopyrimidin-4-yl)-2-(2-chloro-5-methylphenyl)-1H-pyrrole-3-carboxamide,
7. 5-(2-Aminopyrimidin-4-yl)-2-(2-chloro-5-cyanophenyl)-1H-pyrrole-3-carboxamide,
8. 5-(2-Aminopyrimidin-4-yl)-2-(5-bromo-2-methoxyphenyl)-1H-pyrrole-3-carboxamide,
9. 5-(2-Aminopyrimidin-4-yl)-2-(5-bromo-2-fluorophenyl)-1H-pyrrole-3-carboxamide,
10. 5-(2-Aminopyrimidin-4-yl)-2-[2-chloro-5-(hydroxymethyl)phenyl]-1H-pyrrole-3-carboxamide,
11. 5-(2-Aminopyrimidin-4-yl)-2-(2-chloro-5-methoxyphenyl)-1H-pyrrole-3-carboxamide,
12. 5-(2-Aminopyrimidin-4-yl)-2-[2-chloro-5-(trifluoromethoxy)phenyl]-1H-pyrrole-3-carboxamide,
13. 5-(2-Aminopyrimidin-4-yl)-2-[2-methyl-5-(trifluoromethyl)phenyl]-1H-pyrrole-3-carboxamide,
14. 5-(2-Aminopyrimidin-4-yl)-2-[5-chloro-2-(propan-2-yl)phenyl]-1H-pyrrole-3-carboxamide,
15. 5-(2-Aminopyrimidin-4-yl)-2-[2,5-bis(trifluoromethyl)phenyl]-1H-pyrrole-3-carboxamide,
16. 5-(2-Aminopyrimidin-4-yl)-2-[2-ethyl-5-(trifluoromethyl)phenyl]-1H-pyrrole-3-carboxamide,
17. 5-(2-Aminopyrimidin-4-yl)-2-[5-chloro-2-(trifluoromethyl)phenyl]-1H-pyrrole-3-carboxamide,
18. 5-(2-Aminopyrimidin-4-yl)-2-(5-cyano-2-methylphenyl)-1H-pyrrole-3-carboxamide,
19. 5-(2-Aminopyrimidin-4-yl)-2-(5-chloro-2-methylphenyl)-N-methyl-1H-pyrrole-3-carboxamide,
20. 5-(2-Aminopyrimidin-4-yl)-2-(5-chloro-2-methylphenyl)-N-ethyl-1H-pyrrole-3-carboxamide,
21. 5-(2-Aminopyrimidin-4-yl)-2-(5-chloro-2-methylphenyl)-N-(2-hydroxyethyl)-1H-pyrrole-3-carboxamide,
22. 5-(2-Aminopyrimidin-4-yl)-2-(5-chloro-2-methylphenyl)-N-[2-(piperidin-1-yl)ethyl]-1H-pyrrole-3-carboxamide,
23. 5-(2-Aminopyrimidin-4-yl)-2-(5-chloro-2-methylphenyl)-N-(1-methylpiperidin-4-yl)-1H-pyrrole-3-carboxamide,
24. 5-(2-Aminopyrimidin-4-yl)-2-(5-chloro-2-methylphenyl)-N-phenyl-1H-pyrrole-3-carboxamide,
25. 5-(2-Aminopyrimidin-4-yl)-2-(5-chloro-2-methylphenyl)-N-(furan-2-ylmethyl)-1H-pyrrole-3-carboxamide,
26. 5-(2-Aminopyrimidin-4-yl)-2-(5-chloro-2-methylphenyl)-N-(3-hydroxypropyl)-1H-pyrrole-3-carboxamide,
27. 5-(2-Aminopyrimidin-4-yl)-2-(5-chloro-2-methylphenyl)-N-(2-methoxyethyl)-1H-pyrrole-3-carboxamide,
28. 5-(2-Aminopyrimidin-4-yl)-2-(5-chloro-2-methylphenyl)-N-(2-fluoroethyl)-1H-pyrrole-3-carboxamide,
29. 5-(2-Aminopyrimidin-4-yl)-2-(5-chloro-2-methylphenyl)-N,N-dimethyl-1H-pyrrole-3-carboxamide,
30. N-(2-Aminoethyl)-5-(2-aminopyrimidin-4-yl)-2-(5-chloro-2-methylphenyl)-1H-pyrrole-3-carboxamide,
31. 5-(2-Aminopyrimidin-4-yl)-2-(5-chloro-2-methylphenyl)-N-[2-(methylamino)ethyl]-1H-pyrrole-3-carboxamide,
32. 5-(2-Aminopyrimidin-4-yl)-N-benzyl-2-(5-chloro-2-methylphenyl)-1H-pyrrole-3-carboxamide,
33. 5-(2-Aminopyrimidin-4-yl)-2-(5-chloro-2-methylphenyl)-N-(2-methylpropyl)-1H-pyrrole-3-carboxamide,
34. 5-(2-Aminopyrimidin-4-yl)-2-(5-chloro-2-methylphenyl)-N-(2,2-dimethylpropyl)-1H-pyrrole-3-carboxamide,
35. 5-(2-Aminopyrimidin-4-yl)-2-(5-chloro-2-ethylphenyl)-N-methyl-1H-pyrrole-3-carboxamide,
36. 5-(2-Aminopyrimidin-4-yl)-2-(5-chloro-2-ethylphenyl)-N-ethyl-1H-pyrrole-3-carboxamide,
37. 5-(2-aminopyrimidin-4-yl)-2-(5-chloro-2-ethylphenyl)-N-(2-hydroxyethyl)-1H-pyrrole-3-carboxamide,
38. 5-(2-Aminopyrimidin-4-yl)-2-(5-chloro-2-ethylphenyl)-N,N-dimethyl-1H-pyrrole-3-carboxamide,
39. 5-(2-Aminopyrimidin-4-yl)-2-[2-chloro-5-(trifluoromethyl)phenyl]-N-methyl-1H-pyrrole-3-carboxamide,
40. 5-(2-Aminopyrimidin-4-yl)-2-(5-chloro-2-hydroxyphenyl)-1H-pyrrole-3-carboxamide,
41. 5-(2-Aminopyrimidin-4-yl)-2-(2-chloro-5-hydroxyphenyl)-1H-pyrrole-3-carboxamide,
42. 2-(5-chloro-2-methylphenyl)-5-[2-(methylamino)pyrimidin-4-yl]-1H-pyrrole-3-carboxamide,
43. 5-(Pyrimidin-4-yl)-2-(5-chloro-2-methyl-phenyl)-1H-pyrrole-3-carboxamide,
44. 2-(5-Chloro-2-methylphenyl)-5-(2-methylpyrimidin-4-yl)-1H-pyrrole-3-carboxamide,
45. 5-(2-Aminopyrimidin-4-yl)-2-(5-chloro-2-ethylphenyl)-1-methyl-1H-pyrrole-3-carboxamide,
46. 5-(2-Aminopyrimidin-4-yl)-2-(5-chloro-2-methylphenyl)-1-methyl-1H-pyrrole-3-carboxamide,
47. 5-(2-Aminopyrimidin-4-yl)-2-(5-chloro-2-methylphenyl)-1-ethyl-1H-pyrrole-3-carboxamide,
48. 5-(2-Aminopyrimidin-4-yl)-2-(5-chloro-2-methylphenyl)-1-(2,2,2-trifluoroethyl)-1H-pyrrole-3-carboxamide,
49. 5-(2-Aminopyrimidin-4-yl)-2-(5-chloro-2-methylphenyl)-1-(2-hydroxyethyl)-1H-pyrrole-3-carboxamide,
50. 5-(2-Aminopyrimidin-4-yl)-N-methyl-2-[2-methyl-5-(trifluoromethyl)phenyl]-1H-pyrrole-3-carboxamide and
51. 5-(2-Aminopyrimidin-4-yl)-2-[2-ethyl-5-(trifluoromethyl)phenyl]-N-methyl-1H-pyrrole-3-carboxamide.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art or by making routine modifications of reaction conditions. Alternatively other reactions referred to herein or known in the art will be recognized as having adaptability for preparing other compounds of the invention.

The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991 and references cited therein.

A compound of formula (I) can be prepared according to the general synthetic processes described hereafter in schemes A, B, C and D.

The reported Scheme A shows the preparation of a compound of formula (I) wherein R1, R2 and R3 are as defined above, R4 is NH$_2$ and R12 is hydrogen.

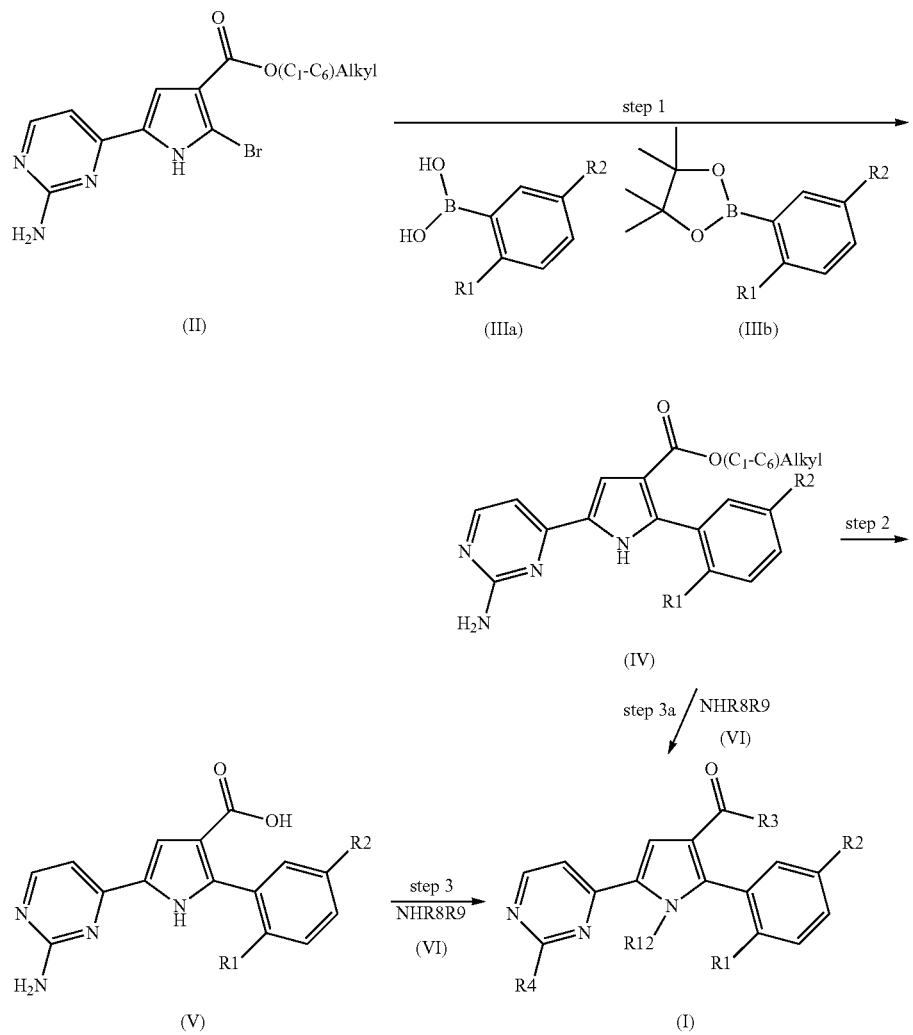

In the above scheme R1, R2, R3, R8 and R9 are as defined above, R4 is NH$_2$ and R12 is hydrogen.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

Step 1: Metal-Catalyzed Coupling Reaction of a Halo Derivative of Formula (II)

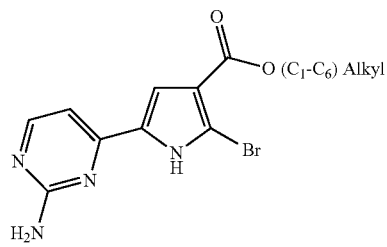
(II)

with a substituted aryl boronic acid of formula (IIIa) or an aryl boronic ester of formula (IIIb):

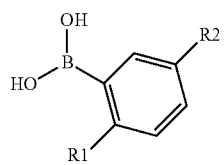
(IIIa)

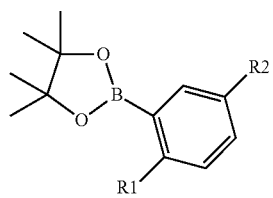
(IIIb)

wherein R1 and R2 are as defined above;

Step 2: Hydrolysis of the Resulting Carboxylic Ester of Formula (IV)

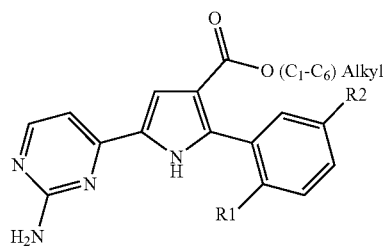
(IV)

wherein R1 and R2 are as defined above, through basic hydrolysis;

Step 3: Amidation of the Resulting Carboxylic Acid of Formula (V)

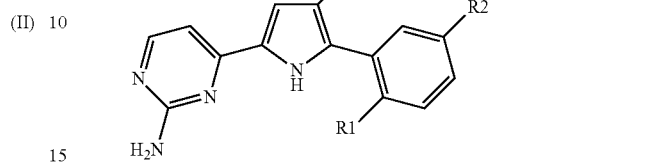
(V)

wherein R1 and R2 are as defined above, through reaction with a derivative of formula (VI)

NHR8R9 (VI)

wherein R8 and R9 are as defined above, to give a compound of formula (I)

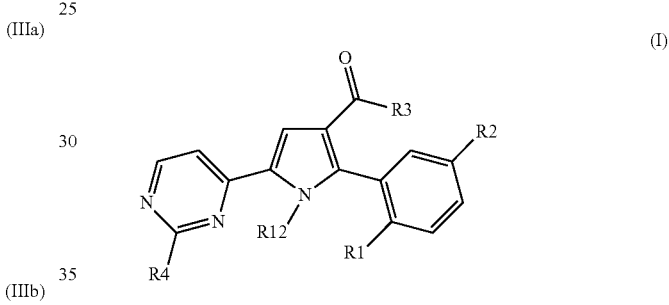
(I)

wherein R1, R2 and R3 are as defined above, R4 is NH$_2$ and R12 is hydrogen;

or

Step 3a: Direct Amidation of the Carboxylic Ester of Formula (IV) as Defined Above Through Reaction with a Derivative of Formula (VI) as Defined Above to Give a Compound of Formula (I)

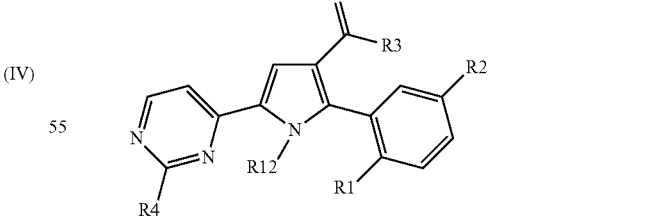
(I)

wherein R1, R2 and R3 are as defined above, R4 is NH$_2$ and R12 is hydrogen;

optionally converting a compound of the formula (I) into another different compound of the formula (I) and, if desired, converting a compound of the formula (I) into a pharmaceutically acceptable salt thereof or converting a salt into the free compound (I).

According to the Step 1 of Scheme A, the conversion of a halo derivative of general formula (II) into a compound of formula (IV) can be accomplished in a variety of ways. For example a compound of formula (II) can be reacted by metal-catalyzed coupling reactions with a substituted aryl boronic acid of formula (IIIa) or aryl boronic ester of formula (IIIb). Preferably, a compound of formula (IV) can be prepared from intermediates (II) by Pd-catalyzed Suzuki-Miyaura coupling with a substituted aryl boronic acid of general formula (IIIa) or aryl boronic ester of general formula (IIIb). Transition metal-catalyzed couplings of (hetero)aryl halides with aryl boronic acids or boronic esters are well known to the person skilled in the art, see references: a) Miyaura, Norio; Suzuki, Akira (1979). "Palladium-Catalyzed Cross-Coupling Reactions of Organoboron Compounds", *Chemical reviews* 95 (7): 2457-2483; b) Suzuki, A. In Metal-Catalyzed Cross-Coupling Reactions, Diederich F. and Stang P. J., Eds. Wiley-VCH: New York, 1998, pp. 49-97. In the so called Suzuki-Miyaura reaction, coupling reaction of aryl boronic acids or boronic ester with (hetero)aryl halides is typically triggered by palladium complex. Phosphine-palladium complexes such as tetrakis(triphenylphosphine)palladium(0) are used for this reaction but also bis(triphenylphosphine)palladium (II) chloride, [1,1'-bis(diphenylphosphino)ferrocene] dichloro palladium(II) may be employed. A base such as potassium phosphate, sodium carbonate, cesium carbonate, potassium carbonate, potassium t-butoxide, tetraethyl ammonium hydroxide, triethylamine is added and tetrahydrofurane, dioxane, N,N-dimethylformamide, ethanol and toluene may be used as reaction media. Typically temperatures range from room temperature to 150° C. Conventional heating along with microwave irradiation may be employed. Reaction duration ranges from about 30 min to about 96 hours. Various Pd-catalyst/base/solvent combinations have been described in the literature which allows the fine-tuning of the reaction conditions in order to allow for a broad set of additional functional groups on both coupling partners.

According to the Step 2 of Scheme A, the hydrolysis of a derivative of formula (IV) into a carboxylic acid of formula (V) can be accomplished in a variety of ways. Typically NaOH or KOH in alcoholic solution is used at a temperature ranging from room temperature to 150° C., for a time ranging from about 30 min to about 96 hours.

According to the Step 3 of Scheme A, the conversion of a carboxylic acid of formula (V) into an amide of formula (I) can be accomplished in a variety of ways and experimental conditions, which are widely known in the art for the preparation of carboxamides. As an example, a compound of formula (V) can be converted into its corresponding acyl chloride in the presence of thionyl chloride or oxalyl chloride, in a suitable solvent such as toluene, dichloromethane, chloroform, diethyl ether, tetrahydrofuran, dioxan, at a temperature ranging from about −10° C. to reflux and for a period of time varying from about 1 hour to about 96 hours. The acyl chloride can be isolated by evaporation of the solvent and further reacted with 33% ammonium hydroxide solution or with an amine NHR8R9 (VI) in a suitable solvent, such as toluene, dichloromethane, chloroform, diethyl ether, tetrahydrofuran, dioxane, at a temperature ranging from about −10° C. to reflux and for a period of time varying from about 1 hour to about 96 hours. Alternatively, a compound of formula (V) can be reacted with the ammonium salt of 1-hydroxybenzotriazole or with an amine NHR8R9 (VI) in the presence of a carbodiimide such as dicyclohexyl carbodiimide, diisopropyl carbodiimide, 1-ethyl-3-(3'-dimethylamino)carbodiimide hydrochloric acid salt. Preferably, this reaction is carried out in a suitable solvent such as, for instance, tetrahydrofuran, dichloromethane, toluene, dioxane, N,N-dimethylformamide and in the presence of a proton scavenger such as, for example, triethylamine, N,N-diisopropylethylamine, at a temperature ranging from room temperature to reflux, for a time ranging from about 30 min to about 96 hours.

According to step 3a of Scheme A, the direct transformation of the ester (IV) into a compound of formula (I) is also synthetically feasible and is intended to be included into the scope of the invention. Recent literature data suggest for example that such transformation may easily be performed by employing magnesium nitride ($Mg_3N_2$) in a suitable solvent such an alcohol under microwave irradiation (Gemma, E.; Veitch, G. E.; Bridgwood, K. L.; Ley, S. V. *Org. Lett.* 2008, 10, 3623).

The present invention further provides an alternative process for the preparation of a compound of formula (I), wherein R1, R2 and R3 are as defined above, R4 is $NH_2$ and R12 is hydrogen, which is shown in Scheme B below.

Scheme B

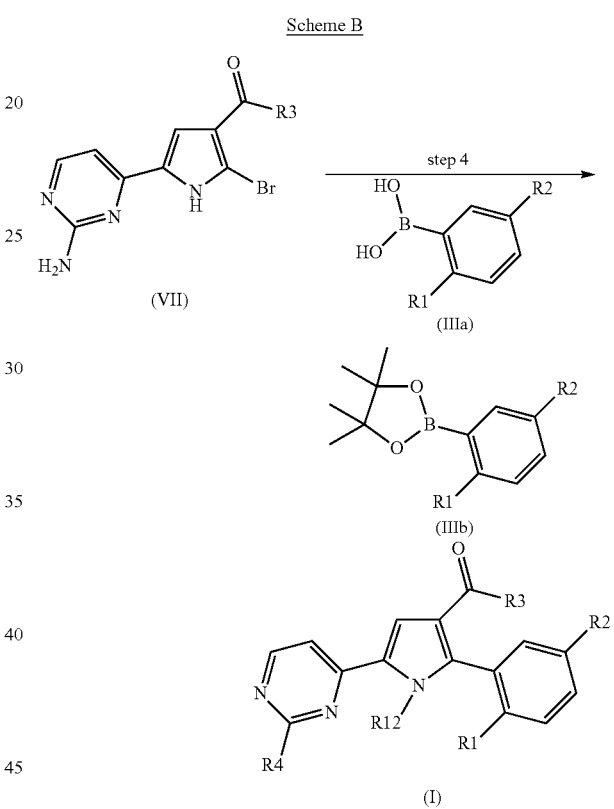

In the above scheme R1, R2 and R3 are as defined above, R4 is $NH_2$ and R12 is hydrogen.

Accordingly, another process of the present invention comprises the following step:

Step 4: Metal-Catalyzed Coupling Reaction of a Halo Derivative of Formula (VII)

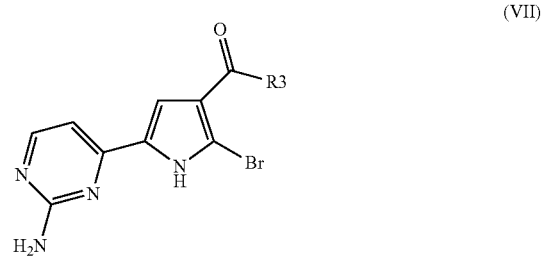

wherein R3 is as defined above, with a substituted aryl boronic acid of formula (IIIa) or an aryl boronic ester of formula (IIIb)

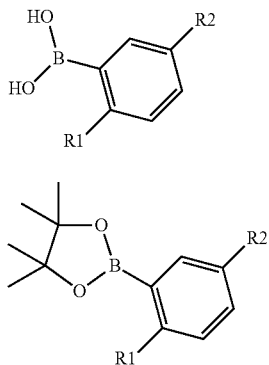

wherein R1 and R2 are as defined above, to give a compound of formula (I)

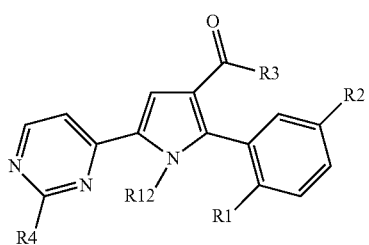

wherein R1, R2 and R3 are as defined above, R4 is NH₂ and R12 is hydrogen; optionally converting a compound of the formula (I) into another different compound of the formula (I) and, if desired, converting a compound of the formula (I) into a pharmaceutically acceptable salt thereof or converting a salt into the free compound (I).

According to step 4 of Scheme B, the conversion of a halo derivative of general formula (VII) into a compound of general formula (I) may be carried out under the variety of conditions already described in step 1 of Scheme A.

The present invention further provides an alternative process for the preparation of a compound of formula (I), wherein R1 and R2 are as defined above, R3 is NH₂, R4 is NR10R11, wherein R10 and R11 are as defined above, and R12 is hydrogen, which is shown in Scheme C below.

Scheme C

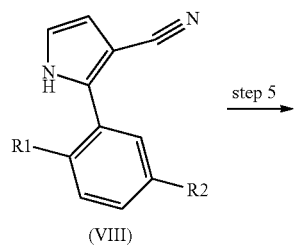

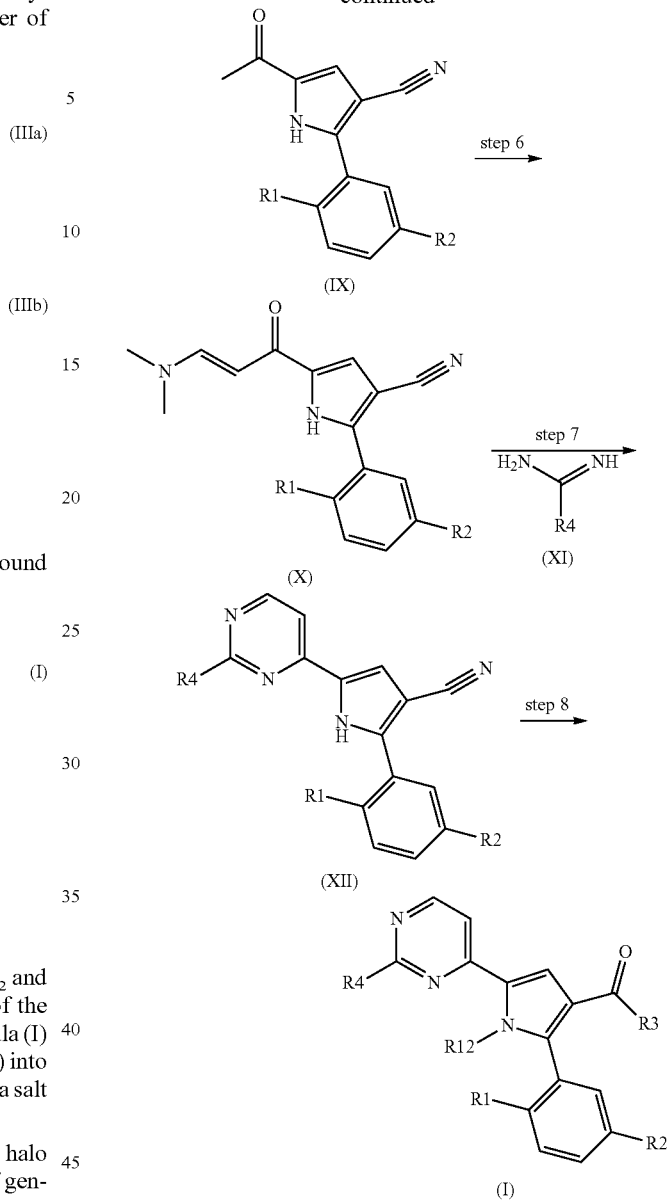

In the above scheme R1 and R2 are as defined above, R3 is NH₂, R4 is NR10R11, wherein R10 and R11 are as defined above, and R12 is hydrogen.

Accordingly, another process of the present invention comprises the following steps:

Step 5: Reacting a Pyrrole of the Formula (VIII)

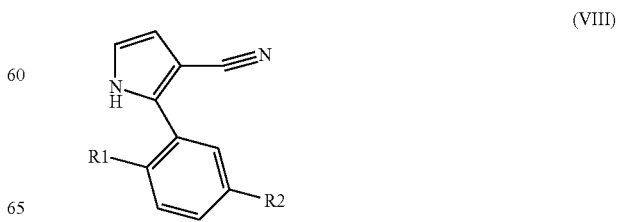

wherein R1 and R2 are as defined above, with acetyl chloride in the presence of a Lewis acid or in the presence of zinc metal;

Step 6: Reacting the Resultant Compound of the Formula (IX)

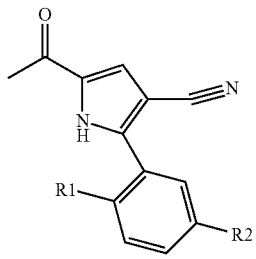

(IX)

wherein R1 and R2 are as defined above, with a dialkyl acetal of N,N-dimethylformamide;

Step 7: Reacting the Resultant Enaminone of the Formula (X)

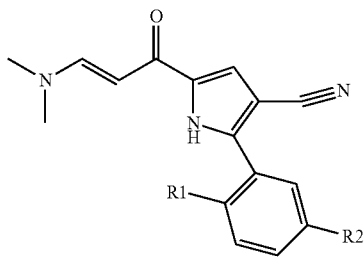

(X)

wherein R1 and R2 are as defined above, with an optionally substituted guanidine of formula (XI) or a salt thereof

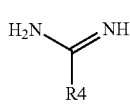

(XI)

wherein R4 is NR10R11 and R10 and R11 are as defined above;

Step 8: Hydrolizing in Acidic Conditions the Cyano Group of the Resultant Compound of the Formula (XII)

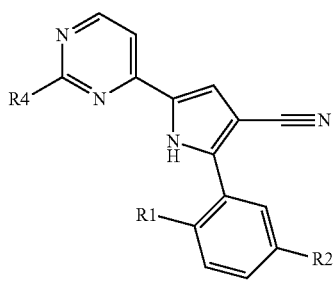

(XII)

wherein R4 is NR10R11, wherein R10 and R11 are as defined above, and R1 and R2 are as defined above, so as to obtain the compound of the formula (I)

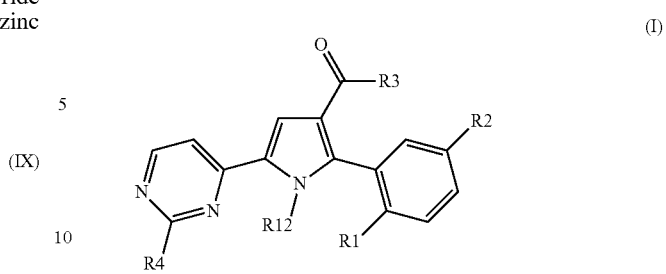

(I)

wherein R1 and R2 are as defined above, R3 is NH$_2$, R4 is NR10R11, wherein R10 and R11 are as defined above, and R12 is hydrogen; optionally converting a compound of the formula (I) into another different compound of the formula (I) and, if desired, converting a compound of the formula (I) into a pharmaceutically acceptable salt thereof or converting a salt into the free compound (I).

According to the Step 5 of Scheme C, the acylation of a compound of the formula (VIII) to give a compound of the formula (IX) is preferably performed with acetyl chloride in the presence of a Lewis acid, for instance aluminum trichloride or titanium tetrachloride, operating under cooling, e.g. at a temperature from −5° C. to 0° C., or at room temperature, in an anhydrous organic solvent, e.g. dichloromethane. A similar reaction is described in *J. Het. Chem.* 1983, 20, 61. Otherwise, the acylation of a compound of the formula (VIII) to give a compound of the formula (IX) is performed with acetyl chloride in the presence of zinc metal, operating at a temperature from room temperature to reflux, in an anhydrous organic solvent, e.g. toluene. A similar reaction is described in *Te. Le.* 2002, 43, 8133.

According to the Step 6 of Scheme C, the conversion of a compound of the formula (IX) into the enaminone of the formula (X) may be carried out using a dialkyl acetal, for instance the dimethyl acetal or diisopropyl acetal of N,N-dimethylformamide. Preferably the reaction is carried out at a temperature between room and reflux temperature, preferably at a temperature from 60° C. to 90° C., in an organic solvent such as, e.g., toluene, benzene, dichloroethane or N,N-dimethylformamide. An analogous transformation was described, for instance, in Heterocycles 1998, 47, 689.

According to the Step 7 of Scheme C, the conversion of a compound of the formula (X) into a compound of the formula (XII) is carried out by reaction with guanidine or substituted guanidine of the formula (XI) or a salt thereof. Preferably the reaction is carried out at a temperature from 80° C. to 130° C. in an organic solvent such as, e.g., acetamide, N-methyl-2-pyrrolidone, N,N-dimethylformamide, in the presence of a base such as potassium carbonate. Such kind of conversion is described in the scientific literature, for example in *J. Het. Chem.* 1989, 26, 1147.

According to the Step 8 of Scheme C, the hydrolysis in acidic condition of the nitrile derivative of the formula (XII) to yield the carboxamide of the formula (I) is preferably performed in glacial acetic acid or trifluoroacetic acid and concentrated sulfuric acid, more preferably in ratios between 1 to 1 and 5 to 1, optionally in the presence of water, at a temperature between room temperature and 120° C., in particular at a temperature of from 60° C. to 90° C. An analogous hydrolysis is for example described in *J. Org. Chem.* 2005, 70, 1926. After basification with concentrated aqueous ammonia, sodium hydroxide or potassium hydroxide, the free base is filtered off as a precipitate.

The present invention further provides an alternative process for the preparation of a compound of formula (I), wherein R1 and R2 are as defined above, R3 is NH$_2$, R4 is hydrogen or optionally substituted straight or branched (C$_1$-C$_6$) alkyl, and R12 is hydrogen, which is shown in Scheme D below.

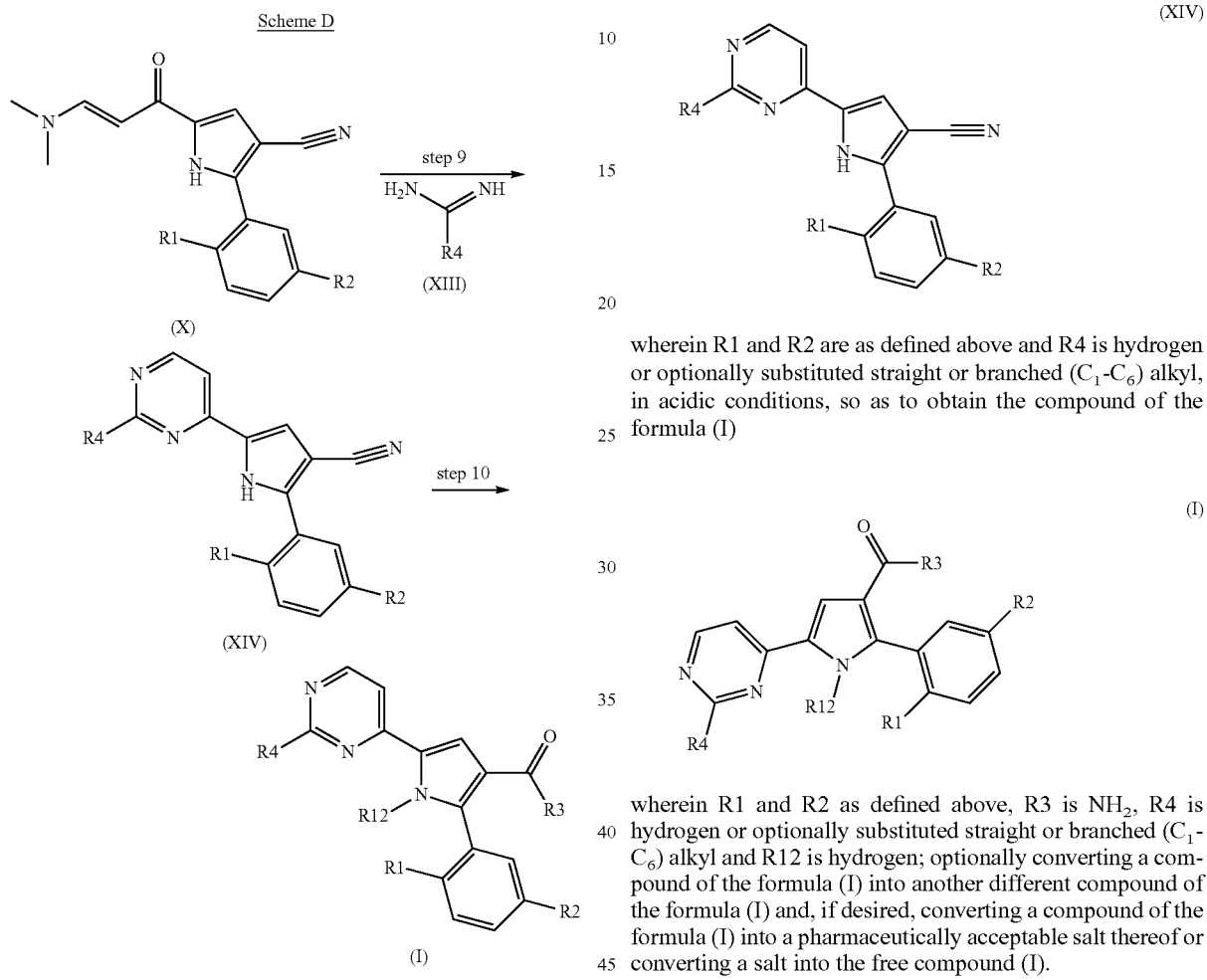

In the above scheme R1 and R2 are as defined above, R3 is NH$_2$, R4 is hydrogen or optionally substituted straight or branched (C$_1$-C$_6$) alkyl and R12 is hydrogen.

Accordingly, another process of the present invention comprises the following steps:

Step 9: Reacting the Enaminone of the Formula (X) as Defined Above, with an Optionally Substituted Amidine of the Formula (XIII) or a Salt Thereof

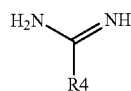

(XIII)

wherein R4 is hydrogen or optionally substituted straight or branched (C$_1$-C$_6$) alkyl;

Step 10: Hydrolizing the Cyano Group of the Resultant Compound of the Formula (XIV)

wherein R1 and R2 are as defined above and R4 is hydrogen or optionally substituted straight or branched (C$_1$-C$_6$) alkyl, in acidic conditions, so as to obtain the compound of the formula (I)

wherein R1 and R2 as defined above, R3 is NH$_2$, R4 is hydrogen or optionally substituted straight or branched (C$_1$-C$_6$) alkyl and R12 is hydrogen; optionally converting a compound of the formula (I) into another different compound of the formula (I) and, if desired, converting a compound of the formula (I) into a pharmaceutically acceptable salt thereof or converting a salt into the free compound (I).

According to the Step 9 of Scheme D, the conversion of a compound of the formula (X) into a compound of the formula (XIV) is carried out by reaction with formamidine or substituted amidine of the formula (XIII) or a salt thereof. Preferably the reaction is carried out at a temperature of from 80° C. to 150° C. in an organic solvent such as, e.g., acetamide, N-methyl-2-pyrrolidone, N,N-dimethylformamide.

According to the Step 10 of Scheme D, the hydrolysis in acidic condition of the nitrile derivative of the formula (XIV) to yield the compound of the formula (I) may be carried out under the variety of conditions already described in Step 8 of Scheme C.

As indicated above, a compound of the formula (I), which is prepared according to the processes object of the invention, can be conveniently converted into another compound of the formula (I) by operating according to well-known synthetic conditions, the following being examples of possible conversions:

conv.1) converting a compound of the formula (I), wherein one of R1 or R2 is OCH$_3$, into the corresponding compound of formula (I), wherein one of R1 or R2 is OH, by treatment with BCl$_3$ or BBr$_3$ in a solvent such as dichloromethane, chloroform, dichloroethane, acetonitrile at a temperature ranging from −20° C. to reflux from about 30 min to about 96 hours:

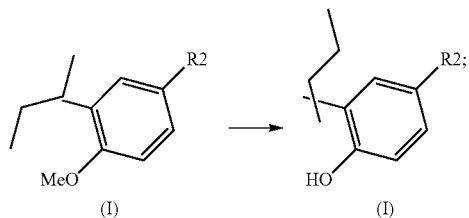

conv.2) converting a compound of the formula (I), wherein R12 is hydrogen, into the corresponding compound of formula (I), wherein R12 is an optionally substituted straight or branched ($C_1$-$C_6$) alkyl,

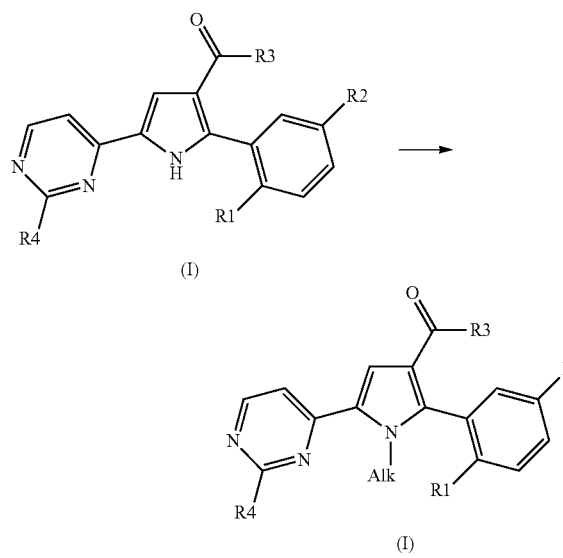

by treatment with optionally substituted alkyl halide of the formula R12'-X (XV), wherein R12' is an optionally substituted straight or branched ($C_1$-$C_6$) alkyl and X is halogen, in a solvent such as N,N-dimethylformamide and in the presence of a base at a temperature ranging from room temperature to reflux from about 30 min to about 96 hours.

From all of the above it is clear to the skilled person that any compound of the formula (I) bearing a functional group which can be further derivatized to another functional group, by working according to methods well known in the art thus leading to other compounds of the formula (I), is intended to be comprised within the scope of the present invention.

Needless to say, also any of the intermediates of the above described processes could be converted into a different intermediate, if wanted and necessary, by operating in an analogous way as in any one of the conversion reaction here above described.

From all of the above, it is clear to the skilled person that when preparing the compounds of the formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of the formula (I) prepared according to the process described above are obtained as mixture of isomers, their separation using conventional techniques into the single isomers of the formula (I) is within the scope of the present invention.

The final compounds may be isolated and purified using conventional procedures, for example chromatography and/or crystallization and salt formation.

The carboxamides of the formula (I) as defined above can be converted into pharmaceutically acceptable salts. The carboxamides of the formula (I), as defined above, or the pharmaceutically acceptable salts thereof can be subsequently formulated with a pharmaceutically acceptable carrier or diluent to provide a pharmaceutical composition.

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

In cases where a compound of formula (I) contains one or more asymmetric centers, said compound can be separated into the single isomers by procedures known to those skilled in the art. Such procedures comprise standard chromatographic techniques, including chromatography using a chiral stationary phase or crystallization. General methods for separation of compounds containing one or more asymmetric centers are reported, for instance, in Jacques, Jean; Collet, André; Wilen, Samuel H., —*Enantiomers, Racemates, and Resolutions*, John Wiley & Sons Inc., New York (N.Y.), 1981.

According to any variant of the process for preparing the compounds of the formula (I), the starting materials and any other reactants are known or easily prepared according to known methods.

The starting materials of the formula (II) and (VII) can be prepared as described in WO2007/110344.

The starting material of the formula (VIII) can be prepared by known methods or as described in the experimental part below (Preparations D and E).

The compounds of the formula (IIIa), (IIIb), (VI), (XI), (XIII) and (XV) are either commercially available or can be prepared with known methods; the compounds of the formula (IIIa) can also be prepared as described in the experimental part below (Preparations A, B and C).

The present invention also provides an intermediate of formula (IIIa):

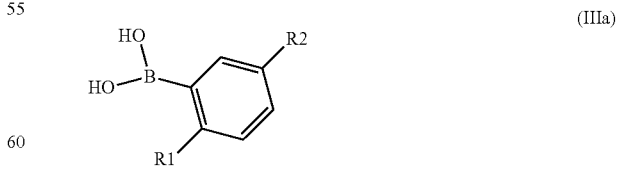

wherein
R1 is ethyl and R2 is chlorine or $CF_3$, or
R1 is isopropyl and R2 is chlorine.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of the formula (I) may be used sequentially with known anticancer agents when a combination formulation is inappropriate.

The compounds of the formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of the formula (I) may range from about 10 to about 500 mg per dose, from 1 to 5 times daily. The compounds of the invention can be administered in a variety of dosage forms, e.g., orally, in the form of tablets, capsules, sugar or film coated tablets, liquid solutions or suspensions; rectally in the form of suppositories; parenterally, e.g., intramuscularly, or through intravenous and/or intrathecal and/or intraspinal injection or infusion.

The present invention also includes pharmaceutical compositions comprising a compound of the formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol. The suspensions or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods which are well known in the art.

General Purification and Analytical Methods

The synthetic preparation of some compounds of the formula (I) of the invention is described in the following examples. The compounds of the present invention, as prepared according to the following examples, were also characterized by $^1$H NMR and/or by Exact mass data ESI(+).

$^1$H-NMR spectrometry was performed on a Mercury VX 400 operating at 400.45 MHz equipped with a 5 mm double resonance probe [1H (15N-31P) ID_PFG Varian]. ESI(+) high resolution mass spectra (HRMS) were obtained on a Waters Q-Tof Ultima directly connected with micro HPLC 1100 Agilent as previously described (M. Colombo, F. Riccardi-Sirtori, V. Rizzo, *Rapid Commun. Mass Spectrom.* 2004, 18, 511-517). Column chromatography was conducted either under medium pressure on silica (Merck silica gel 40-63 µm) or on prepacked silica gel cartridges (Biotage). Components were visualized by UV light (λ: 254 nm) and by iodine vapor. HPLC was performed on Waters X Terra RP 18 (4.6×50 mm, 3.5 µm) column using a Waters 2790 HPLC system equipped with a 996 Waters PDA detector and Watersmod. ZQ single quadrupole mass spectrometer, equipped with an electrospray (ESI) ion source. Mobile phase A was ammonium acetate 5 mM buffer (pH 5.2 with acetic acid)/acetonitrile 95/5, and Mobile phase B was water/acetonitrile 5/95. Gradient from 10 to 90% B in 8 minutes, hold 90% B 2 minutes. UV detection at 220 nm and 254 nm. Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass is given as m/z ratio. When necessary, compounds were purified by preparative HPLC on a Waters Symmetry C18 (19×50 mm, 5 µm) column or on a Waters X Terra RP 18 (30×150 mm, 5 µm) column using a Waters preparative HPLC 600 equipped with a 996 Waters PDA detector and a Waters mod. ZMD single quadrupole mass spectrometer, electron spray ionization, positive mode. Method 1: mobile phase A was water-0.1% trifluoroacetic acid/acetonitrile 95/5, and mobile phase B was acetonitrile; gradient from 10 to 90% B in 8 min, hold 90% B 2 min; flow rate 20 mL/min. Method 2: mobile phase A was water-0.05% NH$_3$/acetonitrile 95/5, and mobile phase B was acetonitrile. Gradient from 10 to 100% B in 8 min, hold 100% B 2 min. Flow rate 20 mL/min.

In the examples below as well as throughout the application, the following abbreviations have the following meanings. If not defined, the terms have their generally accepted meanings.

ABBREVIATIONS

AcOH acetic acid
CH₃CN acetonitrile
DCM dichloromethane
DIPEA N,N-diisopropyethylamine
DMF N,N-dimethylformamide
DMSO dimethyl sulfoxide
eq equivalents
ESI electrospray ionization
EtOAc ethyl acetate
EDCl N-ethyl-N',N'-diisopropyl carbodiimide hydrochloride
Et₂O diethyl ether
EtOH ethanol
g gram(s)
h hour(s)
HCl hydrochloric acid
HOBt 1H-benzotriazol-1-ol
HOBt.NH₃ 1H-benzotriazol-1-ol ammonium salt
HPLC high performance liquid chromatography
K₂CO₃ potassium carbonate
K₃PO₄ potassium phosphate
KOH potassium hydroxide
tBuOK potassium tert-butoxide
LiCl lithium chloride
M molar
MeOH methanol
MeNH₂ methylamine
mg milligram(s)
min minute(s)
mL milliliter(s)
mmol millimole(s)
mol mole(s)
N normal
Na₂CO₃ sodium carbonate
Na₂S₂O₅ sodium metabisulphite
Na₂SO₄ sodium sulfate
NaHCO₃ sodium hydrogen carbonate
NaOH sodium hydroxide
Pd(PPh₃)₂Cl₂ bis(triphenylphosphine)-palladium(II)chloride
PdCl₂(dppf) [1,1'-bis(diphenylphosphino)ferrocene]palladium(II) chloride
rt room temperature
TEA triethylamine
TFA trifluoroacetic acid
THF tetrahydrofurane
μL microliter(s)

Preparation A (5-Chloro-2-ethylphenyl)boronic acid (IIIa)

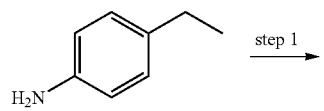

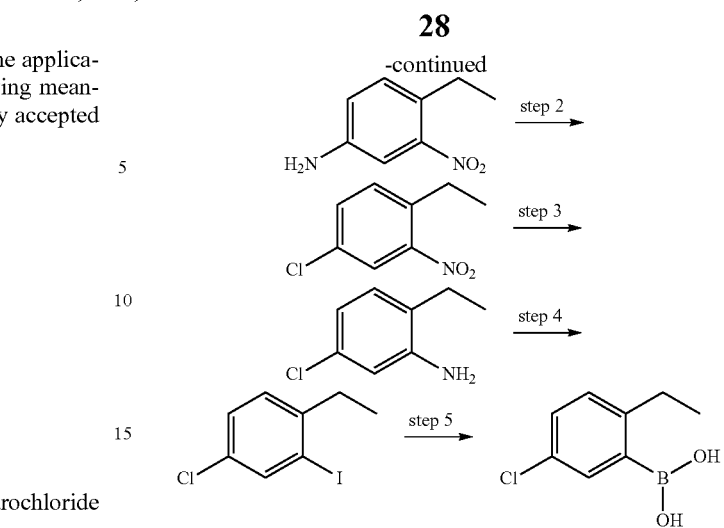

Step 1: 4-Ethyl-3-nitroaniline

4-Ethylaniline (10.3 mL, 82.5 mmol) was added drop wise to sulfuric acid (96%, 63 mL), cooled to 8° C., maintaining the temperature below 10° C. After the addition, the reaction mixture was cooled to −5° C., before the addition of a mixture of nitric acid (100%, 4 mL) and sulfuric acid (96%, 10 mL), keeping the temperature below 0° C. The reaction mixture was then stirred at the same temperature for 1 h. The reaction mixture was poured into ice (200 mL) and the precipitate filtered and washed with water. The solid was suspended with water (100 mL) and neutralized with ammonium hydroxide (35%). The precipitate was filtered and dried in the oven to obtain a light-brown solid (10 g, 73%).

¹H NMR (400 MHz, DMSO-d₆) δ ppm 1.11 (t, J=7.45 Hz, 3H), 2.63 (q, J=7.45 Hz, 2H), 5.53 (s, 2H), 6.81 (dd, J=8.30, 2.44 Hz, 1H), 7.04 (d, J=2.44 Hz, 1H), 7.11 (d, J=8.30 Hz, 1H).

Step 2: 4-Chloro-1-ethyl-2-nitrobenzene

A solution of sodium nitrite in water (4.2 g, 60 mmol, 5 M, 12 mL) was added drop wise to a cooled (0° C.) solution of 4-ethyl-3-nitroaniline (10 g, 60 mmol) in conc. HCl (200 mL) and the reaction mixture was stirred at the same temperature for 1.5 h. Copper (I) chloride (9.5 g, 96 mmol) was then added and the solution was stirred at room temperature for 1 h and then at 80° C. for an additional hour. After cooling down the reaction mixture was extracted with DCM (3×100 mL) and the combined organic layers were dried over sodium sulfate. The crude was then purified by flash chromatography (hexane/EtOAc 9/1) to obtain the title compound as a yellow oil (6.28 g, 56%).

¹H NMR (400 MHz, DMSO-d₆) δ ppm 1.19 (t, J=7.45 Hz, 3H), 2.78 (q, J=7.45 Hz, 2H), 7.57 (d, J=8.42 Hz, 1H), 7.74 (dd, J=8.36, 2.26 Hz, 1H), 8.03 (d, J=2.32 Hz, 1H).

Step 3: 5-Chloro-2-ethylaniline

A solution of hydrazine hydrate (6.95 mL, 134.7 mmol) in methanol (50 mL) was added drop wise to a solution of 4-chloro-1-ethyl-2-nitrobenzene (6.25 g, 33.7 mmol) in methanol (120 mL), in the presence of iron (III) chloride (547 mg, 3.4 mmol) and activated charcoal (547 mg) and the reaction mixture was stirred under reflux for 13 h. The solids were filtered over celite, the filtrate concentrated and purified by flash chromatography (hexane/EtOAc 9/1) to obtain the title compound as a light-pink oil (5.09 g, 97%).

¹H NMR (400 MHz, DMSO-d₆) δ ppm 1.09 (t, J=7.51 Hz, 3H), 2.39 (q, J=7.49 Hz, 2H), 5.13 (s, 2H), 6.47 (dd, J=8.06, 2.20 Hz, 1H), 6.62 (d, J=2.20 Hz, 1H), 6.89 (d, J=8.06 Hz, 1H).

Step 4: 4-Chloro-1-ethyl-2-iodobenzene

A mixture of 5-chloro-2-ethylaniline (3.35 g, 21.5 mmol), p-toluenesulfonic acid (12.29 g, 64.6 mmol) and water (2.15 mL) were ground in a mortar for few minutes, to obtain a homogeneous paste to which solid sodium nitrite (3.71 g, 53.8 mmol) was added and the paste ground for 10 min. Solid potassium iodide (8.94 g, 53.8 mmol) was added and the paste ground for 20 min. The paste was then dissolved in water (50 mL) and treated with sodium sulfite (10% aq. sol.), before being extracted with EtOAc (3×100 mL). The combined organic layers were dried over sodium sulfate and the crude was purified by flash chromatography (hexane) to obtain the title compound as a light-yellow oil (4.35 g, 76%).

¹H NMR (400 MHz, DMSO-d₆) δ ppm 1.12 (t, J=7.51 Hz, 3H), 2.66 (q, J=7.53 Hz, 2H), 7.29-7.35 (m, 1H), 7.42 (dd, J=8.30, 2.20 Hz, 1H), 7.87 (d, J=2.20 Hz, 1H).

Step 5: (5-Chloro-2-ethylphenyl)boronic acid i-Propylmagnesium chloride (2M sol. in THF, 8.98 mL, 17.95 mmol) was added drop wise to a solution of 4-chloro-1-ethyl-2-iodobenzene (4.35 g, 16.3 mmol) in dry THF (40 mL) at −30° C. and the reaction mixture was stirred at the same temperature for 30 min, under argon. After this time, trimethylborate (3.63 mL, 32.6 mmol) was added drop wise and the reaction mixture was stirred at the same temperature for 1.5 h. HCl (1 M, 16 mL) was added and the reaction mixture extracted with EtOAc (3×50 mL). The combined organic layers were dried over sodium sulfate and, after removal of the solvent, a solid was obtained, which was triturated with hexane to obtain the title compound as a white solid (2.15 g, 72%).

¹H NMR (400 MHz, DMSO-d₆) δ 1.12 ppm (t, J=7.51 Hz, 3H), 2.72 (q, J=7.69 Hz, 2H), 7.17 (d, J=8.18 Hz, 1H), 7.25-7.32 (m, 1H), 7.36 (d, J=2.32 Hz, 1H), 8.19 (s, 2H).

Preparation B

[5-Chloro-2-(propan-2-yl)phenyl]boronic acid (IIIa)

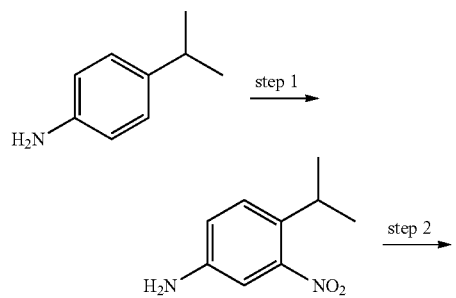

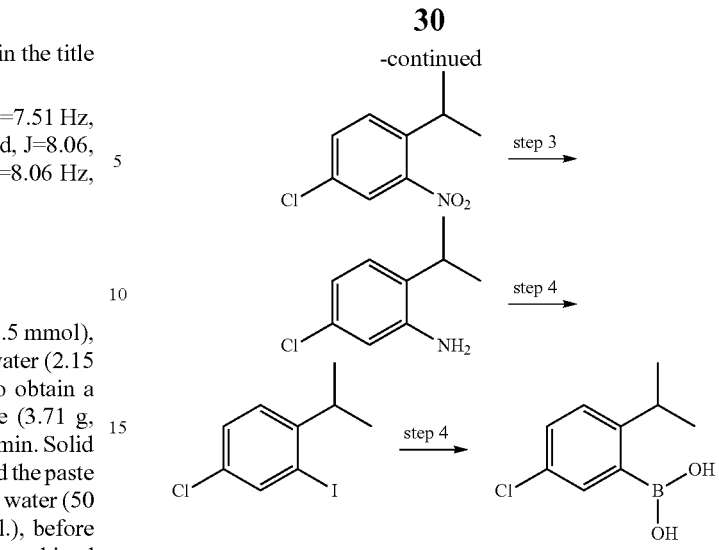

Step 1: 3-Nitro-4-(propan-2-yl)aniline 4-(Propan-2-yl)aniline (10.12 mL, 74 mmol) was added drop wise to sulfuric acid (96%, 57 mL), cooled to 8° C., maintaining the temperature below 10° C. After the addition, the reaction mixture was cooled to −5° C., before the addition of a mixture of nitric acid (100%, 3.7 mL) and sulfuric acid (96%, 9 mL), keeping the temperature below 0° C. The reaction mixture was then stirred at the same temperature for 1 h. The reaction mixture was poured into ice (200 mL) and the precipitate filtered and washed with water. The solid was suspended with water (100 mL) and neutralized with ammonium hydroxide (35%). The precipitate was filtered and dried in the oven to obtain a light-brown solid (9.49 g, 71%).

Step 2: 4-Chloro-2-nitro-1-(propan-2-yl)benzene

A solution of sodium nitrite in water (3.6 g, 52.2 mmol, 5 M, 10.4 mL) was added drop wise to a solution of 3-nitro-4-(propan-2-yl)aniline (9.4 g, 52.2 mmol) in conc. HCl (175 mL) at 0° C. and the reaction mixture was stirred at the same temperature for 1.5 h. Copper (I) chloride (8.3 g, 83.5 mmol) was then added and the solution was stirred at room temperature for 1 h and then at 80° C. for an additional hour. After cooling down the reaction mixture was extracted with DCM (3×100 mL) and the combined organic layers were dried over sodium sulfate. The crude was then purified by flash chromatography (hexane/EtOAc 95/5) to obtain the title compound as yellow oil (1.8 g, 17%).

¹H NMR (400 MHz, DMSO-d₆) δ ppm 1.23 (d, J=6.84 Hz, 6H), 3.14 (spt, J=6.94 Hz, 1H), 7.67 (d, J=8.54 Hz, 1H), 7.74 (dd, J=8.54, 2.30 Hz, 1H), 7.95 (d, J=2.20 Hz, 1H).

Step 3: 5-Chloro-2-(propan-2-yl)aniline

A solution of hydrazine hydrate (1.7 mL, 35.1 mmol) in methanol (12 mL) was added drop wise to a solution of 4-chloro-2-nitro-1-(propan-2-yl)benzene (1.75 g, 8.8 mmol) in methanol (40 mL), in the presence of iron (III) chloride (146 mg, 0.9 mmol) and activated charcoal (146 mg) and the reaction mixture was stirred under reflux for 7 h. The solid was filtered over celite, the filtrate concentrated and purified by flash chromatography (hexane/EtOAc 9/1) to obtain the title compound as a light-pink oil (1.4 g, 94%).

¹H NMR (400 MHz, DMSO-d₆) δ ppm 1.11 (d, J=6.84 Hz, 6H), 2.90 (spt, J=6.75 Hz, 1H), 5.15 (s, 2H), 6.50 (dd, J=8.18, 2.32 Hz, 1H), 6.62 (d, J=2.32 Hz, 1H), 6.96 (d, J=8.18 Hz, 1H).

Step 4: 4-Chloro-2-iodo-1-(propan-2-yl)benzene

A mixture of 5-chloro-2-(propan-2-yl)aniline (1.4 g, 8.3 mmol), p-toluenesulfonic acid (4.7 g, 24.8 mmol) and water (0.83 mmol) were ground in a mortar for few minutes, to obtain an homogeneous paste to which solid sodium nitrite (1.42 g, 20.6 mmol) was added and the paste ground for 10 min. Solid potassium iodide (3.42 g, 20.6 mmol) was added and the paste ground for 20 min. The paste was then dissolved in water (20 mL) and treated with sodium sulfite (10% aq. sol.), before being extracted with EtOAc (3×50 mL). The combined organic layers were dried over sodium sulfate and the crude was purified by flash chromatography (hexane) to obtain the title compound as a light-yellow oil (1.79 g, 77%).

¹H NMR (400 MHz, DMSO-d₆) δ ppm 1.17 (d, J=6.84 Hz, 6H), 3.08 (spt, J=6.88 Hz, 1H), 7.33 (d, J=8.42 Hz, 1H), 7.45 (ddd, J=8.42, 2.20, 0.37 Hz, 1H), 7.87 (d, J=2.20 Hz, 1H).

Step 5: [5-Chloro-2-(propan-2-yl)phenyl]boronic acid i-Propylmagnesium chloride (2 M in THF, 3.34 mL, 6.7 mmol) was added drop wise to a solution of 4-chloro-2-iodo-1-(propan-2-yl)benzene (1.7 g, 6.7 mmol) in dry THF (15 mL) at −30° C. and the reaction mixture was stirred at the same temperature for 30 min, under argon. After this time, trimethylborate (1.35 mL, 12.1 mmol) was added drop wise and the reaction mixture was stirred at the same temperature for 1.5 h. HCl (1 M, 6 mL) was added and the reaction mixture extracted with EtOAc (3×20 mL). The combined organic layers were dried over sodium sulfate and, after removal of the solvent, a solid was obtained, which was triturated with hexane to obtain the title compound as a white solid (1.05 g, 87%).

¹H NMR (400 MHz, DMSO-d₆) δ ppm 1.16 (d, J=6.84 Hz, 6H), 3.17-3.25 (m, 1H), 7.24-7.29 (m, 2H), 7.29-7.33 (m, 1H), 8.22 (s, 2H).

Preparation C

[2-Ethyl-5-(trifluoromethyl)phenyl]boronic acid (IIIa)

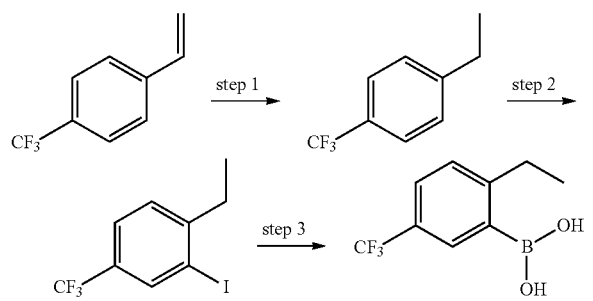

Step 1: 1-Ethyl-4-(trifluoromethyl)benzene

A solution of 1-ethenyl-4-(trifluoromethyl)benzene (1.72 mL, 11.6 mmol) in THF (60 mL) was stirred in the presence of Pd/C (10%, 400 mg), under a hydrogen atmosphere (45 psi) for 7 h. The solid was filtered through celite (washed with DCM) and the filtrate was carefully concentrated, keeping the temperature of the bath below 20° C. at 200 mmHg. The concentrated solution thus obtained was used in the next step without further manipulation.

¹H NMR (400 MHz, DMSO-d₆) δ ppm 1.20 (t, J=7.63 Hz, 3H), 2.70 (q, J=7.16 Hz, 2H), 7.44 (d, J=7.93 Hz, 2H), 7.63 (d, J=7.93 Hz, 2H).

Step 2: 2-Iodo-1-ethyl-4-(trifluoromethyl)benzene

Sulfuric acid (96%, 1.9 mL) was added drop wise to a solution of sodium periodate (3.73 g, 17.4 mmol) and iodine (2.95 g, 11.6 mmol) in a mixture acetic acid (8.45 mL) acetic anhydride (4.23 mL) at 0° C., followed by the drop wise addition of 1-ethyl-4-(trifluoromethyl)benzene (2.0 g, 11.6 mmol). The reaction mixture was let warming up to room temperature while stirring for a period of 24 h. A solution of sodium metabisulfite (10%) was added to quench the remaining iodine and successively, sodium hydroxide (35%) was added to reach pH=7. The aqueous layer was extracted with DCM (3×50 mL) and the combined organic layers were dried over sodium sulfate. Once the solvent was removed, the crude was used without further purification in the next step.

¹H NMR (400 MHz, DMSO-d₆) δ ppm 1.16 (t, J=7.51 Hz, 3H), 2.75 (q, J=7.49 Hz, 2H), 7.53 (d, J=8.06 Hz, 1H), 7.69-7.75 (m, 1H), 8.11 (dq, J=1.95, 0.73 Hz, 1H).

Step 3: [2-Ethyl-5-(trifluoromethyl)phenyl]boronic acid i-Propylmagnesium chloride (2M sol. in THF, 5.81 mL, 11.6 mmol) was added drop wise to a cooled (−30° C.) solution of 2-iodo-1-ethyl-4-(trifluoromethyl)benzene (3.48 g, 11.6 mmol) in dry THF (30 mL) and the reaction mixture was stirred at the same temperature for 30 min, under argon. After this time, trimethylborate (2.6 mL, 23.2 mmol) was added drop wise and the reaction mixture was stirred at the same temperature for 1.5 h. HCl (1 M, 10 mL) was added and the reaction mixture extracted with EtOAc (3×40 mL). The combined organic layers were dried over sodium sulfate and the solvent was evaporated to obtain the title compound as a white solid, crystallized from hexane (2.46 g, 97%).

¹H NMR (400 MHz, DMSO-d₆) δ ppm 1.16 (t, J=7.51 Hz, 3H), 2.82 (q, J=7.45 Hz, 2H), 7.37 (d, J=8.06 Hz, 1H), 7.56-7.62 (m, 1H), 7.69 (dq, J=1.80, 0.40 Hz, 1H), 8.27 (s, 2H).

Preparation D

Methyl 5-chloro-2-ethylbenzoate

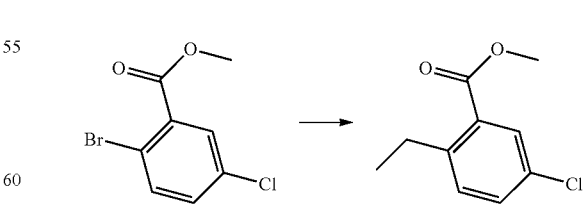

Methyl 2-bromo-5-chlorobenzoate (1.0 g, 4 mmol), lithium chloride (490 mg, 11.58 mmol), tetraethyltin (0.81 mL, 4.1 mmol) and bis(triphenylphosphine)-palladium(II) chloride (100 mg, 0.13 mmol) were combined in DMF (20 mL) and heated at 100° C. for 5 h. Solvent was removed at reduced pressure and the residue was diluted with water and EtOAc. The organic layer was separated, washed with water, dried over sodium sulfate and concentrated. Column chromatography on silica gel (0 to 10% EtOAc/hexane) provided the title compound (435 mg, 55%).

$^1$H NMR (400 MHz, DMSO-$d_6$) δ ppm 1.15 (t, J=7.43 Hz, 3H) 2.86 (q, J=7.45 Hz, 2H) 3.84 (s, 3H) 7.40 (d, J=8.30 Hz, 1H) 7.53-7.61 (m, 1H) 7.75 (d, J=2.32 Hz, 1H).

The above procedure was employed to synthesize the following compound:

Methyl 2-ethyl-5-(trifluromethyl)benzoate $^1$H NMR (600 MHz, DMSO-$d_6$) δ 1.18 (t, J=7.6 Hz, 3H) 2.97 (q, J=7.6 Hz, 2H) 3.87 (s, 3H) 7.62 (d, J=8.1 Hz, 1H) 7.88 (dd, J=1.5, 8.2 Hz, 1H) 8.04 (d, J=1.10 Hz, 1H), Preparation E 2-[2-Chloro-5-(trifluoromethyl)phenyl]-1H-pyrrole-3-carbonitrile [(VIII), R1=Cl, R2=CF$_3$]

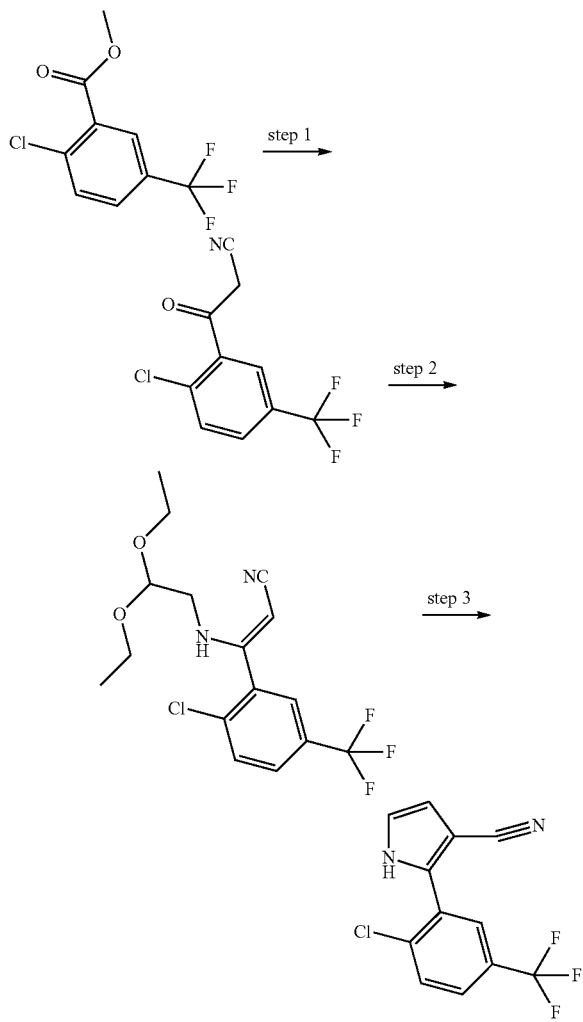

Step 1: 3-[2-Chloro-5-(trifluoromethyl)phenyl]-3-oxopropanenitrile

Potassium tert-pentoxide 1.7 M in toluene (7.35 mL, 12.5 mmol) was added drop wise to a solution of methyl 2-chloro-5-(trifluoromethyl)benzoate (2.0 g, 8.38 mmol) and ACN (1.32 mL, 25.15 mmol) in anhydrous toluene (30 mL). The mixture was stirred at room temperature for 20 min, then diluted with HCl 1 N (20 mL), water (75 mL) and EtOAc (100 mL). The organic layer was separated, washed with water (50 mL×2) and brine (50 mL×2), dried over sodium sulfate and concentrated. Column chromatography on silica gel (0 to 20% EtOAc/hexane) provided the title compound (1.73 g, 83%).

$^1$H NMR (400 MHz, DMSO-$d_6$) δ ppm 4.76 (s, 2H) 7.81-7.98 (m, 3H).

Step 2: 3-[2-Chloro-5-(trifluoromethyl)phenyl]-3-[(2,2-diethoxyethyl)amino]prop-2-enenitrile A mixture of 3-[2-chloro-5-(trifluoromethyl)phenyl]-3-oxopropanenitrile (1.2 g, 4.8 mmol), 2-aminoacetaldehyde diethyl acetal (0.77 mL, 5.3 mmol) and toluene (30 mL) was stirred under reflux for 5 h under nitrogen atmosphere in the Dean-Stark apparatus. The mixture was evaporated in vacuo and used in the next step without further purification.

Step 3: 2-(2-Chloro-5-trifluoromethyl-phenyl)-1H-pyrrole-3-carbonitrile

To TFA (4 mL) at 5° C. the crude 3-[2-chloro-5-(trifluoromethyl)phenyl]-3-[(2,2-diethoxyethyl)amino]prop-2-enenitrile was added. After stirring at room temperature for 30 min, the reaction mixture was concentrated and then diluted with EtOAc and saturated solution of sodium hydrogen carbonate. The organic layer was separated, washed with water and brine, dried over sodium sulfate and concentrated. Column chromatography on silica gel (0 to 20% EtOAc/hexane) afforded the title compound (584 mg, 45% 2 steps).

$^1$H NMR (400 MHz, DMSO-$d_6$) δ ppm 6.65 (t, J=2.62 Hz, 1H) 7.12 (t, J=2.81 Hz, 1H) 7.81-7.95 (m, 3H) 12.23 (bs, 1H).

The above procedure was employed to synthesize the following compounds:

2-(5-Chloro-2-methyl-phenyl)-1H-pyrrole-3-carbonitrile [(VIII), R1=CH$_3$, R2=Cl]

$^1$H NMR (400 MHz, DMSO-$d_6$) δ ppm 2.26 (s, 3H) 6.59 (t, J=2.69 Hz, 1H) 7.04 (t, J=2.81 Hz, 1H) 7.38 (d, J=2.20 Hz, 1H) 7.39-7.42 (m, 1H) 7.42-7.47 (m, 1H) 11.99 (bs, 1H).

2-(2-Bromo-5-chloro-phenyl)-1H-pyrrole-3-carbonitrile [(VIII), R1=Br, R2=Cl]

$^1$H NMR (400 MHz, DMSO-$d_6$) δ ppm 6.60 (t, J=2.62 Hz, 1H) 7.06 (t, J=2.81 Hz, 1H) 7.51 (dd, J=8.61, 2.62 Hz, 1H) 7.59 (d, J=2.56 Hz, 1H) 7.82 (d, J=8.54 Hz, 1H) 12.13 (bs, 1H).

2-(2,5-Dichloro-phenyl)-1H-pyrrole-3-carbonitrile [(VIII), R1=Cl, R2=Cl]

$^1$H NMR (400 MHz, DMSO-$d_6$) δ ppm 6.62 (t, J=2.62 Hz, 1H) 7.08 (t, J=2.81 Hz, 1H) 7.55-7.61 (m, 1H) 7.61-7.63 (m, 1H) 7.65-7.69 (m, 1H) 12.16 (bs, 1H).

2-(5-Chloro-2-ethylphenyl)-1H-pyrrole-3-carbonitrile [(VIII), R1=CH₂CH₃, R2=Cl]

¹H NMR (400 MHz, DMSO-d₆) δ ppm 0.99 (t, J=7.51 Hz, 3H) 2.58 (q, J=7.53 Hz, 2H) 6.58 (t, J=2.65 Hz, 1H) 7.02 (t, J=2.81 Hz, 1H) 7.31-7.37 (m, 1H) 7.41-7.46 (m, 1H) 7.47-7.52 (m, 1H) 11.99 (bs, 1H).

2-[2-Methyl-5-(trifluoromethyl)phenyl]-1H-pyrrole-3-carbonitrile [(VIII), R1=CH₃, R2=CF₃]

¹H NMR (400 MHz, DMSO-d₆) δ 2.36-2.39 (m, 3H) 6.62 (t, J=2.61 Hz, 1H) 7.08 (t, J=2.75 Hz, 1H) 7.62 (d, J=8.24 Hz, 1H) 7.65 (s, 1H) 7.74 (d, J=7.96 Hz, 1H) 12.08 (br. s., 1H).

2-[2-Ethyl-5-(trifluoromethyl)phenyl]-1H-pyrrole-3-carbonitrile [(VIII), R1=CH₂CH₃, R2=CF₃]

¹H NMR (400 MHz, DMSO-d₆) δ ppm 1.04 (t, J=7.51 Hz, 3H) 1.11-1.52 (m, 1H) 2.07 (s, 1H) 2.69 (q, J=7.51 Hz, 2H) 6.61 (t, J=2.75 Hz, 1H) 7.06 (t, J=2.75 Hz, 1H) 7.61 (s, 1H) 7.66 (d, J=8.24 Hz, 1H) 7.79 (dd, J=1.46, 8.06 Hz, 1H) 12.05 (bs, 1H).

Example 1

5-(2-Aminopyrimidin-4-yl)-2-[2-chloro-5-(trifluoromethyl)phenyl]-1H-pyrrole-3-carboxamide [(I), R1=Cl, R2=CF₃, R3=R4=NH₂, R12=H] (compd. 1)

Scheme A, steps 1, 2, 3

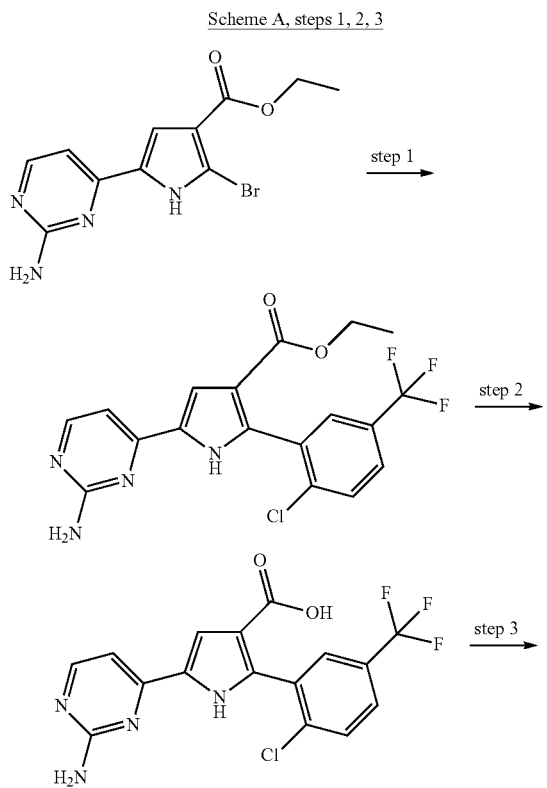

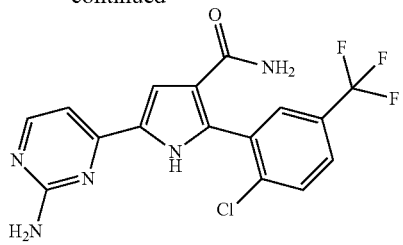

Step 1: Ethyl 5-(2-aminopyrimidin-4-yl)-2-[2-chloro-5-(trifluoromethyl)phenyl]-1H-pyrrole-3-carboxylate To a solution of ethyl 5-(2-aminopyrimidin-4-yl)-2-bromo-1H-pyrrole-3-carboxylate (prepared according to WO2007/110344, 2.0 g, 6.43 mmol) dissolved in EtOH (20 mL) and toluene (20 mL), LiCl (408 mg, 9.64 mmol), 1 M aq Na₂CO₃ (17 mmol), 2-chloro-5-trifluoromethylphenylboronic acid (1.875 g, 8.35 mmol) and (Ph₃P)₂PdCl₂ (470 mg, 0.67 mmol) were added and the reaction mixture was heated at 100° C. for 5 h. After cooling to room temperature, the precipitate was filtered and the filtrate was evaporated under reduced pressure, dissolved in DCM and washed with water. The organic layer was then dried over sodium sulfate and concentrated. The crude material was chromatographed on silica gel (DCM/EtOAc 50/50) to afford the title compound (2.16 g, 82%).

¹H NMR (400 MHz, DMSO-d₆) δ ppm 1.01 (t, J=7.08 Hz, 3H) 4.00 (q, J=7.08 Hz, 2H) 6.39 (bs, 2H) 6.99 (d, J=5.25 Hz, 1H) 7.29 (d, J=2.32 Hz, 3H) 7.82 (s, 4H) 8.20 (d, J=5.13 Hz, 3H) 12.36 (bs, 1H).

HRMS (ESI) calcd for $C_{18}H_{14}ClF_3N_4O_2+H^+$ 411.0830. found 411.0827.

The above procedure was employed to synthesize the following compounds:

Ethyl 5-(2-aminopyrimidin-4-yl)-2-(5-chloro-2-methyl phenyl)-1H-pyrrole-3-carboxylate ¹H NMR (400 MHz, DMSO-d₆) δ ppm 1.09 (t, J=7.14 Hz, 3H) 2.11 (s, 3H) 4.04 (q, J=7.12 Hz, 2H) 6.41 (s, 2H) 7.01 (d, J=5.25 Hz, 1H) 7.25-7.36 (m, 3H) 7.37-7.43 (m, 1H) 8.21 (d, J=5.13 Hz, 1H) 12.17 (bs, 1H).

Ethyl 5-(2-aminopyrimidin-4-yl)-2-(2,5-dichlorophenyl)-1H-pyrrole-3-carboxylate ¹H NMR (400 MHz, DMSO-d₆) δ ppm 1.07 (t, J=7.08 Hz, 3H) 4.05 (q, J=7.16 Hz, 2H) 6.42 (bs, 2H) 7.01 (d, J=5.25 Hz, 1H) 7.29 (s, 1H) 7.52-7.60 (m, 3H) 8.22 (d, J=5.25 Hz, 1H) 12.32 (bs, 1H).

Ethyl 5-(2-aminopyrimidin-4-yl)-2-(5-chloro-2-methoxyphenyl)-1H-pyrrole-3-carboxylate ¹H NMR (400 MHz, DMSO-d₆) δ ppm 1.11 (t, J=7.08 Hz, 3H) 3.73 (s, 3H) 4.05 (q, J=7.16 Hz, 2H) 6.43 (bs, 2H) 7.01 (d, J=5.25 Hz, 1H) 7.11 (d, J=8.91 Hz, 1H) 7.26 (d, J=2.69 Hz, 1H) 7.38 (d, J=2.69 Hz, 1H) 7.45 (dd, J=8.85, 2.75 Hz, 1H) 8.20 (d, J=5.25 Hz, 1H) 12.01 (bs, 1H).

Ethyl 5-(2-aminopyrimidin-4-yl)-2-(5-chloro-2-ethylphenyl)-1H-pyrrole-3-carboxylate ¹H NMR (400 MHz, DMSO-d₆) δ ppm 0.97 (t, J=7.57 Hz, 3H) 1.06 (t, J=7.08 Hz, 3H) 2.44 (q, J=7.57 Hz, 2H) 4.03 (q, J=7.08 Hz, 2H) 7.21 (d, J=6.10 Hz, 1H) 7.32 (d, J=2.32 Hz, 1H) 7.38 (d, J=8.42 Hz, 1H) 7.47 (dd, J=8.30, 2.32 Hz, 1H) 7.50 (d, J=2.56 Hz, 1H) 8.25 (d, J=5.98 Hz, 1H) 12.52 (bs, 1H).

Ethyl 5-(2-aminopyrimidin-4-yl)-2-(2-chloro-5-methylphenyl)-1H-pyrrole-3-carboxylate $^1$H NMR (400 MHz, DMSO-$d_6$) δ ppm 1.06 (t, J=7.14 Hz, 3H) 2.34 (s, 3H) 4.03 (q, J=7.16 Hz, 2H) 6.41 (s, 1H) 7.01 (d, J=5.25 Hz, 1H) 7.27-7.30 (m, 3H) 7.42 (d, J=8.06 Hz, 1H) 8.21 (d, J=5.25 Hz, 1H) 12.20 (bs, 1H).

Ethyl 5-(2-aminopyrimidin-4-yl)-2-(5-bromo-2-methoxyphenyl)-1H-pyrrole-3-carboxylate $^1$H NMR (400 MHz, DMSO-$d_6$) δ ppm 1.11 (t, J=7.08 Hz, 3H) 3.72 (s, 3H) 4.05 (q, J=7.16 Hz, 2H) 6.41 (s, 2H) 7.01 (d, J=5.25 Hz, 1H) 7.06 (d, J=8.91 Hz, 1H) 7.25 (d, J=2.69 Hz, 1H) 7.49 (d, J=2.56 Hz, 1H) 7.57 (dd, J=8.85, 2.62 Hz, 1H) 8.20 (d, J=5.25 Hz, 1H) 12.01 (bs, 1H).

Ethyl 5-(2-aminopyrimidin-4-yl)-2-(5-bromo-2-fluorophenyl)-1H-pyrrole-3-carboxylate $^1$H NMR (400 MHz, DMSO-$d_6$) δ ppm 1.13 (t, J=7.08 Hz, 3H) 4.09 (q, J=7.16 Hz, 2H) 6.44 (bs, 2H) 7.03 (d, J=5.13 Hz, 1H) 7.29 (dd, J=9.28, 8.91 Hz, 1H) 7.31 (d, J=2.32 Hz, 1H) 7.63-7.69 (m, 2H) 7.72 (dd, J=6.47, 2.56 Hz, 1H) 8.23 (d, J=5.25 Hz, 1H) 12.33 (bs, 1H).

Ethyl 5-(2-aminopyrimidin-4-yl)-2-([2-chloro-5-(hydroxymethyl)phenyl]-1H-pyrrole-3-carboxylate $^1$H NMR (400 MHz, DMSO-$d_6$) δ ppm 1.07 (t, J=7.08 Hz, 3H) 4.04 (q, J=7.08 Hz, 2H) 4.55 (s, 2H) 7.22 (d, J=5.98 Hz, 1H)) 7.38-7.55 (m, 4H) 8.26 (d, J=5.98 Hz, 1H) 12.55 (bs, 1H).

Ethyl 5-(2-aminopyrimidin-4-yl)-2-(2-chloro-5-methoxyphenyl)-1H-pyrrole-3-carboxylate $^1$H NMR (400 MHz, DMSO-$d_6$) δ ppm 1.07 (t, J=7.14 Hz, 3H) 3.79 (s, 3H) 4.04 (q, J=7.08 Hz, 2H) 6.41 (s, 2H) 7.02 (d, J=5.25 Hz, 1H) 7.03-7.06 (m, 2H) 7.28 (d, J=2.56 Hz, 1H) 7.41-7.46 (m, 1H) 8.21 (d, J=5.25 Hz, 1H) 12.22 (bs, 1H).

Ethyl 5-(2-aminopyrimidin-4-yl)-2-[2-chloro-5-(trifluoromethoxy)phenyl]-1H-pyrrole-3-carboxylate $^1$H NMR (400 MHz, DMSO-$d_6$) δ ppm 1.04 (t, J=7.08 Hz, 3H) 4.03 (q, J=7.08 Hz, 2H) 6.42 (bs, 2H) 7.01 (d, J=5.13 Hz, 1H) 7.30 (d, J=2.32 Hz, 1H) 7.46-7.54 (m, 2H) 7.68-7.72 (m, 1H) 8.22 (d, J=5.25 Hz, 1H) 12.37 (bs, 1H).

Ethyl 5-(2-aminopyrimidin-4-yl)-2-[2-methyl-5-(trifluoromethyl)phenyl]-1H-pyrrole-3-carboxylate $^1$H NMR (400 MHz, DMSO-$d_6$) δ ppm 1.04 (t, J=7.14 Hz, 3H) 2.21 (s, 3H) 4.02 (q, J=7.04 Hz, 2H) 6.41 (s, 2H) 7.01 (d, J=5.25 Hz, 1H) 7.32 (d, J=2.44 Hz, 1H) 7.54 (d, J=8.06 Hz, 1H) 7.59 (d, J=1.46 Hz, 1H) 7.70 (dd, J=8.06, 1.46 Hz, 1H) 8.21 (d, J=5.25 Hz, 1H) 12.24 (bs, 1H).

Ethyl 5-(2-aminopyrimidin-4-yl)-2-[5-chloro-2-(propan-2-yl)phenyl]-1H-pyrrole-3-carboxylate $^1$H NMR (400 MHz, DMSO-$d_6$) δ ppm 1.02 (t, J=7.08 Hz, 3H) 1.07 (d, J=6.96 Hz, 6H) 2.71 (spt, J=6.84 Hz, 1H) 4.00 (q, J=7.08 Hz, 2H) 6.40 (bs, 2H) 7.00 (d, J=5.13 Hz, 1H) 7.25 (d, J=2.32 Hz, 1H) 7.28 (d, J=2.56 Hz, 1H) 7.42 (d, J=8.30 Hz, 1H) 7.48 (dd, J=8.30, 2.32 Hz, 1H) 8.20 (d, J=5.25 Hz, 1H) 12.23 (bs, 1H).

Ethyl 5-(2-aminopyrimidin-4-yl)-2-[2-ethyl-5-(trifluoromethyl)phenyl]-1H-pyrrole-3-carboxylate $^1$H NMR (400 MHz, DMSO-$d_6$) δ ppm 1.01 (t, J=7.15 Hz, 6H) 2.54 (q, J=7.60 Hz, 2H) 4.00 (q, J=7.08 Hz, 2H) 6.41 (bs, 2H) 7.01 (d, J=5.25 Hz, 1H) 7.31 (d, J=2.56 Hz, 1H) 7.56 (d, J=1.60 Hz, 1H) 7.58 (d, J=8.20 Hz, 1H) 7.74 (dd, J=8.12, 1.53 Hz, 1H) 8.21 (d, J=5.13 Hz, 1H) 12.27 (bs, 1H).

Ethyl 5-(2-aminopyrimidin-4-yl)-2-[5-chloro-2-(trifluoromethyl)phenyl]-1H-pyrrole-3-carboxylate $^1$H NMR (400 MHz, DMSO-$d_6$) δ ppm 0.97 (t, J=7.08 Hz, 3H) 3.97 (q, J=7.08 Hz, 2H) 6.41 (bs, 2H) 6.99 (d, J=5.25 Hz, 1H) 7.27 (d, J=2.44 Hz, 1H) 7.66 (d, J=2.07 Hz, 1H) 7.74-7.79 (m, 1H) 7.86 (d, J=8.54 Hz, 1H) 8.21 (d, J=5.13 Hz, 1H) 12.37 (bs, 1H).

Ethyl 5-(2-aminopyrimidin-4-yl)-2-(5-cyano-2-methylphenyl)-1H-pyrrole-3-carboxylate $^1$H NMR (400 MHz, DMSO-$d_6$) δ ppm 1.07 (t, J=7.14 Hz, 3H) 2.21 (s, 3H) 4.04 (q, J=7.08 Hz, 2H) 6.41 (bs, 2H) 7.01 (d, J=5.25 Hz, 1H) 7.32 (d, J=2.32 Hz, 1H) 7.52 (d, J=8.06 Hz, 1H) 7.76 (d, J=1.83 Hz, 1H) 7.80 (dd, J=7.87, 1.77 Hz, 1H) 8.22 (d, J=5.25 Hz, 1H) 12.24 (bs, 1H).

Step 2: 5-(2-Aminopyrimidin-4-yl)-2-[2-chloro-5-(trifluoromethyl)phenyl]-1H-pyrrole-3-carboxylic acid Ethyl 5-(2-aminopyrimidin-4-yl)-2-[2-chloro-5-(trifluoromethyl)phenyl]-1H-pyrrole-3-carboxylate (1.0 g, 2.43 mmol) was treated with a 1.5 M solution of potassium hydroxide in 95% EtOH (32.4 mL, 20 eq) under reflux for 20 h. After cooling, the residue was concentrated, dissolved in water and washed with DCM. To the aqueous phase cooled to 5° C., a solution of HCl 2 N was added, under agitation. The resulting precipitate was collected by filtration to give the title compound (0.88 g, 95%).

$^1$H NMR (400 MHz, DMSO-$d_6$) δ ppm 7.29 (d, J=6.35 Hz, 1H) 7.62 (bs, 2H) 7.58 (d, J=2.20 Hz, 1H) 7.79-7.92 (m, 3H) 8.29 (d, J=6.23 Hz, 1H) 12.67 (bs, 1H) 12.76 (bs, 1H).

HRMS (ESI) calcd for $C_{16}H_{10}ClF_3N_4O_2$+H$^+$ 383.0517. found 383.0513.

The above procedure was employed to synthesize the following compounds:

5-(2-Aminopyrimidin-4-yl)-2-(5-chloro-2-methylphenyl)-1H-pyrrole-3-carboxylic acid $^1$H NMR (400 MHz, DMSO-$d_6$) δ ppm 2.12 (s, 3H) 7.28-7.37 (m, 3H) 7.40-7.45 (m, 1H) 7.59 (d, J=2.56 Hz, 1H) 7.77 (bs, 1H) 8.28 (d, J=6.44 Hz, 1H) 12.06 (s, 1H) 12.54 (bs, 1H).

5-(2-Aminopyrimidin-4-yl)-2-(5-chloro-2-ethylphenyl)-1H-pyrrole-3-carboxylic acid $^1$H NMR (400 MHz, DMSO-$d_6$) δ ppm 0.98 (t, J=7.57 Hz, 3H) 2.46 (q, J=7.57 Hz, 2H) 6.79 (bs, 2H) 7.08 (d, J=5.49 Hz, 1H) 7.29 (d, J=2.32 Hz, 1H) 7.35 (d, J=8.30 Hz, 1H) 7.36 (d, J=2.81 Hz, 1H) 7.43 (dd, J=8.30, 2.32 Hz, 1H) 8.22 (d, J=5.62 Hz, 1H) 11.86 (bs, 1H) 12.23 (bs, 1H).

5-(2-Aminopyrimidin-4-yl)-2-(2-chloro-5-methylphenyl)-1H-pyrrole-3-carboxylic acid $^1$H NMR (400 MHz, DMSO-$d_6$) δ ppm 2.33 (s, 3H) 6.88 (bs, 1H) 7.11 (d, J=5.61 Hz, 1H) 7.24-7.30 (m, 2H) 7.29 (dq, J=2.20, 0.60 Hz, 1H) 7.37 (d, J=2.20 Hz, 1H) 7.41 (d, J=8.06 Hz, 1H) 8.22 (d, J=5.62 Hz, 1H) 11.84 (bs, 1H) 12.26 (bs, 1H).

5-(2-Aminopyrimidin-4-yl)-2-(5-bromo-2-methoxyphenyl)-1H-pyrrole-3-carboxylic acid $^1$H NMR (400 MHz, DMSO-$d_6$) δ ppm 3.73 (s, 3H) 7.09 (d, J=8.91 Hz, 1H) 7.31 (d, J=6.59 Hz, 1H) 7.51 (d, J=2.56 Hz, 1H) 7.56 (d, J=2.32 Hz, 1H) 7.59 (dd, J=8.85, 2.62 Hz, 1H) 7.81 (bs, 2H) 8.27 (d, J=6.47 Hz, 1H) 12.41 (bs, 1H).

5-(2-Aminopyrimidin-4-yl)-2-(5-bromo-2-fluorophenyl)-1H-pyrrole-3-carboxylic acid $^1$H NMR (400 MHz, DMSO-$d_6$) δ ppm 7.27 (d, J=6.10 Hz, 1H) 7.30 (t, J=9.10 Hz, 1H) 7.53 (bs, 1H) 7.68 (ddd, J=8.88, 4.49, 2.62 Hz, 1H) 7.73 (dd, J=6.35, 2.56 Hz, 1H) 8.29 (d, J=6.10 Hz, 1H) 12.59 (bs, 1H).

5-(2-Aminopyrimidin-4-yl)-2-[2-chloro-5-(trifluoromethoxy)phenyl]-1H-pyrrole-3-carboxylic acid $^1$H NMR (400 MHz, DMSO-$d_6$) δ ppm 7.27 (d, J=6.47 Hz, 1H) 7.47-7.57 (m, 3H) 7.71 (d, J=9.03 Hz, 1H) 8.29 (d, J=6.23 Hz, 1H) 12.06 (s, 1H) 12.65 (bs, 1H).

5-(2-Aminopyrimidin-4-yl)-2-[2-methyl-5-(trifluoromethyl)phenyl]-1H-pyrrole-3-carboxylic acid $^1$H NMR (400 MHz, DMSO-$d_6$) δ ppm 2.23 (s, 3H) 7.28 (d, J=6.10 Hz, 1H) 7.55 (d, J=8.30 Hz, 1H) 7.58 (d, J=1.80 Hz, 1H) 7.61 (d, J=1.34 Hz, 1H) 7.71 (dd, J=8.18, 1.60 Hz, 1H) 8.27 (d, J=6.22 Hz, 1H) 12.54 (bs, 1H).

5-(2-Aminopyrimidin-4-yl)-2-[2-ethyl-5-(trifluoromethyl)phenyl]-1H-pyrrole-3-carboxylic acid $^1$H NMR (400 MHz, DMSO-$d_6$) δ ppm 1.02 (t, J=7.57 Hz, 3H) 2.56 (q, J=7.65 Hz, 2H) 7.18 (d, J=5.86 Hz, 1H) 7.20 (bs, 2H) 7.48 (d, J=2.44 Hz, 1H) 7.57 (bs, 1H) 7.58 (d, J=8.00 Hz, 1H) 7.74 (dd, J=7.99, 1.65 Hz, 1H) 8.25 (d, J=5.98 Hz, 1H) 11.95 (bs, 1H) 12.43 (bs, 1H).

Step 3: 5-(2-Aminopyrimidin-4-yl)-2-[2-chloro-5-(trifluoromethyl)phenyl]-1H-pyrrole-3-carboxamide [(I), R1=Cl, R2=CF$_3$, R3=R4=NH$_2$, R12=H] (compd. 1)

A solution of 5-(2-amino-pyrimidin-4-yl)-2-(2-chloro-5-trifluoromethyl-phenyl)-1H-pyrrole-3-carboxylic acid (581 mg, 1.52 mmol) in DMF (5 mL) and DIPEA (1.06 mL, 6.08 mmol) was stirred at 0° C. EDCI (582 mg, 3.04 mmol) and HOBT.NH$_3$ (469 mg, 3.04 mmol) were added and the reaction mixture was stirred for 3 h at room temperature. The mixture was diluted with water and the resulting precipitate was collected by filtration to afford the title compound (475 mg, 82%).

$^1$H NMR (400 MHz, DMSO-$d_6$) δ ppm 6.36 (bs, 2H) 6.77 (bs, 1H) 6.90 (d, J=5.25 Hz, 1H) 7.37 (d, J=2.56 Hz, 1H) 7.42 (bs, 1H) 7.69-7.84 (m, 3H) 8.22 (d, J=5.25 Hz, 1H) 12.07 (bs, 1H).

HRMS (ESI) calcd for $C_{16}H_{11}ClF_3N_5O+H^+$ 382.0677. found 382.0675.

The above procedure was employed to synthesize the following compounds:

5-(2-Aminopyrimidin-4-yl)-2-(2,5-dichlorophenyl)-1H-pyrrole-3-carboxamide [(I), R1=Cl, R2=Cl, R3=R4=NH$_2$, R12=H] (compd. 2)

$^1$H NMR (400 MHz, DMSO-$d_6$) δ ppm 6.87 (bs, 1H) 7.09 (d, J=6.10 Hz, 1H) 7.46 (bs, 1H) 7.48-7.56 (m, 3H) 8.26 (d, J=6.10 Hz, 1H) 12.35 (bs, 1H).

HRMS (ESI) calcd for $C_{15}H_{11}Cl_2N_5O+H^+$ 348.0414. found 348.0419.

5-(2-Aminopyrimidin-4-yl)-2-(5-chloro-2-methoxyphenyl)-1H-pyrrole-3-carboxamide [(I), R1=OCH$_3$, R2=Cl, R3=R4=NH$_2$, R12=H] (compd. 3)

$^1$H NMR (400 MHz, DMSO-$d_6$) δ ppm 3.75 (s, 3H) 6.35 (bs, 2H) 6.74 (bs, 1H) 6.92 (d, J=5.25 Hz, 1H) 7.08-7.12 (m, 1H) 7.20 (bs, 1H) 7.25 (d, J=2.56 Hz, 1H) 7.36-7.41 (m, 2H) 8.19 (d, J=5.25 Hz, 1H) 11.63 (bs, 1H).

HRMS (ESI) calcd for $C_{16}H_{14}ClN_5O_2+H^+$ 344.0909. found 344.0912.

5-(2-Aminopyrimidin-4-yl)-2-(2-chloro-5-ethylphenyl)-1H-pyrrole-3-carboxamide [(I), R1=Cl, R2=CH$_2$CH$_3$, R3=R4=NH$_2$, R12=H] (compd. 4)

$^1$H NMR (400 MHz, DMSO-$d_6$) δ ppm 1.20 (t, J=7.57 Hz, 3H) 2.63 (q, J=7.57 Hz, 2H) 6.33 (bs, 2H) 6.69 (bs, 1H) 6.93 (d, J=5.25 Hz, 1H) 7.14 (bs, 1H) 7.27 (d, J=2.20 Hz, 1H) 7.26 (dd, J=7.90, 2.20 Hz, 1H) 7.32 (d, J=2.56 Hz, 2H) 7.40 (dd, J=7.81, 0.49 Hz, 1H) 8.19 (d, J=5.25 Hz, 1H) 11.87 (bs, 1H).

HRMS (ESI) calcd for $C_{17}H_{16}ClN_5O+H^+$ 342.1116. found 342.1120.

5-(2-Aminopyrimidin-4-yl)-2-(5-chloro-2-ethylphenyl)-1H-pyrrole-3-carboxamide [(I), R1=CH$_2$CH$_3$, R2=Cl, R3=R4=NH$_2$, R12=H] (compd. 5)

$^1$H NMR (400 MHz, DMSO-$d_6$) δ ppm 0.97 (t, J=7.57 Hz, 3H) 2.41-2.49 (m, 2H) 6.32 (bs, 2H) 6.71 (bs, 1H) 6.92 (d, J=5.25 Hz, 1H) 7.16 (bs, 1H) 7.25 (d, J=2.20 Hz, 1H) 7.30-7.33 (m, 1H) 7.34 (d, J=2.69 Hz, 1H) 7.37-7.46 (m, 1H) 8.19 (d, J=5.25 Hz, 1H) 11.87 (bs, 1H).

HRMS (ESI) calcd for $C_{17}H_{16}ClN_5O+H^+$ 342.1116. found 342.1111.

5-(2-Aminopyrimidin-4-yl)-2-(2-chloro-5-methylphenyl)-1H-pyrrole-3-carboxamide [(I), R1=Cl, R2=CH$_3$, R3=R4=NH$_2$, R12=H] (compd. 6)

$^1$H NMR (400 MHz, DMSO-$d_6$) δ ppm 2.32 (s, 3H) 6.33 (bs, 2H) 6.68 (bs, 1H) 6.93 (d, J=5.25 Hz, 1H) 7.14 (bs, 1H) 7.20-7.24 (m, 1H) 7.25 (dq, J=2.20, 0.60 Hz, 1H) 7.31 (d, J=2.56 Hz, 1H) 7.38 (d, J=8.18 Hz, 1H) 8.19 (d, J=5.25 Hz, 1H) 11.85 (bs, 1H).

HRMS (ESI) calcd for $C_{16}H_{14}ClN_5O+H^+$ 328.0960. found 328.0965.

5-(2-Aminopyrimidin-4-yl)-2-(2-chloro-5-cyanophenyl)-1H-pyrrole-3-carboxamide [(I), R1=Cl, R2=CN, R3=R4=NH$_2$, R12=H] (compd. 7)

$^1$H NMR (400 MHz, DMSO-d$_6$) δ ppm 6.42 (bs, 2H) 6.79 (bs, 1H) 6.90 (d, J=5.25 Hz, 1H) 7.38 (d, J=2.56 Hz, 1H) 7.44 (bs, 1H) 7.73 (d, J=8.42 Hz, 1H) 7.88 (dd, J=8.42, 2.07 Hz, 1H) 7.94 (d, J=2.07 Hz, 1H) 8.23 (d, J=5.37 Hz, 1H) 12.07 (bs, 1H).
HRMS (ESI) calcd for C$_{16}$H$_{11}$ClN$_6$O+H$^+$ 339.0756. found 339.0761.

5-(2-Aminopyrimidin-4-yl)-2-(5-bromo-2-methoxyphenyl)-1H-pyrrole-3-carboxamide [(I), R1=OCH$_3$, R2=Br, R3=R4=NH$_2$, R12=H] (compd. 8)

$^1$H NMR (400 MHz, DMSO-d$_6$) δ ppm 3.74 (s, 3H) 6.36 (bs, 2H) 6.86 (bs, 1H) 7.07 (d, J=8.91 Hz, 1H) 7.14 (d, J=6.23 Hz, 1H) 7.29 (bs, 1H) 7.47 (d, J=2.44 Hz, 1H) 7.51 (d, J=2.56 Hz, 1H) 7.55 (dd, J=8.79, 2.56 Hz, 1H) 8.23 (d, J=6.23 Hz, 1H) 12.05 (bs, 1H).
HRMS (ESI) calcd for C$_{16}$H$_{14}$BrN$_5$O$_2$+H$^+$ 388.0404. found 388.0410.

5-(2-Aminopyrimidin-4-yl)-2-(5-bromo-2-fluorophenyl)-1H-pyrrole-3-carboxamide [(I), R1=F, R2=Br, R3=R4=NH$_2$, R12=H] (compd. 9)

$^1$H NMR (400 MHz, DMSO-d$_6$) δ ppm 6.46 (bs, 2H) 6.91 (bs, 1H) 7.11 (d, J=6.10 Hz, 1H) 7.25 (dd, J=9.46, 8.97 Hz, 1H) 7.33 (bs, 1H) 7.51 (d, J=2.32 Hz, 2H) 7.63 (ddd, J=8.76, 4.49, 2.62 Hz, 1H) 7.69 (dd, J=6.47, 2.56 Hz, 1H) 8.27 (d, J=5.98 Hz, 1H) 12.31 (bs, 1H).
HRMS (ESI) calcd for C$_{15}$H$_{11}$BrFN$_5$O+H$^+$ 376.0204. found 376.0209.

5-(2-Aminopyrimidin-4-yl)-2-[2-chloro-5-(hydroxymethyl)phenyl]-1H-pyrrole-3-carboxamide [(I), R1=Cl, R2=CH$_2$OH, R3=R4=NH$_2$, R12=H] (compd. 10)

$^1$H NMR (400 MHz, DMSO-d$_6$) δ ppm 4.53 (d, J=5.74 Hz, 2H) 5.33 (t, J=5.68 Hz, 1H) 6.33 (bs, 2H) 6.68 (bs, 1H) 6.93 (d, J=5.25 Hz, 1H) 7.15 (bs, 1H) 7.32 (d, J=2.56 Hz, 1H) 7.33-7.37 (m, 2H) 7.45 (d, J=8.80 Hz, 1H) 8.19 (d, J=5.25 Hz, 1H) 11.88 (bs, 1H).
HRMS (ESI) calcd for C$_{16}$H$_{14}$ClN$_5$O$_2$+H$^+$ 344.0909. found 344.0902.

5-(2-Aminopyrimidin-4-yl)-2-(2-chloro-5-methoxyphenyl)-1H-pyrrole-3-carboxamide [(I), R1=Cl, R2=OCH$_3$, R3=R4=NH$_2$, R12=H] (compd. 11)

$^1$H NMR (400 MHz, DMSO-d$_6$) δ ppm 3.78 (s, 3H) 6.33 (s, 2H) 6.70 (bs, 1H) 6.93 (d, J=5.25 Hz, 1H) 6.97-7.02 (m, 2H) 7.15 (bs, 1H) 7.31 (d, J=2.56 Hz, 1H) 7.36-7.42 (m, 1H) 8.19 (d, J=5.25 Hz, 1H) 11.88 (bs, 1H).
HRMS (ESI) calcd for C$_{16}$H$_{14}$ClN$_5$O$_2$+H$^+$ 344.0909. found 344.0907.

5-(2-Aminopyrimidin-4-yl)-2-[2-chloro-5-(trifluoromethoxy)phenyl]-1H-pyrrole-3-carboxamide [(I), R1=Cl, R2=OCF$_3$, R3=R4=NH$_2$, R12=H] (compd. 12)

$^1$H NMR (400 MHz, DMSO-d$_6$) δ ppm 6.35 (bs, 2H) 6.76 (bs, 1H) 6.90 (d, J=5.13 Hz, 1H) 7.35 (d, J=2.56 Hz, 1H) 7.39 (bs, 1H) 7.41-7.46 (m, 1H) 7.42 (dq, J=1.74, 0.90 Hz, 1H) 7.64 (ddd, J=8.79, 1.46, 1.10 Hz, 1H) 8.21 (d, J=5.25 Hz, 1H) 12.04 (bs, 1H).
HRMS (ESI) calcd for C$_{16}$H$_{11}$ClF$_3$N$_5$O$_2$+H$^+$ 398.0626. found 398.0624.

5-(2-Aminopyrimidin-4-yl)-2-[2-methyl-5-(trifluoromethyl)phenyl]-1H-pyrrole-3-carboxamide [(I), R1=CH$_3$, R2=CF$_3$, R3=R4=NH$_2$, R12=H] (compd. 13)

$^1$H NMR (400 MHz, DMSO-d$_6$) δ ppm 2.23 (s, 3H) 6.32 (bs, 2H) 6.74 (bs, 1H) 6.92 (d, J=5.25 Hz, 1H) 7.32 (bs, 1H) 7.37 (d, J=2.44 Hz, 1H) 7.49 (d, J=8.06 Hz, 1H) 7.53 (d, J=1.46 Hz, 1H) 7.64 (dd, J=8.06, 1.46 Hz, 1H) 8.20 (d, J=5.25 Hz, 1H) 11.91 (bs, 1H).
HRMS (ESI) calcd for C$_{17}$H$_{14}$F$_3$N$_5$O+H$^+$ 362.1223. found 362.1225.

5-(2-Aminopyrimidin-4-yl)-2-[5-chloro-2-(propan-2-yl)phenyl]-1H-pyrrole-3-carboxamide [(I), R1=CH(CH$_3$)$_2$, R2=Cl, R3=R4=NH$_2$, R12=H] (compd. 14)

$^1$H NMR (400 MHz, DMSO-d$_6$) δ ppm 1.06 (d, J=6.84 Hz, 6H) 2.79 (spt, J=6.90 Hz, 1H) 6.32 (bs, 2H) 6.71 (bs, 1H) 6.91 (d, J=5.25 Hz, 1H) 7.11 (bs, 1H) 7.21 (d, J=2.32 Hz, 1H) 7.34 (d, J=2.69 Hz, 1H) 7.38 (d, J=8.30 Hz, 1H) 7.44 (dd, J=8.30, 2.32 Hz, 1H) 8.18 (d, J=5.25 Hz, 1H) 11.89 (bs, 1H).
HRMS (ESI) calcd for C$_{18}$H$_{18}$ClN$_5$O+H$^+$ 356.1273. found 356.1271.

5-(2-Aminopyrimidin-4-yl)-2-[2,5-bis(trifluoromethyl)phenyl]-1H-pyrrole-3-carboxamide [(I), R1=CF$_3$, R2=CF$_3$, R3=R4=NH$_2$, R12=H] (compd. 15)

$^1$H NMR (400 MHz, DMSO-d$_6$) δ ppm 6.34 (bs, 2H) 6.69 (bs, 1H) 6.85 (d, J=5.25 Hz, 1H) 7.37 (d, J=2.44 Hz, 1H) 7.40 (bs, 1H) 7.79 (bs, 1H) 8.0-8.06 (m, 2H) 8.21 (d, J=5.25 Hz, 1H) 12.08 (bs, 1H).
HRMS (ESI) calcd for C$_{17}$H$_{11}$F$_6$ClN$_5$O+H$^+$ 416.0941. found 416.0945.

5-(2-Aminopyrimidin-4-yl)-2-[2-ethyl-5-(trifluoromethyl)phenyl]-1H-pyrrole-3-carboxamide [(I), R1=CH$_2$CH$_3$, R2=CF$_3$, R3=R4=NH$_2$, R12=H] (compd. 16)

$^1$H NMR (400 MHz, DMSO-d$_6$) δ ppm 1.02 (t, J=7.55 Hz, 3H) 2.57 (q, J=7.60 Hz, 4H) 6.37 (bs, 2H) 6.76 (bs, 1H) 6.92 (d, J=5.49 Hz, 1H) 7.33 (bs, 1H) 7.38 (d, J=2.47 Hz, 1H) 7.47-7.57 (m, 2H) 7.70 (d, J=7.14 Hz, 1H) 8.21 (d, J=5.22 Hz, 1H) 11.97 (bs, 1H).
HRMS (ESI) calcd for C$_{18}$H$_{16}$F$_3$N$_5$O+H$^+$ 376.138. found 376.1384.

5-(2-Aminopyrimidin-4-yl)-2-[5-chloro-2-(trifluoromethyl)phenyl]-1H-pyrrole-3-carboxamide [(I), R1=CF$_3$, R2=Cl, R3=R4=NH$_2$, R12=H] (compd. 17)

$^1$H NMR (400 MHz, DMSO-d$_6$) δ ppm 6.36 (bs, 2H) 6.68 (bs, 1H) 6.86 (d, J=5.25 Hz, 1H) 7.34 (bs, 1H) 7.35 (d, J=2.56 Hz, 1H) 7.54 (d, J=1.95 Hz, 1H) 7.70 (dd, J=8.48, 1.40 Hz, 1H) 7.80 (d, J=8.54 Hz, 1H) 7.95 (s, 1H) 8.21 (d, J=5.37 Hz, 1H) 12.03 (bs, 1H).
HRMS (ESI) calcd for C$_{16}$H$_{11}$ClF$_3$N$_5$O+H$^+$ 382.0677. found 382.0679.

5-(2-Aminopyrimidin-4-yl)-2-(5-cyano-2-methylphenyl)-1H-pyrrole-3-carboxamide [(I), R1=CH₃, R2=CN, R3=R4=NH₂, R12=H] (compd. 18)

$^1$H NMR (400 MHz, DMSO-d$_6$) δ ppm 2.22 (s, 3H) 6.33 (bs, 2H) 6.76 (bs, 1H) 6.91 (d, J=5.25 Hz, 2H) 7.35 (bs, 1H) 7.37 (d, J=2.56 Hz, 1H) 7.47 (d, J=7.93 Hz, 2H) 7.69 (d, J=1.83 Hz, 2H) 7.74 (dd, J=7.93, 1.83 Hz, 2H) 8.21 (d, J=5.25 Hz, 2H) 11.90 (bs, 1H).

HRMS (ESI) calcd for C$_{17}$H$_{14}$N$_6$O+H$^+$ 319.1302. found 319.1314.

Example 2

5-(2-Aminopyrimidin-4-yl)-2-(5-chloro-2-methylphenyl)-N-methyl-1H-pyrrole-3-carboxamide [(I), R1=CH₃, R2=Cl, R3=NHCH₃, R4=NH₂, R12=H] (compd. 19)

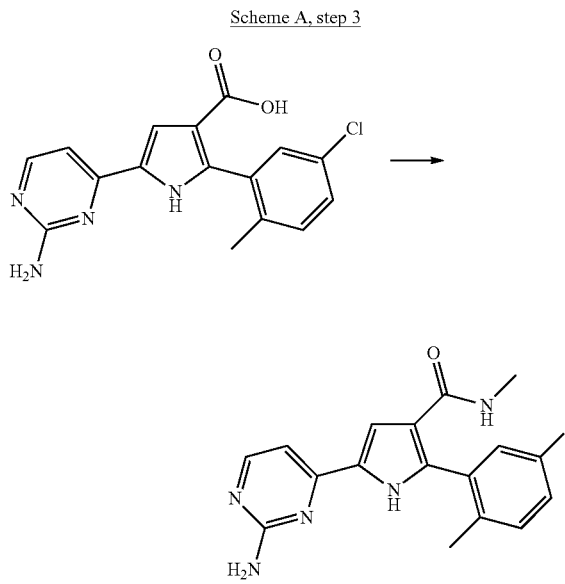

Scheme A, step 3

To a solution of 5-(2-aminopyrimidin-4-yl)-2-(5-chloro-2-methylphenyl)-1H-pyrrole-3-carboxylic acid (142 mg, 0.43 mmol) in DMF/THF 1/1 (4 mL) DIPEA (0.301 mL, 1.72 mmol) and MeNH₂ 2 M in THF (0.432 mL, 0.86 mmol) were added and the solution was stirred at 0° C. EDCl (157 mg, 0.86 mmol) and HOBT (117 mg, 0.86 mmol) were added and the reaction mixture was stirred for 4 h at room temperature. The mixture was diluted with water and extracted with DCM (4×10 mL). The organic phase was washed with brine, water and then dried over sodium sulfate and concentrated. The crude material was chromatographed on silica gel (DCM/MeOH 90/10) to afford the title compound (124 mg, 84%).

$^1$H NMR (400 MHz, DMSO-d$_6$) δ ppm 2.10 (s, 3H) 2.62 (d, J=4.52 Hz, 3H) 6.32 (bs, 1H) 6.93 (d, J=5.25 Hz, 1H) 7.27 (d, J=8.00 Hz, 1H) 7.29 (d, J=2.32 Hz, 1H) 7.31 (d, J=2.56 Hz, 1H) 7.35 (dd, J=8.30, 2.32 Hz, 1H) 7.80 (q, J=4.76 Hz, 1H) 8.19 (d, J=5.37 Hz, 1H) 11.84 (bs, 1H).

HRMS (ESI) calcd for C$_{17}$H$_{16}$ClN$_5$O+H$^+$ 342.1116. found 342.1118.

The above procedure was employed to synthesize the following compounds:

5-(2-Aminopyrimidin-4-yl)-2-(5-chloro-2-methylphenyl)-N-ethyl-1H-pyrrole-3-carboxamide [(I), R1=CH₃, R2=Cl, R3=NHCH₂CH₃, R4=NH₂, R12=H] (compd. 20)

$^1$H NMR (400 MHz, DMSO-d$_6$) δ ppm 1.02 (t, J=7.20 Hz, 3H) 2.11 (s, 3H) 3.12 (dq, J=7.10, 5.92 Hz, 2H) 6.32 (bs, 2H) 6.94 (d, J=5.25 Hz, 1H) 7.28 (d, J=2.32 Hz, 1H) 7.28 (d, J=8.30 Hz, 1H) 7.33 (d, J=2.56 Hz, 1H) 7.35 (dd, J=8.30, 2.32 Hz, 1H) 7.80 (t, J=5.68 Hz, 1H) 8.19 (d, J=5.25 Hz, 1H) 11.83 (bs, 1H).

HRMS (ESI) calcd for C$_{18}$H$_{18}$ClN$_5$O+H$^+$ 356.1273. found 356.1277.

5-(2-Aminopyrimidin-4-yl)-2-(5-chloro-2-methylphenyl)-N-(2-hydroxyethyl)-1H-pyrrole-3-carboxamide [(I), R1=CH₃, R2=Cl, R3=NHCH₂CH₂OH, R4=NH₂, R12=H] (compd. 21)

$^1$H NMR (400 MHz, DMSO-d$_6$) δ ppm 2.10 (s, 3H) 3.17 (q, J=6.06 Hz, 2H) 3.38-3.44 (m, 2H) 4.61 (t, J=5.37 Hz, 1H) 6.34 (bs, 2H) 6.94 (d, J=5.25 Hz, 1H) 7.23-7.30 (m, 2H) 7.32-7.38 (m, 2H) 7.71 (t, J=5.80 Hz, 1H) 8.20 (d, J=5.37 Hz, 1H) 11.86 (bs, 1H).

HRMS (ESI) calcd for C$_{18}$H$_{18}$ClN$_5$O$_2$+H$^+$ 372.1222. found 372.1230.

5-(2-Aminopyrimidin-4-yl)-2-(5-chloro-2-methylphenyl)-N-[2-(piperidin-1-yl)ethyl]-1H-pyrrole-3-carboxamide [(I), R1=CH₃, R2=Cl, R3=NH-[2-(piperidin-1-yl)ethyl, R4=NH₂, R12=H] (compd. 22)

$^1$H NMR (400 MHz, DMSO-d$_6$) δ ppm 1.28-1.39 (m, 2H) 1.39-1.48 (m, 4H) 2.11 (s, 3H) 2.20-2.35 (m, 6H) 3.19 (dq, J=6.80, 5.50 Hz, 2H) 6.33 (bs, 2H) 6.94 (d, J=5.25 Hz, 1H) 7.30 (d, J=7.95 Hz, 1H) 7.29 (d, J=2.20 Hz, 1H) 7.30 (d, J=2.00 Hz, 1H) 7.37 (dd, J=8.18, 2.20 Hz, 1H) 7.41 (t, J=5.37 Hz, 1H) 8.19 (d, J=5.25 Hz, 1H) 11.86 (bs, 1H).

HRMS (ESI) calcd for C$_{23}$H$_{27}$ClN$_6$O+H$^+$ 439.2008. found 439.2012.

5-(2-Aminopyrimidin-4-yl)-2-(5-chloro-2-methylphenyl)-N-(1-methylpiperidin-4-yl)-1H-pyrrole-3-carboxamide [(I), R1=CH₃, R2=Cl, R3=NH-(1-methylpiperidin-4-yl), R4=NH₂, R12=H] (compd. 23)

$^1$H NMR (400 MHz, DMSO-d$_6$) δ ppm 1.45 (dq, J=11.64, 3.91 Hz, 2H) 1.65 (dq, J=12.66, 3.14 Hz, 2H) 1.88 (td, J=11.41, 2.07 Hz, 2H) 2.10 (s, 3H) 2.12 (s, 3H) 2.63 (d, J=11.23 Hz, 2H) 3.49-3.62 (m, 1H) 6.32 (bs, 2H) 6.94 (d, J=5.25 Hz, 1H) 7.28 (d, J=8.67 Hz, 1H) 7.29 (d, J=2.00 Hz, 1H) 7.33-7.38 (m, 2H) 7.48 (d, J=8.18 Hz, 1H) 8.19 (d, J=5.25 Hz, 1H) 11.85 (bs, 1H).

HRMS (ESI) calcd for C$_{22}$H$_{25}$ClN$_6$O+H$^+$ 425.1851. found 425.1846.

5-(2-Aminopyrimidin-4-yl)-2-(5-chloro-2-methylphenyl)-N-phenyl-1H-pyrrole-3-carboxamide [(I), R1=CH₃, R2=Cl, R3=NHPh, R4=NH₂, R12=H] (compd. 24)

$^1$H NMR (400 MHz, DMSO-d$_6$) δ ppm 2.14 (s, 3H) 6.37 (bs, 2H) 6.99 (d, J=5.25 Hz, 1H) 7.00 (tt, J=7.40, 1.15 Hz, 1H) 7.26 (dd, J=8.36, 7.63 Hz, 2H) 7.30 (d, J=7.93 Hz, 1H) 7.34

(d, J=2.32 Hz, 1H) 7.37 (dd, J=7.93, 2.32 Hz, 1H) 7.57 (d, J=1.34 Hz, 1H) 7.65 (dd, J=8.61, 1.04 Hz, 2H) 8.23 (d, J=5.25 Hz, 1H) 9.74 (s, 1H) 12.05 (bs, 1H).

HRMS (ESI) calcd for $C_{22}H_{18}ClN_5O+H^+$ 404.1273. found 404.1274.

5-(2-Aminopyrimidin-4-yl)-2-(5-chloro-2-methylphenyl)-N-(furan-2-ylmethyl)-1H-pyrrole-3-carboxamide [(I), R1=CH$_3$, R2=Cl, R3=NH-(furan-2-ylmethyl), R4=NH$_2$, R12=H] (compd. 25)

$^1$H NMR (400 MHz, DMSO-d$_6$) δ ppm 2.08 (s, 3H) 4.30 (d, J=5.86 Hz, 2H) 6.16 (dq, J=3.22, 0.80 Hz, 1H) 6.32 (bs, 2H) 6.36 (dd, J=3.17, 1.83 Hz, 1H) 6.93 (d, J=5.25 Hz, 1H) 7.27 (d, J=7.93 Hz, 1H) 7.28 (d, J=2.20 Hz, 1H) 7.35 (dd, J=7.93, 2.20 Hz, 1H) 7.39 (d, J=2.56 Hz, 1H) 7.53 (dd, J=1.83, 0.85 Hz, 1H) 8.19 (d, J=5.37 Hz, 1H) 8.28 (t, J=5.86 Hz, 1H) 11.90 (bs, 1H).

HRMS (ESI) calcd for $C_{21}H_{18}ClN_5O_2+H^+$ 408.1222. found 408.1229.

5-(2-Aminopyrimidin-4-yl)-2-(5-chloro-2-methylphenyl)-N-(3-hydroxypropyl)-1H-pyrrole-3-carboxamide [(I), R1=CH$_3$, R2=Cl, R3=NHCH$_2$CH$_2$CH$_2$OH, R4=NH$_2$, R12=H] (compd. 26)

$^1$H NMR (400 MHz, DMSO-d$_6$) δ ppm 1.57 (quin, J=6.65 Hz, 2H) 2.10 (s, 3H) 3.15 (q, J=6.50 Hz, 2H) 4.40 (t, J=5.13 Hz, 1H) 6.33 (bs, 1H) 6.94 (d, J=5.13 Hz, 1H) 7.28 (d, J=8.18 Hz, 1H) 7.28 (d, J=2.32 Hz, 1H) 7.32 (s, 1H) 7.35 (dd, J=8.18, 2.20 Hz, 1H) 7.77 (t, J=5.55 Hz, 1H) 8.19 (d, J=5.25 Hz, 1H) 11.85 (bs, 1H).

HRMS (ESI) calcd for $C_{19}H_{20}ClN_5O_2+H^+$ 386.1379. found 386.1381.

5-(2-Aminopyrimidin-4-yl)-2-(5-chloro-2-methylphenyl)-N-(2-methoxyethyl)-1H-pyrrole-3-carboxamide [(I), R1=CH$_3$, R2=Cl, R3=NHCH$_2$CH$_2$OCH$_3$, R4=NH$_2$, R12=H] (compd. 27)

$^1$H NMR (400 MHz, DMSO-d$_6$) δ ppm 2.10 (s, 3H) 3.22 (s, 3H) 6.33 (bs, 2H) 6.94 (d, J=5.25 Hz, 1H) 7.28 (d, J=2.32 Hz, 1H) 7.29 (d, J=7.93 Hz, 1H) 7.34 (d, J=2.56 Hz, 1H) 7.36 (dd, J=8.18, 2.20 Hz, 1H) 7.69 (t, J=5.49 Hz, 1H) 8.19 (d, J=5.25 Hz, 1H) 11.87 (bs, 1H).

HRMS (ESI) calcd for $C_{19}H_{20}ClN_5O_2+H^+$ 386.1379. found 386.1385.

5-(2-Aminopyrimidin-4-yl)-2-(5-chloro-2-methylphenyl)-N-(2-fluoroethyl)-1H-pyrrole-3-carboxamide [(I), R1=CH$_3$, R2=Cl, R3=NHCH$_2$CH$_2$F, R4=NH$_2$, R12=H] (compd. 28)

$^1$H NMR (400 MHz, DMSO-d$_6$) δ ppm 2.10 (s, 3H) 3.44 (q, J=5.25 Hz, 2H) 4.43 (dt, J=47.48, 5.25 Hz, 2H) 6.33 (bs, 1H) 6.94 (d, J=5.25 Hz, 1H) 7.28 (d, J=8.30 Hz, 1H) 7.28 (d, J=2.32 Hz, 1H) 7.35 (dd, J=8.30, 2.32 Hz, 1H) 7.38 (d, J=1.95 Hz, 1H) 8.03 (t, J=5.55 Hz, 1H) 8.20 (d, J=5.25 Hz, 1H) 11.90 (bs, 1H).

HRMS (ESI) calcd for $C_{18}H_{17}ClFN_5O+H^+$ 374.1179. found 374.1185.

5-(2-Aminopyrimidin-4-yl)-2-(5-chloro-2-methylphenyl)-N,N-dimethyl-1H-pyrrole-3-carboxamide [(I), R1=CH$_3$, R2=Cl, R3=N(CH$_3$)$_2$, R4=NH$_2$, R12=H] (compd. 29)

$^1$H NMR (400 MHz, DMSO-d$_6$) δ ppm 2.17 (s, 3H) 2.84 (s, 6H) 6.36 (s, 1H) 6.99 (d, J=5.25 Hz, 1H) 7.00 (s, 1H) 7.30 (d, J=8.06 Hz, 1H) 7.29 (d, J=2.20 Hz, 1H) 7.35 (dd, J=8.30, 2.32 Hz, 1H) 8.19 (d, J=5.25 Hz, 1H) 11.84 (bs, 1H).

HRMS (ESI) calcd for $C_{18}H_{18}ClN_5O+H^+$ 356.1273. found 356.1277.

N-(Aminoethyl)-5-(2-aminopyrimidin-4-yl)-2-(5-chloro-2-methylphenyl)-1H-pyrrole-3-carboxamide [(I), R1=CH$_3$, R2=Cl, R3=NHCH$_2$CH$_2$NH$_2$, R4=NH$_2$, R12=H] (compd. 30)

Obtained from tert-butyl [3-({[5-(2-aminopyrimidin-4-yl)-2-(5-chloro-2-methylphenyl)-1H-pyrrol-3-yl]carbonyl}amino)ethyl]carbamate after treatment with TFA in DCM.

$^1$H NMR (400 MHz, DMSO-d$_6$) δ ppm 2.11 (s, 3H) 2.90 (sxt, 4H) 3.18 (q, J=6.35 Hz, 2H) 7.09 (bs, 2H) 7.07 (d, J=5.86 Hz, 1H) 7.30 (d, J=8.30 Hz, 1H) 7.30 (d, J=2.32 Hz, 1H) 7.38 (dd, J=8.30, 2.32 Hz, 1H) 7.51 (d, J=2.20 Hz, 1H) 7.71 (bs, 3H) 8.15 (t, J=5.55 Hz, 1H) 8.25 (d, J=5.86 Hz, 1H) 12.23 (bs, 1H).

HRMS (ESI) calcd for $C_{18}H_{19}ClN_6O+H^+$ 371.1382. found 371.1381.

5-(2-Aminopyrimidin-4-yl)-2-(5-chloro-2-methylphenyl)-N-[2-(methylamino)ethyl]-1H-pyrrole-3-carboxamide [(I), R1=CH$_3$, R2=Cl, R3=NHCH$_2$CH$_2$NHCH$_3$, R4=NH$_2$, R12=H] (compd. 31)

$^1$H NMR (400 MHz, DMSO-d$_6$) δ ppm 2.11 (s, 3H) 2.26 (s, 3H) 2.54 (t, J=6.47 Hz, 2H) 3.18 (q, J=6.35 Hz, 2H) 6.33 (bs, 2H) 6.94 (d, J=5.25 Hz, 1H) 7.29 (d, J=8.18 Hz, 1H) 7.29 (d, J=2.32 Hz, 1H) 7.33 (s, 1H) 7.36 (dd, J=8.18, 2.20 Hz, 1H) 7.66 (t, J=5.74 Hz, 1H) 8.19 (d, J=5.25 Hz, 1H) 11.86 (bs, 1H).

HRMS (ESI) calcd for $C_{19}H_{21}ClN_6O+H^+$ 385.1538. found 385.1541.

5-(2-Aminopyrimidin-4-yl)-N-benzyl-2-(5-chloro-2-methylphenyl)-1H-pyrrole-3-carboxamide [(I), R1=CH$_3$, R2=Cl, R3=NHCH$_2$Ph, R4=NH$_2$, R12=H] (compd. 32)

$^1$H NMR (400 MHz, DMSO-d$_6$) δ ppm 2.09 (s, 3H) 4.32 (d, J=6.10 Hz, 2H) 6.33 (bs, 2H) 6.94 (d, J=5.25 Hz, 1H) 7.17-7.32 (m, 7H) 7.32-7.37 (m, 1H) 7.40 (d, J=2.56 Hz, 1H) 8.20 (d, J=5.25 Hz, 1H) 8.38 (t, J=6.04 Hz, 1H) 11.89 (bs, 1H).

HRMS (ESI) calcd for $C_{19}H_{20}ClN_5O+H^+$ 370.1429. found 370.1431.

5-(2-Aminopyrimidin-4-yl)-2-(5-chloro-2-methylphenyl)-N-(2-methylpropyl)-1H-pyrrole-3-carboxamide [(I), R1=CH$_3$, R2=Cl, R3=NHCH$_2$CH(CH$_3$)$_2$, R4=NH$_2$, R12=H] (compd. 33)

$^1$H NMR (400 MHz, DMSO-d$_6$) δ ppm 0.81 (d, J=6.71 Hz, 6H) 1.71 (spt, J=6.80 Hz, 1H) 2.11 (s, 3H) 2.92 (t, J=6.41 Hz, 2H) 6.33 (bs, 2H) 6.95 (d, J=5.25 Hz, 1H) 7.28 (d, J=8.30 Hz, 1H) 7.29 (d, J=2.20 Hz, 1H) 7.35 (d, J=2.50 Hz, 1H) 7.35 (dd, J=8.30, 2.30 Hz, 1H) 7.72 (t, J=5.92 Hz, 1H) 8.19 (d, J=5.25 Hz, 1H) 11.84 (bs, 1H).

HRMS (ESI) calcd for $C_{18}H_{18}ClN_5O+H^+$ 356.1273. found 356.1276.

5-(2-Aminopyrimidin-4-yl)-2-(5-chloro-2-methylphenyl)-N-(2,2-dimethylpropyl)-1H-pyrrole-3-carboxamide [(I), R1=CH₃, R2=Cl, R3=NHCH₂C(CH₃)₃, R4=NH₂, R12=H] (compd. 34)

$^1$H NMR (400 MHz, DMSO-d$_6$) δ ppm 0.78 (s, 9H) 2.11 (s, 3H) 2.94 (d, J=6.35 Hz, 2H) 6.33 (s, 2H) 6.96 (d, J=5.37 Hz, 1H) 7.30 (d, J=8.20 Hz, 1H) 7.32 (d, J=2.32 Hz, 1H) 7.33-7.40 (m, 3H) 8.19 (d, J=5.37 Hz, 1H) 11.86 (bs, 1H).

HRMS (ESI) calcd for $C_{19}H_{20}ClN_5O+H^+$ 370.1429. found 370.1433.

5-(2-Aminopyrimidin-4-yl)-2-(5-chloro-2-ethylphenyl)-N-methyl-1H-pyrrole-3-carboxamide [(I), R1=CH₂CH₃, R2=Cl, R3=NHCH₃, R4=NH₂, R12=H] (compd. 35)

$^1$H NMR (400 MHz, DMSO-d$_6$) δ ppm 0.95 (t, J=7.57 Hz, 3H) 2.44 (q, J=7.61 Hz, 2H) 2.61 (d, J=4.64 Hz, 3H) 6.49 (bs, 2H) 6.94-6.96 (m, 1H) 7.24 (d, J=2.32 Hz, 1H) 7.30-7.33 (m, 1H) 7.34 (d, J=2.44 Hz, 1H) 7.39 (dd, J=8.30, 2.32 Hz, 1H) 7.75-7.83 (m, 1H) 8.19 (d, J=5.37 Hz, 1H) 11.94 (bs, 1H).

HRMS (ESI) calcd for $C_{18}H_{18}ClN_5O+H^+$ 356.1273. found 356.1281.

5-(2-Aminopyrimidin-4-yl)-2-(5-chloro-2-ethylphenyl)-N-ethyl-1H-pyrrole-3-carboxamide [(I), R1=CH₂CH₃, R2=Cl, R3=NHCH₂CH₃, R4=NH₂, R12=H] (compd. 36)

$^1$H NMR (400 MHz, DMSO-d$_6$) δ ppm 0.95 (t, J=7.57 Hz, 3H) 1.01 (t, J=7.20 Hz, 3H) 2.44 (q, J=7.65 Hz, 2H) 3.03-3.16 (m, 2H) 6.32 (bs, 2H) 6.93 (d, J=5.25 Hz, 1H) 7.24 (d, J=2.32 Hz, 1H) 7.32 (d, J=12.08 Hz, 1H) 7.32 (s, 1H) 7.39 (dd, J=8.31, 2.30 Hz, 1H) 7.75 (t, J=5.68 Hz, 1H) 8.19 (d, J=5.25 Hz, 1H) 11.87 (bs, 1H).

HRMS (ESI) calcd for $C_{19}H_{20}ClN_5O+H^+$ 370.1429. found 370.1434.

5-(2-aminopyrimidin-4-yl)-2-(5-chloro-2-ethylphenyl)-N-(2-hydroxyethyl)-1H-pyrrole-3-carboxamide [(I), R1=CH₂CH₃, R2=Cl, R3=NHCH₂CH₂OH, R4=NH₂, R12=H] (compd. 37)

$^1$H NMR (400 MHz, DMSO-d$_6$) δ ppm 0.96 (t, J=7.57 Hz, 3H) 2.44 (q, J=7.61 Hz, 2H) 3.11-3.18 (m, 2H) 3.36-3.41 (m, 2H) 4.60 (bs, 1H) 6.35 (bs, 2H) 6.93 (d, J=5.37 Hz, 1H) 7.24 (d, J=2.32 Hz, 1H) 7.32 (d, J=12.08 Hz, 1H) 7.36 (d, J=2.56 Hz, 1H) 7.40 (dd, J=8.30, 2.30 Hz, 1H) 7.67 (t, J=5.55 Hz, 1H) 8.19 (d, J=5.25 Hz, 1H) 11.90 (bs, 1H).

HRMS (ESI) calcd for $C_{19}H_{20}ClN_5O_2+H^+$ 386.1379. found 386.1380.

5-(2-Aminopyrimidin-4-yl)-2-(5-chloro-2-ethylphenyl)-N,N-dimethyl-1H-pyrrole-3-carboxamide [(I), R1=CH₂CH₃, R2=Cl, R3=N(CH₃)₂, R4=NH₂, R12=H] (compd. 38)

$^1$H NMR (400 MHz, DMSO-d$_6$) δ ppm 0.99 (t, J=7.57 Hz, 3H) 2.86 (bs, 6H) 6.36 (s, 2H) 6.98 (d, J=5.25 Hz, 1H) 7.29 (d, J=2.32 Hz, 1H) 7.34 (d, J=8.30 Hz, 1H) 7.40 (dd, J=8.30, 2.32 Hz, 1H) 8.18 (d, J=5.37 Hz, 1H) 11.85 (bs, 1H).

HRMS (ESI) calcd for $C_{21}H_{24}ClN_5O+H^+$ 398.1742. found 398.1740.

5-(2-Aminopyrimidin-4-yl)-2-[2-chloro-5-(trifluoromethyl)phenyl]-N-methyl-1H-pyrrole-3-carboxamide [(I), R1=Cl, R2=CF₃, R3=NHCH₃, R4=NH₂, R12=H] (compd. 39)

$^1$H NMR (400 MHz, DMSO-d$_6$) δ ppm 2.63 (d, J=4.64 Hz, 3H) 6.35 (bs, 2H) 6.90 (d, J=5.25 Hz, 1H) 7.33 (d, J=2.56 Hz, 1H) 7.72-7.80 (m, 3H) 7.90-7.94 (m, 1H) 8.22 (d, J=5.25 Hz, 1H) 12.07 (bs, 1H).

HRMS (ESI) calcd for $C_{17}H_{13}ClF_3N_5O+H^+$ 396.0834. found 396.0828.

5-(2-Aminopyrimidin-4-yl)-N-methyl-2-[2-methyl-5-(trifluoromethyl)phenyl]-1H-pyrrole-3-carboxamide [(I), R1=CH₃, R2=CF₃, R3=NHCH₃, R4=NH₂, R12=H] (compd. 50)

$^1$H NMR (400 MHz, DMSO-d$_6$) δ ppm 2.20 (s, 3H), 2.62 (d, J=4.64 Hz, 3H), 6.32 (bs, 2H), 6.92 (d, J=5.25 Hz, 1H), 7.34 (d, J=2.44 Hz, 1H), 7.53 (s, 1H), 7.47-7.51 (m, 1H), 7.53 (s, 1H), 7.64 (d, J=7.93 Hz, 1H), 7.86 (d, J=4.64 Hz, 1H), 8.20 (d, J=5.25 Hz, 1H), 11.92 (bs, 1H), HRMS (ESI) calcd for $C_{18}H_{16}F_3N_5O+H^+$ 376.1380. found 376.1380.

5-(2-Aminopyrimidin-4-yl)-2-[2-ethyl-5-(trifluoromethyl)phenyl]-N-methyl-1H-pyrrole-3-carboxamide [(I), R1=CH₂CH₃, R2=CF₃, R3=NHCH₃, R4=NH₂, R12=H] (compd. 51)

$^1$H NMR (400 MHz, DMSO-d$_6$) δ ppm 1.00 (t, J=7.57 Hz, 3H), 2.52-2.57 (m, 2H), 2.61 (d, J=4.52 Hz, 3H), 6.32 (bs, 2H), 6.91 (d, J=5.25 Hz, 1H), 7.34 (d, J=2.32 Hz, 1H), 7.49 (s, 1H), 7.52 (d, J=8.2 Hz, 1H), 7.68 (d, J=8.18 Hz, 1H), 7.84 (q, J=4.27 Hz, 1H), 8.19 (d, J=5.25 Hz, 1H), 11.94 (bs, 1H).

HRMS (ESI) calcd for $C_{19}H_{18}F_3N_5O+H^+$ 390.1536. found 390.1535.

Example 3

5-(2-Aminopyrimidin-4-yl)-2-(5-chloro-2-hydroxyphenyl)-1H-pyrrole-3-carboxamide [(I), R1=OH, R2=Cl, R3=R4=NH₂, R12=H] (compd. 40)

Conv. 1

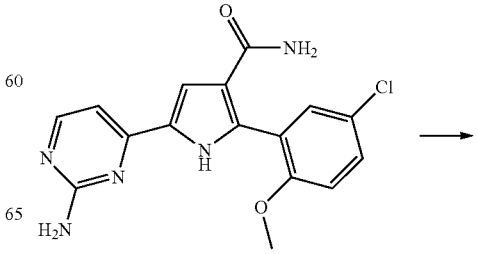

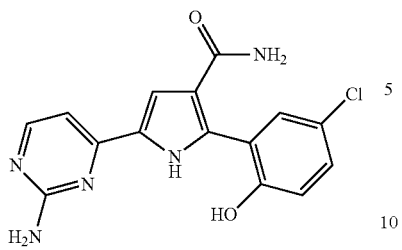

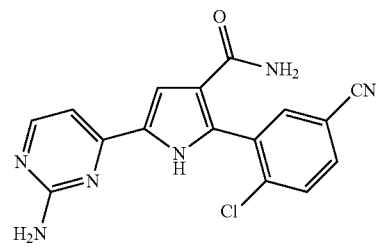

To a well stirred solution of 5-(2-aminopyrimidin-4-yl)-2-(5-chloro-2-methoxyphenyl)-1H-pyrrole-3-carboxamide (50 mg, 0.15 mmol) in DCM (1.5 mL) boron tribromide (1 M in DCM, 3 mL, 3 mmol) was added drop wise at 0° C. The mixture was stirred at room temperature overnight. The mixture was poured into water and the organic phase separated. The aqueous phase was extracted with EtOAc. The organic phases were collected, dried over sodium sulfate and concentrated. The crude material was purified by preparative HPLC (Method 2) to afford the title compound (11 mg, 22%).

$^1$H NMR (400 MHz, DMSO-$d_6$) δ ppm 6.41 (s, 2H) 6.95 (d, J=8.67 Hz, 1H) 6.99 (d, J=5.25 Hz, 1H) 7.28 (dd, J=8.67, 2.69 Hz, 1H) 7.33 (bs, 2H) 7.42 (d, J=2.69 Hz, 1H) 7.77 (bs, 1H) 8.22 (d, J=5.25 Hz, 1H) 10.90 (bs, 1H) 11.71 (bs, 1H).

HRMS (ESI) calcd for $C_{15}H_{12}C_1N_5O_2+H^+$ 330.0753. found 330.0758.

The above procedure was employed to synthesize the following compound:

5-(2-Aminopyrimidin-4-yl)-2-(2-chloro-5-hydroxyphenyl)-1H-pyrrole-3-carboxamide [(I), R1=Cl, R2=OH, R3=R4=NH$_2$, R12=H] (compd. 41)

$^1$H NMR (400 MHz, DMSO-$d_6$) δ ppm 6.33 (s, 2H) 6.70 (bs, 1H) 6.77-6.85 (m, 2H) 6.93 (d, J=5.25 Hz, 1H) 7.08 (bs, 1H) 7.24-7.33 (m, 2H) 8.19 (d, J=5.25 Hz, 1H) 9.72 (s, 1H) 11.83 (bs, 1H).

HRMS (ESI) calcd for $C_{15}H_{12}ClN_5O_2+H^+$ 330.0753. found 330.0751.

Example 4

5-(2-Aminopyrimidin-4-yl)-2-(2-chloro-5-cyanophenyl)-1H-pyrrole-3-carboxamide [(I), R1=Cl, R2=CN, R3=R4=NH$_2$, R12=H] (compd. 7)

Scheme B, step 4

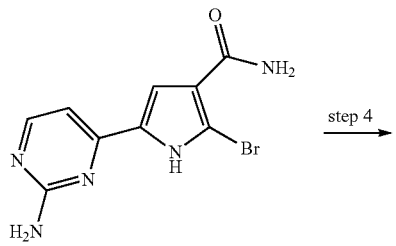

5-(2-Aminopyrimidin-4-yl)-2-bromo-1H-pyrrole-3-carboxamide (prepared according to WO2007/110344, 0.1 g, 0.35 mmol), 2-chloro-5-cyanophenylboronic acid (127 mg, 0.7 mmol), Na$_2$CO$_3$ (111 mg, 1.05 mmol), and PdCl$_2$(dppf) (28 mg, 0.035 mmol) in DME (2.5 mL) and water (1 mL) were heated at 80° C. for 12 h, under argon. After cooling to room temperature, the precipitate was filtered and the filtrate was evaporated under reduced pressure. The crude material was purified by preparative HPLC (Method 1) to afford the title compound (15 mg, 13%).

$^1$H NMR (400 MHz, DMSO-$d_6$) δ ppm 6.42 (bs, 2H) 6.79 (bs, 1H) 6.90 (d, J=5.25 Hz, 1H) 7.38 (d, J=2.56 Hz, 1H) 7.44 (bs, 1H) 7.73 (d, J=8.42 Hz, 1H) 7.88 (dd, J=8.42, 2.07 Hz, 1H) 7.94 (d, J=2.07 Hz, 1H) 8.23 (d, J=5.37 Hz, 1H) 12.07 (bs, 1H).

HRMS (ESI) calcd for $C_{16}H_{11}ClN_6O+H^+$ 339.0756. found 339.0761.

Example 5

2-(5-Chloro-2-methylphenyl)-5-[2-(methylamino)pyrimidin-4-yl]-1H-pyrrole-3-carboxamide [(I), R1=CH$_3$, R2=Cl, R3=NH$_2$, R4=NHCH$_3$, R12=H] (compd. 42)

Scheme C, steps 5, 6, 7, 8

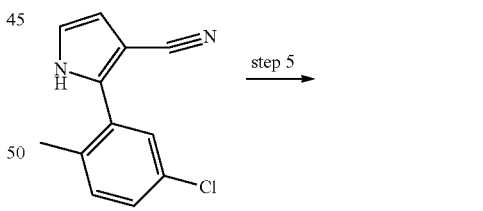

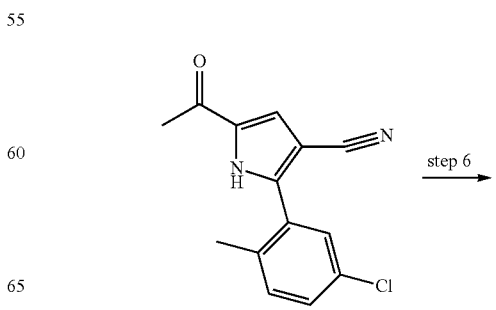

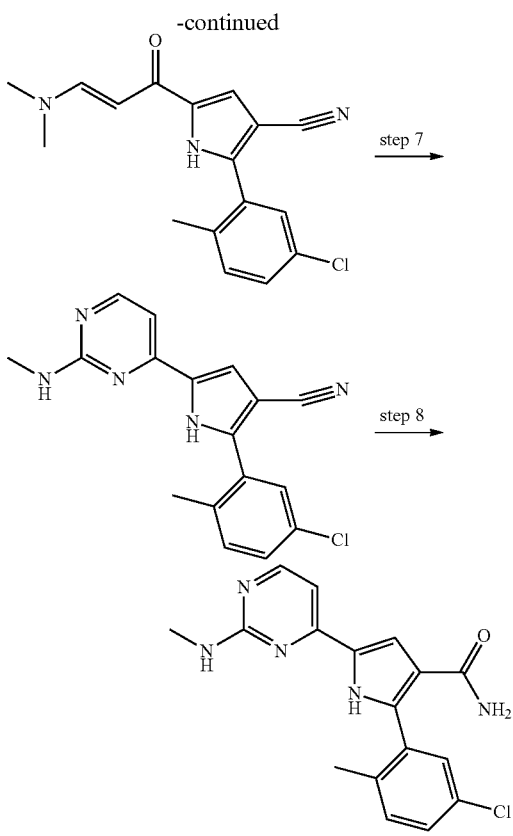

Step 5: 5-Acetyl-2-(5-chloro-2-methyl-phenyl)-1H-pyrrole-3-carbonitrile

To a mixture of 2-(5-chloro-2-methyl-phenyl)-1H-pyrrole-3-carbonitrile (900 mg, 4.14 mmol) in DCM (20 mL) was added acetyl chloride (0.468 mL, 6.57 mmol) at room temperature, under nitrogen. The resulting mixture was cooled to 0° C. and anhydrous aluminum trichloride (1.31 g, 9.9 mmol) was added in small portions during a period of 10 min, keeping the internal temperature below 5° C. Upon complete addition, the mixture was brought to room temperature and allowed to stir for 30 min. Then, the mixture was slowly poured in a solution of ice-cooled 1 M HCl (9 mL). The aqueous layer was separated and extracted twice with DCM (20 mL). The combined organic extracts were washed with brine, dried over $Na_2SO_4$ and concentrated under reduced pressure. The crude material was chromatographed on silica gel (10 to 20% EtOAc/hexane) to afford the title compound (1.0 g, 86%).

$^1$H NMR (400 MHz, DMSO-$d_6$) δ ppm 2.24 (s, 3H) 2.43 (s, 3H) 7.38-7.42 (m, 1H) 7.43 (d, J=2.32 Hz, 1H) 7.46-7.50 (m, 1H) 7.60 (s, 1H) 12.89 (bs, 1H).

HRMS (ESI) calcd for $C_{14}H_{11}ClN_2O+H^+$ 259.0633. found 259.0638.

Step 6: 2-(5-Chloro-2-methyl-phenyl)-5-(E)-3-dimethylamino-acryloyl)-1H-pyrrole-3-carbonitrile To a suspension of 5-acetyl-2-(5-chloro-2-methyl-phenyl)-1H-pyrrole-3-carbonitrile (990 mg, 3.83 mmol) in DMF (5 mL) was added N,N-dimethylformamide diisopropyl acetal (2.4 mL, 11.5 mmol). The mixture was allowed to stir overnight at 90° C. The mixture was evaporated in vacuo and used in the next step without further purification.

Step 7: 2-(5-Chloro-2-methyl-phenyl)-5-(2-methylamino-pyrimidin-4-yl)-1H-pyrrole-3-carbonitrile To a suspension of 2-(5-chloro-2-methyl-phenyl)-5-(E)-3-dimethylamino-acryloyl)-1H-pyrrole-3-carbonitrile (618 mg, 1.91 mmol) in DMF (5 mL) was added methylguanidine hydrochloride (230 mg, 2.1 mmol) and $K_2CO_3$ (318 mg, 2.29 mmol). The mixture was heated to 110° C. overnight under efficient stirring. The resulting mixture was concentrated and chromatographed on silica gel (10 to 30% EtOAc/hexane) to afford the title compound (300 mg, 48%, 2 steps).

$^1$H NMR (400 MHz, DMSO-$d_6$) δ ppm 2.28 (s, 3H) 2.88 (d, J=4.52 Hz, 3H) 6.83-6.95 (m, 1H) 6.95-7.03 (m, 1H) 7.36-7.41 (m, 1H) 7.41-7.46 (m, 1H) 7.46-7.53 (m, 3H) 8.27 (d, J=4.64 Hz, 1H) 12.53 (bs, 1H).

HRMS (ESI) calcd for $C_{17}H_{14}ClN_5+H^+$ 324.1011. found 324.1013.

Step 8: 2-(5-Chloro-2-methyl-phenyl)-5-(2-methylamino-pyrimidin-4-yl)-1H-pyrrole-3-carboxamide To a solution of 2-(5-chloro-2-methyl-phenyl)-5-(2-methylamino-pyrimidin-4-yl)-1H-pyrrole-3-carbonitrile (74 mg, 0.23 mmol) in TFA (1.0 mL) were sequentially added water (0.15 mL) and 98% sulfuric acid (0.30 mL) under efficient stirring. The mixture was allowed to stir for 8 h at 70° C. and then was diluted by drop wise addition of water (3 mL).

The reaction mixture was made basic (pH 10-12) by adding 30% aqueous ammonia (1 mL) under stirring. The precipitated solid was collected by filtration, washed with water and finally dried in a vacuum oven at 50° C. affording the title compound as an off-white solid (66 mg, 88%).

$^1$H NMR (400 MHz, DMSO-$d_6$) δ ppm 2.12 (s, 3H) 2.88 (d, J=4.15 Hz, 3H) 6.67-6.83 (m, 1H) 6.88 (d, J=5.13 Hz, 1H) 7.19 (bs, 1H) 7.26-7.32 (m, 2H) 7.34-7.38 (m, 1H) 7.39 (s, 1H) 8.20 (d, J=5.37 Hz, 1H) 11.87 (bs, 1H).

HRMS (ESI) calcd for $C_{17}H_{16}ClN_5O+H^+$ 342.1116. found 342.1118.

Example 6

5-(Pyrimidin-4-yl)-2-(5-chloro-2-methyl-phenyl)-1H-pyrrole-3-carboxamide [(I), R1=CH$_3$, R2=Cl, R3=NH$_2$, R4=H, R12=H] (compd. 43)

Scheme D, steps 9 and 10

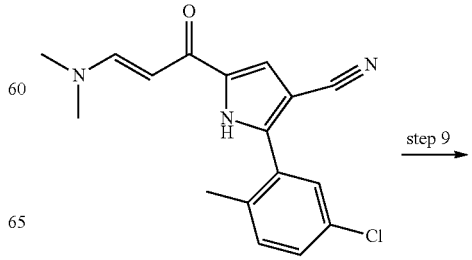

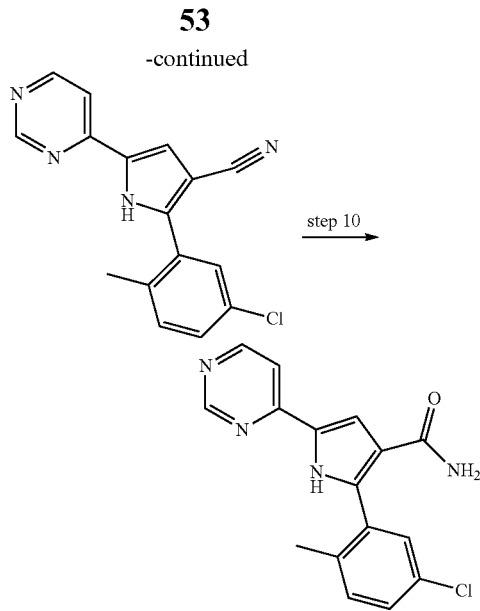

Step 9: 5-(Pyrimidin-4-yl)-2-(5-chloro-2-methyl-phenyl)-1H-pyrrole-3-carbonitrile To a suspension of 2-(5-chloro-2-methyl-phenyl)-5-((E)-3-dimethylamino-acryloyl)-1H-pyrrole-3-carbonitrile (313 mg, 1.0 mmol) in DMF (5 mL) was added formamidine acetate (208 mg, 2.0 mmol). The mixture was heated to 150° C. for 5 h under efficient stirring. The resulting mixture was diluted by dropwise addition of water and extracted with EtOAc.

The organic phase was washed with brine, water and then dried over $Na_2SO_4$ and concentrated. The crude material was chromatographed on silica gel (hexane/EtOAc 90/10) to afford the title compound (90 mg, 30%).

$^1$H NMR (400 MHz, DMSO-$d_6$) δ ppm 2.30 (s, 3H) 7.40-7.45 (m, 1H) 7.46-7.53 (m, 2H) 7.61 (s, 1H) 7.90 (dd, J=5.43, 1.28 Hz, 1H) 8.79 (d, J=5.37 Hz, 1H) 9.13 (d, J=1.22 Hz, 1H) 12.98 (bs, 1H).

HRMS (ESI) calcd for $C_{16}H_{11}ClN_4+H^+$ 295.0745. found 295.0750.

Step 10: 5-(Pyrimidin-4-yl)-2-(5-chloro-2-methyl-phenyl)-1H-pyrrole-3-carboxamide To a solution of 5-(pyrimidin-4-yl)-2-(5-chloro-2-methyl-phenyl)-1H-pyrrole-3-carbonitrile (85 mg, 0.28 mmol) in TFA (1.0 mL) were sequentially added water (0.15 mL) and 98% sulfuric acid (0.30 mL) under efficient stirring. The mixture was allowed to stir for 5 h at 70° C. and then was diluted by drop wise addition of water (1 mL). The reaction mixture was made basic (pH 10-12) by adding 30% aqueous ammonia (3 mL) under stirring. The precipitated solid was collected by filtration, washed with water and finally dried in a vacuum oven at 50° C. affording the title compound (72 mg, 83%).

$^1$H NMR (400 MHz, DMSO-$d_6$) δ ppm 2.13 (s, 3H) 6.81 (bs, 1H) 7.19-7.33 (m, 3H) 7.33-7.40 (m, 1H) 7.57 (d, J=2.69 Hz, 1H) 7.74 (dd, J=5.43, 1.40 Hz, 1H) 8.70 (d, J=5.49 Hz, 1H) 9.04 (d, J=1.10 Hz, 1H) 12.22 (bs, 1H).

HRMS (ESI) calcd for $C_{16}H_{13}ClN_4O+H^+$ 313.0851. found 313.0853.

The above procedure was employed to synthesize the following compound:

2-(5-Chloro-2-methylphenyl)-5-(2-methylpyrimidin-4-yl)-1H-pyrrole-3-carboxamide [(I), R1=CH$_3$, R2=Cl, R3=NH$_2$, R4=CH$_3$, R12=H] (compd. 44)

$^1$H NMR (400 MHz, DMSO-$d_6$) δ ppm 2.12 (s, 3H) 2.59 (s, 3H) 6.80 (bs, 1H) 7.24-7.31 (m, 2H) 7.33 (bs, 1H) 7.34-7.38 (m, 1H) 7.50-7.58 (m, 2H) 8.59 (d, J=5.34 Hz, 1H) 12.13 (bs, 1H).

HRMS (ESI) calcd for $C_{17}H_{15}ClN_4O+H^+$ 327.1007. found 327.1011.

Example 7

5-(2-Aminopyrimidin-4-yl)-2-[2-chloro-5-(trifluoromethyl)phenyl]-1H-pyrrole-3-carboxamide [(I), R1=Cl, R2=CF$_3$, R3=R4=NH$_2$, R12=H] (compd. 1)

Scheme C, steps 5, 6, 7, 8

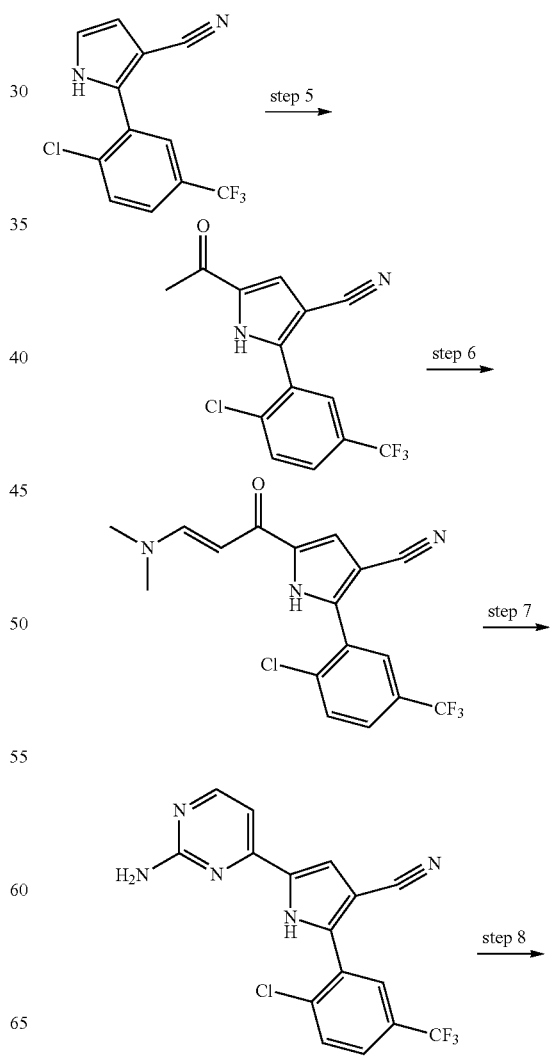

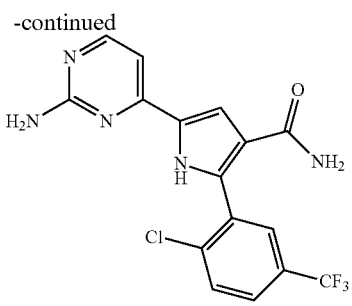

Step 5: 5-Acetyl-2-[2-chloro-5-(trifluoromethyl)phenyl]-1H-pyrrole-3-carbonitrile To a mixture of 2-[2-chloro-5-(trifluoromethyl)phenyl]-1H-pyrrole-3-carbonitrile (450 mg, 1.66 mmol) in toluene (3 mL) was added acetyl chloride (0.176 mL, 2.49 mmol) at room temperature, under nitrogen, and zinc (217 mg, 3.32 mmol). The mixture was allowed to stir for 3 h at 80° C. The mixture was cooled to room temperature, diluted with EtOAc and washed with water. The aqueous layer was separated and extracted twice with EtOAc. The combined organic extracts were washed with brine, dried over $Na_2SO_4$ and concentrated under reduced pressure. The crude material was chromatographed on silica gel (0 to 10% EtOAc/hexane) to afford the title compound (386 mg, 74%).

$^1$H NMR (400 MHz, DMSO-$d_6$) δ ppm 2.45 (s, 3H) 7.66 (s, 1H) 7.81-7.96 (m, 2H) 7.98 (s, 1H) 13.15 (bs, 1H).

Step 6: 2-[2-Chloro-5-(trifluoromethyl)phenyl]-5-(E)-3-dimethylamino-acryloyl)-1H-pyrrole-3-carbonitrile To a mixture of 5-acetyl-2-[2-chloro-5-(trifluoromethyl)phenyl]-1H-pyrrole-3-carbonitrile (280 mg, 0.89 mmol) in toluene (3 mL) was added N,N-dimethylformamide diisopropyl acetal (0.74 mL, 3.56 mmol). The mixture was allowed to stir 2 h at 80° C. After cooling to room temperature, the solid was collected by suction, washed with toluene and dried in the air to yield the title compound as white solid (170 mg, 52%).

$^1$H NMR (400 MHz, DMSO-$d_6$) δ ppm 2.91 (bs, 3H) 3.14 (bs, 3H) 5.74 (d, J=12.45 Hz, 1H) 7.40 (s, 1H) 7.69 (d, J=12.45 Hz, 1H) 7.81-7.99 (m, 3H) 12.74 (bs, 1H).

Step 7: 5-(2-Amino-pyrimidin-4-yl)-2-[2-chloro-5-(trifluoromethyl)phenyl]-1H-pyrrole-3-carbonitrile To a mixture of 2-[2-chloro-5-(trifluoromethyl)phenyl]-5-(E)-3-dimethylamino-acryloyl)-1H-pyrrole-3-carbonitrile (167 mg, 0.46 mmol) in DMF (2 mL) was added guanidine carbonate (388 mg, 2.15 mmol). The mixture was heated at 110° C. 2 h under efficient stirring. The resulting mixture was concentrated and chromatographed on silica gel (20 to 50% EtOAc/hexane) to afford the title compound (142 mg, 86%).

$^1$H NMR (400 MHz, DMSO-$d_6$) δ ppm 6.49 (bs, 2H) 7.02 (d, J=5.13 Hz, 1H) 7.39 (s, 1H) 7.85-8.03 (m, 3H) 8.28 (d, J=5.13 Hz, 1H) 12.81 (bs, 1H).

Step 8: 5-(2-Aminopyrimidin-4-yl)-2-[2-chloro-5-(trifluoromethyl)phenyl]-1H-pyrrole-3-carboxamide A solution of TFA (2.0 mL), water (0.480 mL) and 98% sulfuric acid (0.240 mL) was added to 5-(2-amino-pyrimidin-4-yl)-2-[2-chloro-5-(trifluoromethyl)phenyl]-1H-pyrrole-3-carbonitrile (137 mg, 0.415 mmol). The mixture was allowed to stir for 8 h at 70° C. and then was diluted by drop wise addition of water (6 mL). The reaction mixture was made basic (pH 10-12) by adding 30% aqueous ammonia under stirring. The precipitated solid was collected by filtration, washed with water and finally dried in a vacuum oven at 50° C. affording the title compound as a white solid (133 mg, 92%).

$^1$H NMR (400 MHz, DMSO-$d_6$) δ ppm 6.36 (bs, 2H) 6.77 (bs, 1H) 6.90 (d, J=5.25 Hz, 1H) 7.37 (d, J=2.56 Hz, 1H) 7.42 (bs, 1H) 7.69-7.84 (m, 3H) 8.22 (d, J=5.25 Hz, 1H) 12.07 (bs, 1H).

HRMS (ESI) calcd for $C_{16}H_{11}ClF_3N_5O+H^+$ 382.0677. found 382.0675.

Example 8

5-(2-Aminopyrimidin-4-yl)-2-(5-chloro-2-ethylphenyl)-1-methyl-1H-pyrrole-3-carboxamide [(I), R1=$CH_2CH_3$, R2=Cl, R3=R4=$NH_2$, R12=$CH_3$] (compd. 45)

Conv. 2

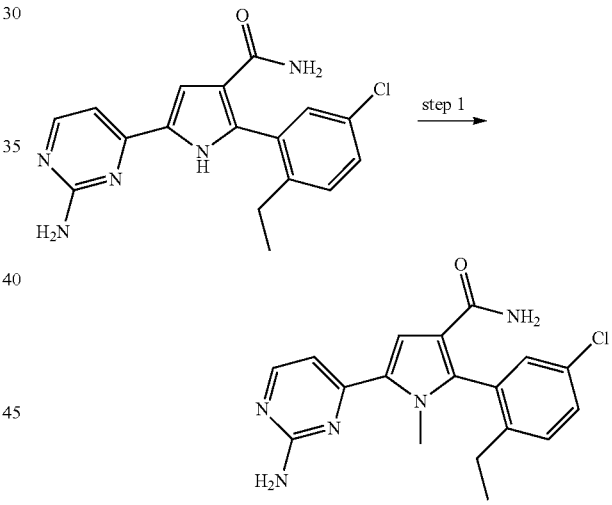

To a solution of 5-(2-aminopyrimidin-4-yl)-2-(5-chloro-2-ethylphenyl)-1H-pyrrole-3-carboxamide (101 mg, 0.295 mmol) in DMF (1 mL), $Cs_2CO_3$ (101 mg, 0.31 mmol) and MeI (28 μL, 0.43 mmol) were added. The mixture was stirred at room temperature for 3 h, then the solvent was removed. To the residue EtOAc and water were added, the layers were separated, the aqueous layer was extracted with EtOAc and the combined organic layers were washed with water, dried over $Na_2SO_4$, filtered and concentrated. The crude material was purified by flash chromatography (DCM/MeOH/$NH_3$ in MeOH 95/5/0.5) affording the title compound (36 mg, 34% yield).

$^1$H NMR (400 MHz, DMSO-$d_6$) δ ppm 0.96 (t, J=7.57 Hz, 3H) 2.18-2.45 (m, 2H) 3.61 (s, 3H) 6.58 (s, 2H) 6.71 (bs, 1H) 6.82 (d, J=5.37 Hz, 1H) 7.03 (bs, 1H) 7.21 (d, J=2.32 Hz, 1H) 7.35 (s, 1H) 7.36-7.40 (m, 1H) 7.41-7.48 (m, 1H) 8.21 (d, J=5.37 Hz, 1H).

The above procedure was employed to synthesize the following compounds:

5-(2-Aminopyrimidin-4-yl)-2-(5-chloro-2-methylphenyl)-1-methyl-1H-pyrrole-3-carboxamide [(I), R1=CH$_3$, R2=Cl, R3=R4=NH$_2$, R12=CH$_3$] (compd. 46)

$^1$H NMR (400 MHz, DMSO-d$_6$) δ ppm 2.00 (s, 3H) 3.61 (s, 3H) 6.54 (s, 2H) 6.71 (bs, 1H) 6.81 (d, J=5.36 Hz, 1H) 7.04 (bs, 1H) 7.23 (d, J=2.19 Hz, 1H) 7.35 (d, J=8.30 Hz, 1H) 7.33 (s, 1H) 7.40 (dd, J=8.17, 2.19 Hz, 1H) 8.21 (d, J=5.36 Hz, 1H).

5-(2-Aminopyrimidin-4-yl)-2-(5-chloro-2-methylphenyl)-1-ethyl-1H-pyrrole-3-carboxamide [(I), R1=CH$_3$, R2=Cl, R3=R4=NH$_2$, R12=CH$_2$CH$_3$] (compd. 47)

$^1$H NMR (400 MHz, DMSO-d$_6$) δ ppm 0.99 (t, J=7.20 Hz, 3H) 2.01 (s, 3H) 4.00 (dq, J=13.66, 6.96 Hz, 1H) 4.43 (dq, J=13.55, 6.92 Hz, 1H) 6.52 (s, 2H) 6.70 (bs, 1H) 6.81 (d, J=5.37 Hz, 1H) 7.03 (bs, 1H) 7.25 (d, J=2.32 Hz, 1H) 7.35 (d, J=8.18 Hz, 1H) 7.36 (s, 2H) 7.41 (dd, J=8.18, 2.20 Hz, 1H) 8.20 (d, J=5.25 Hz, 1H).

5-(2-Aminopyrimidin-4-yl)-2-(5-chloro-2-methylphenyl)-1-(2,2,2-trifluoroethyl)-1H-pyrrole-3-carboxamide [(I), R1=CH$_3$, R2=Cl, R3=R4=NH$_2$, R12=CH$_2$CF$_3$] (compd. 48)

$^1$H NMR (400 MHz, DMSO-d$_6$) δ ppm 2.02 (s, 3H) 5.46 (bs, 2H) 6.67 (s, 2H) 6.84 (d, J=5.24 Hz, 1H) 6.90 (bs, 1H) 7.24 (bs, 1H) 7.25 (d, J=2.07 Hz, 1H) 7.34-7.38 (m, 1H) 7.41-7.45 (m, 1H) 7.45 (s, 1H) 8.26 (d, J=5.24 Hz, 1H).

5-(2-Aminopyrimidin-4-yl)-2-(5-chloro-2-methylphenyl)-1-(2-hydroxyethyl)-1H-pyrrole-3-carboxamide [(I), R1=CH$_3$, R2=Cl, R3=R4=NH$_2$, R12=CH$_2$CH$_2$OH] (compd. 49)

Obtained from 5-(2-aminopyrimidin-4-yl)-2-(5-chloro-2-methylphenyl)-1-[2-(tetrahydro-2H-pyran-2-yloxy)ethyl]-1H-pyrrole-3-carboxamide after treatment with conc. HCl in EtOH.

$^1$H NMR (400 MHz, DMSO-d$_6$) δ ppm 2.00 (s, 3H) 3.98 (dt, J=12.97, 7.00 Hz, 1H) 4.08 (q, J=5.17 Hz, 2H) 4.46 (ddd, J=12.97, 7.11, 5.92 Hz, 1H) 4.67 (t, J=5.80 Hz, 1H) 6.54 (s, 2H) 6.70 (bs, 1H) 6.82 (d, J=5.37 Hz, 1H) 7.01 (bs, 1H) 7.26 (d, J=2.32 Hz, 1H) 7.33 (d, J=8.30 Hz, 1H) 7.38 (s, 1H) 7.39 (dd, J=8.30, 2.32 Hz, 1H) 8.20 (d, J=5.25 Hz, 1H).

Pharmacology
Biochemical Assay for Inhibitors of JAK Kinases Activity
General Principle—

Specific JAK2, JAK1 or JAK3 peptide substrates are trans-phosphorylated by JAK kinases in the presence of ATP traced with 33P-γ-ATP. At the end of the phosphorylation reaction, the unreacted ATP, cold and radioactive, is captured by an excess of dowex ion exchange resin that eventually settles by gravity to the bottom of the reaction plate. The supernatant is subsequently withdrawn and transferred into a counting plate that is then evaluated by β-counting.

Dowex Resin Preparation—

500 g of wet resin (SIGMA, custom prepared resin DOWEX 1×8 200-400 mesh, 2.5 Kg) is weighed out and diluted 2 to 1 in 150 mM sodium formate, pH 3.00. The resin is allowed to settle overnight and then the supernatant is discarded. After three washes as above over a couple of days, the resin is allowed to settle and two volumes (with respect to the resin volume) of 150 mM sodium formate buffer are added.

Kinase Buffer (KB)—

Kinase buffer was composed of 50 mM HEPES pH 7.5 containing 10 mM MgCl$_2$, 2.5 mM DTT, 10 μM Na$_3$VO$_4$ and 0.2 mg/mL BSA.

JAK2 Specific Assay Conditions
Enzyme—

Assays were performed with the commercially available JAK2 kinase domain (Invitrogen, Eugene, Oreg.) that showed a linear kinetic without prephosphorylation.

Assay Conditions—

The JAK2 kinase assay was run with a final enzyme concentration of 1 nM, in the presence of 60 μM ATP, 3 nM 33P-γ-ATP and 64 μM of substrate BioDBn*306 (Aminoacid sequence: LPLDKDYYWREPGQ—SEQ ID NO: 1). The peptidic substrate was purchased from American Peptide Company (Sunnyvale, Calif.).

JAK1 Specific Assay Conditions
Enzyme—

Assays were performed with the JAK1 kinase domain (residues 861-1152 of the 1154 amino acid long full-length sequence, accession number P23458 of UniProtKB/Swiss-Prot database).

The JAK1 kinase domain was pre activated with ATP for 1 h at 28° C. in order to obtain a linear kinetic.

Assay Conditions—

The JAK1 kinase assay was run with a final pre activated enzyme concentration of 2.5 nM, in the presence of 100 μM ATP, 2 nM 33P-γ-ATP and 154 μM of substrate BioDBn*333 (Aminoacid sequence: KKHTDDGYMPMSPGVA—SEQ ID NO: 2). The peptidic substrate was purchased from American Peptide Company (Sunnyvale, Calif.).

JAK3 Specific Assay Conditions
Enzyme—

Assays were performed with the JAK3 kinase domain (residues 781-1124 of the 1124 amino acid long full-length sequence, accession number P52333 of UniProtKB/Swiss-Prot database) that showed a linear kinetic without pre-phosphorylation.

Assay Conditions—

The JAK3 kinase assay was run with a final enzyme concentration of 1 nM, in the presence of 22 μM ATP, 1 nM 33P-γ-ATP and 40 μM of substrate BioDBn*306 (Aminoacid sequence: LPLDKDYYWREPGQ—SEQ ID NO: 1). The peptidic substrate was purchased from American Peptide Company (Sunnyvale, Calif.).

Compound Dilution—

For IC$_{50}$ determination, test compounds are received as a 1 mM solution in 100% DMSO, distributed into 96 well plates: compounds are then plated into the first column of a microtiter plate (A1 to G1), 100 μL/well. An automated station for serial dilutions (Biomek FX, Beckman) is used for producing 1:3 dilutions in 100% DMSO, from line A1 to A10, and for all the compounds in the column. Moreover, 4-5 copies of daughter plates are prepared by reformatting 5 μL of this first set of 100% DMSO dilution plates into 384 deep well-plates: one of these plates with the serial dilutions of test compounds will be thawed the day of the experiments, reconstituted at a 3× concentration with water and used in the IC$_{50}$ determination assays. In a standard experiment, the highest concentration (3×) of all compounds is 30 μM, while the lowest one is 1.5 nM. Each 384 well-plate will contain at least one curve of the standard inhibitor staurosporine and reference wells (total enzyme activity vs. no enzymatic activity) for the Z' and signal to background evaluation.

Assay Scheme—

384-well plates, V bottom (test plates) are prepared with 5 µL of the compound dilution (3×) and then placed onto a PlateTrak 12 robotized station (Perkin Elmer; the robot has one 384-tip pipetting head for starting the assay plus one 96-tip head for dispensing the resin) together with one reservoir for the Enzyme mix (3×) and one for the ATP mix (3×). At the start of the run, the robot aspirates 5 µL of ATP mix, makes an air gap inside the tips (3 µl) and aspirates 5 µL of JAK2 mix. The following dispensation into the plates plus 3 cycles of mixing, done by the robot itself, starts the kinase reaction. At this point, the correct concentrations are restored for all the reagents. The robot incubates the plates for 60 minutes at room temperature, and then stops the reaction by pipetting 60 µL of dowex resin suspension into the reaction mix. In order to avoid tip clogging, wide bore tips are used to dispense the resin suspension. Three cycles of mixing are done immediately after the addition of the resin. Another mixing cycle is performed after all the plates are stopped, this time using normal tips: the plates are then allowed to rest for about one hour in order to allow resin sedimentation. At this point, 27 µL of the supernatant are transferred into 384-Optiplates (Perkin-Elmer), with 50 µL of Microscint 40 (Perkin-Elmer); after 5 min of orbital shaking the plates are read on a Perkin-Elmer Top Count radioactivity counter.

Data Fitting—

Data are analyzed by an internally customized version of the SW package "Assay Explorer" that provides sigmoidal fitting of the ten-dilutions curves for $IC_{50}$ determination in the secondary assays/hit confirmation routines.

Cell Proliferation

Cell Lines:

the JAK2 dependent human megakaryoblastic leukemia cell line SET-2 (DSMZ, Braunschweig GERMANY), and JAK2 independent human chronic myelogenous leukaemia cell line K562 (ECACC, Wiltshire, UK) were cultured in RPMI-1640 medium-Glutamax (Gibco BRL, Gaithesburg, Md., USA), supplemented with 10% fetal bovine serum (FBS) at 37° C. and 5% $CO_2$.

Cell Proliferation Assay:

Approximately $5 \times 10^3$ cells were plated into 384 microtiter plate wells in 50 µL of growth media with different concentrations of inhibitors. The cells were incubated at 37° C. and 5% $CO_2$ for 72 hours, than the plates were processed using CellTiter-Glo assay (Promega, Madison, Wis., USA) following the manufacturer's instruction. Briefly 25 µL/well reagent solution are added to each wells and after 5 minutes shacking micro-plates are read by Envision luminometer (PerkinElmer, Waltham, Mass., USA).

Data Fitting—

Data are analyzed by Symix Assay Explorer software (Symix Technologies Inc.) that provides sigmoidal fitting algorithm of the 8 points dilutions curves for 1050 determination.

In Vivo Model

Acute megakaryoblastic leukemia cell line SET-2 ($10^7$ cells) was inoculated s.c. in 5-6 weeks old female severe combined immunodeficient (SCID) mice (Charles River) previously exposed to gamma-irradiation (200 Rads of whole body gamma-irradiation). Mice bearing a palpable tumor (100-200 mm$^3$) were treated with vehicle (0.5% Methocel) or Compounds of formula (I) for 10 days, bid. Tumor dimensions were measured regularly using Vernier calipers and tumor growth inhibition (TGI) was calculated.

Surprisingly in biochemical assays, the compounds of formula (I) tested as described above demonstrate a remarkably potent JAK2 inhibitory activity, typically lower than 0.020 µM.

See, as an example, the following Table A wherein are reported experimental data ($IC_{50}$) of representative compounds of the invention of formula (I) in comparison with Ref. compound.

Ref. compound corresponds to compound F25 of the patent application WO2007/110344 cited above and it is the fourth disclaimed compound in the present formula (I).

In cellular assays, the compounds of formula (I) showed higher activity in JAK2 dependent SET-2 cell line in comparison to JAK2 independent K562 cell line.

Moreover the higher selectivity in JAK2 dependent cell line of the compounds of formula (I) vs Ref. Compound is indicated by the Ratio between K-562 ($IC_{50}$) and SET-2 ($IC_{50}$), that is higher than 9 for the compounds of formula (I) vs 4.65 for the Ref. Compound (see the last column of Table A below).

TABLE A

| Cmpd. | JAK2 $IC_{50}$ µM | SET-2 $IC_{50}$ µM | K-562 $IC_{50}$ µM | Ratio K-562 ($IC_{50}$)/ SET-2 ($IC_{50}$) |
|---|---|---|---|---|
| Ref. cmpd. (F25) | 0.020 | 0.43 | 2.00 | 4.65 |
| Cmpd. 1 | 0.008 | 0.57 | 7.50 | 13 |
| Cmpd. 2 | 0.012 | 0.70 | 6.86 | 9.8 |
| Cmpd. 5 | 0.003 | 0.21 | 5.32 | 25 |
| Cmpd. 16 | 0.002 | 0.39 | 3.68 | 9.43 |
| Cmpd. 35 | 0.009 | 0.49 | >10 | >20 |
| Cmpd. 36 | 0.013 | 0.61 | >10 | >16 |
| Cmpd. 39 | — | 0.63 | >10 | >16 |
| Cmpd. 42 | — | 1.01 | >10 | >10 |
| Cmpd. 51 | 0.002 | 0.31 | >10 | >20 |

So far, the novel compounds of the invention are unexpectedly endowed with a potent and selective JAK2 inhibitory activity significantly higher than that of the structurally closest prior art compounds and are thus particularly advantageous, in therapy, against cancer, cell proliferative disorders, viral infections, immune disorders, neurodegenerative disorders and cardiovascular diseases.

The invention claimed is:

1. A compound of formula (I):

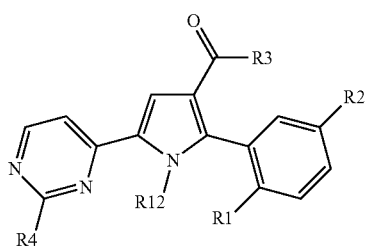

wherein:

R1 is selected from the group consisting of a halogen and a straight or branched $C_1$-$C_6$ alkyl and R2 is selected from the group consisting of a halogen and a substituted $C_1$-$C_6$ alkyl;

R3 is NR8R9 wherein:

R8 and R9 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, arylalkyl, heterocyclyl and heterocyclyl-alkyl, or R8 and R9, taken together with the nitrogen atom to which they are bonded, may form an optionally substituted 5 to 6 membered heteroaryl or heterocyclyl group optionally containing one additional heteroatom selected from N, O and S;

R4 is hydrogen, an optionally substituted straight or branched $C_1$-$C_6$ alkyl or NR10R11, wherein:

R10 and R11 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, arylalkyl, heterocyclyl and heterocyclyl-alkyl, or R10 and R11, taken together with the nitrogen atom to which they are bonded, may form an optionally substituted 5 to 6 membered heteroaryl or heterocyclyl group optionally containing one additional heteroatom selected from N, O and S;

R12 is hydrogen or an optionally substituted straight or branched $C_1$-$C_6$ alkyl;

or a pharmaceutically acceptable salt thereof, with the proviso that the following compounds are excluded:

5-(2-amino-pyrimidin-4-yl)-2-(5-fluoro-2-methyl-phenyl)-1H-pyrrole-3-carboxamide, 5-(2-amino-pyrimidin-4-yl)-2-(2,5-difluoro-phenyl)-1H-pyrrole-3-carboxamide, 5-(2-amino-pyrimidin-4-yl)-2-(5-chloro-2-methyl-phenyl)-1H-pyrrole-3-carboxamide, 5-(2-amino-pyrimidin-4-yl)-2-(5-chloro-2-fluoro-phenyl)-1H-pyrrole-3-carboxamide and 5-(2-amino-pyrimidin-4-yl)-2-(2-chloro-5-fluoro-phenyl)-1H-pyrrole-3-carboxamide.

2. A compound of formula (I) as defined in claim 1 wherein:

R4 is NR10R11, wherein R10 and R11 are independently hydrogen or an optionally substituted straight or branched $C_1$-$C_6$ alkyl.

3. A compound of formula (I) as defined in claim 1 wherein:

R3 is NR8R9, wherein R8 and R9 are independently hydrogen or an optionally substituted straight or branched $C_1$-$C_6$ alkyl.

4. A compound of formula (I) as defined in claim 1 wherein:

R12 is hydrogen.

5. A compound or a pharmaceutically acceptable salt thereof which is selected from the group consisting of:

5-(2-Aminopyrimidin-4-yl)-2-[2-chloro-5-(trifluoromethyl)phenyl]-1H-pyrrole-3-carboxamide, 5-(2-Aminopyrimidin-4-yl)-2-(2,5-dichlorophenyl)-1H-pyrrole-3-carboxamide, 5-(2-Aminopyrimidin-4-yl)-2-(5-chloro-2-methoxyphenyl)-1H-pyrrole-3-carboxamide, 5-(2-Aminopyrimidin-4-yl)-2-(2-chloro-5-ethylphenyl)-1H-pyrrole-3-carboxamide, 5-(2-Aminopyrimidin-4-yl)-2-(5-chloro-2-ethylphenyl)-1H-pyrrole-3-carboxamide, 5-(2-Aminopyrimidin-4-yl)-2-(2-chloro-5-methylphenyl)-1H-pyrrole-3-carboxamide, 5-(2-Aminopyrimidin-4-yl)-2-(2-chloro-5-cyanophenyl)-1H-pyrrole-3-carboxamide, 5-(2-Aminopyrimidin-4-yl)-2-(5-bromo-2-methoxyphenyl)-1H-pyrrole-3-carboxamide, 5-(2-Aminopyrimidin-4-yl)-2-(5-bromo-2-fluorophenyl)-1H-pyrrole-3-carboxamide, 5-(2-Aminopyrimidin-4-yl)-2-[2-chloro-5-(hydroxymethyl)phenyl]-1H-pyrrole-3-carboxamide, 5-(2-Aminopyrimidin-4-yl)-2-(2-chloro-5-methoxyphenyl)-1H-pyrrole-3-carboxamide, 5-(2-Aminopyrimidin-4-yl)-2-[2-chloro-5-(trifluoromethoxy)phenyl]-1H-pyrrole-3-carboxamide,
5-(2-Aminopyrimidin-4-yl)-2-[2-methyl-5-(trifluoromethyl)phenyl]-1H-pyrrole-3-carboxamide,
5-(2-Aminopyrimidin-4-yl)-2-[5-chloro-2-(propan-2-yl)phenyl]-1H-pyrrole-3-carboxamide,
5-(2-Aminopyrimidin-4-yl)-2-[2,5-bis(trifluoromethyl)phenyl]-1H-pyrrole-3-carboxamide,
5-(2-Aminopyrimidin-4-yl)-2-[2-ethyl-5-(trifluoromethyl)phenyl]-1H-pyrrole-3-carboxamide,
5-(2-Aminopyrimidin-4-yl)-2-[5-chloro-2-(trifluoromethyl)phenyl]-1H-pyrrole-3-carboxamide,
5-(2-Aminopyrimidin-4-yl)-2-(5-cyano-2-methylphenyl)-1H-pyrrole-3-carboxamide,
5-(2-Aminopyrimidin-4-yl)-2-(5-chloro-2-methylphenyl)-N-methyl-1H-pyrrole-3-carboxamide,
5-(2-Aminopyrimidin-4-yl)-2-(5-chloro-2-methylphenyl)-N-ethyl-1H-pyrrole-3-carboxamide,
5-(2-Aminopyrimidin-4-yl)-2-(5-chloro-2-methylphenyl)-N-(2-hydroxyethyl)-1H-pyrrole-3-carboxamide,
5-(2-Aminopyrimidin-4-yl)-2-(5-chloro-2-methylphenyl)-N-[2-(piperidin-1-yl)ethyl]-1H-pyrrole-3-carboxamide,
5-(2-Aminopyrimidin-4-yl)-2-(5-chloro-2-methylphenyl)-N-(1-methylpiperidin-4-yl)-1H-pyrrole-3-carboxamide,
5-(2-Aminopyrimidin-4-yl)-2-(5-chloro-2-methylphenyl)-N-phenyl-1H-pyrrole-3-carboxamide,
5-(2-Aminopyrimidin-4-yl)-2-(5-chloro-2-methylphenyl)-N-(furan-2-ylmethyl)-1H-pyrrole-3-carboxamide,
5-(2-Aminopyrimidin-4-yl)-2-(5-chloro-2-methylphenyl)-N-(3-hydroxypropyl)-1H-pyrrole-3-carboxamide,
5-(2-Aminopyrimidin-4-yl)-2-(5-chloro-2-methylphenyl)-N-(2-methoxyethyl)-1H-pyrrole-3-carboxamide,
5-(2-Aminopyrimidin-4-yl)-2-(5-chloro-2-methylphenyl)-N-(2-fluoroethyl)-1H-pyrrole-3-carboxamide,
5-(2-Aminopyrimidin-4-yl)-2-(5-chloro-2-methylphenyl)-N,N-dimethyl-1H-pyrrole-3-carboxamide,
N-(2-Aminoethyl)-5-(2-aminopyrimidin-4-yl)-2-(5-chloro-2-methylphenyl)-1H-pyrrole-3-carboxamide,
5-(2-Aminopyrimidin-4-yl)-2-(5-chloro-2-methylphenyl)-N-[2-(methylamino)ethyl]-1H-pyrrole-3-carboxamide,
5-(2-Aminopyrimidin-4-yl)-N-benzyl-2-(5-chloro-2-methylphenyl)-1H-pyrrole-3-carboxamide,
5-(2-Aminopyrimidin-4-yl)-2-(5-chloro-2-methylphenyl)-N-(2-methylpropyl)-1H-pyrrole-3-carboxamide,
5-(2-Aminopyrimidin-4-yl)-2-(5-chloro-2-methylphenyl)-N-(2,2-dimethylpropyl)-1H-pyrrole-3-carboxamide,
5-(2-Aminopyrimidin-4-yl)-2-(5-chloro-2-ethylphenyl)-N-methyl-1H-pyrrole-3-carboxamide,
5-(2-Aminopyrimidin-4-yl)-2-(5-chloro-2-ethylphenyl)-N-ethyl-1H-pyrrole-3-carboxamide,
5-(2-aminopyrimidin-4-yl)-2-(5-chloro-2-ethylphenyl)-N-(2-hydroxyethyl)-1H-pyrrole-3-carboxamide,
5-(2-Aminopyrimidin-4-yl)-2-(5-chloro-2-ethylphenyl)-N,N-dimethyl-1H-pyrrole-3-carboxamide,
5-(2-Aminopyrimidin-4-yl)-2-[2-chloro-5-(trifluoromethyl)phenyl]-N-methyl-1H-pyrrole-3-carboxamide,
5-(2-Aminopyrimidin-4-yl)-2-(5-chloro-2-hydroxyphenyl)-1H-pyrrole-3-carboxamide,
2-(5-chloro-2-methylphenyl)-5-[2-(methylamino)pyrimidin-4-yl]-1H-pyrrole-3-carboxamide,
5-(Pyrimidin-4-yl)-2-(5-chloro-2-methyl-phenyl)-1H-pyrrole-3-carboxamide,
2-(5-Chloro-2-methylphenyl)-5-(2-methylpyrimidin-4-yl)-1H-pyrrole-3-carboxamide,
5-(2-Aminopyrimidin-4-yl)-2-(5-chloro-2-ethylphenyl)-1-methyl-1H-pyrrole-3-carboxamide,
5-(2-Aminopyrimidin-4-yl)-2-(5-chloro-2-methylphenyl)-1-methyl-1H-pyrrole-3-carboxamide,
5-(2-Aminopyrimidin-4-yl)-2-(5-chloro-2-methylphenyl)-1-ethyl-1H-pyrrole-3-carboxamide,
5-(2-Aminopyrimidin-4-yl)-2-(5-chloro-2-methylphenyl)-1-(2,2,2-trifluoroethyl)-1H-pyrrole-3-carboxamide,
5-(2-Aminopyrimidin-4-yl)-2-(5-chloro-2-methylphenyl)-1-(2-hydroxyethyl)-1H-pyrrole-3-carboxamide,
5-(2-Aminopyrimidin-4-yl)-N-methyl-2-[2-methyl-5-(trifluoromethyl)phenyl]-1H-pyrrole-3-carboxamide and
5-(2-Aminopyrimidin-4-yl)-2-[2-ethyl-5-(trifluoromethyl)phenyl]-N-methyl-1H-pyrrole-3-carboxamide.

6. A process for preparing a compound of formula (I) as defined in claim 1 or the pharmaceutically acceptable salts thereof, characterized in that the process comprises the following steps:

Step 1: metal-catalyzed coupling reaction of a halo derivative of formula (II)

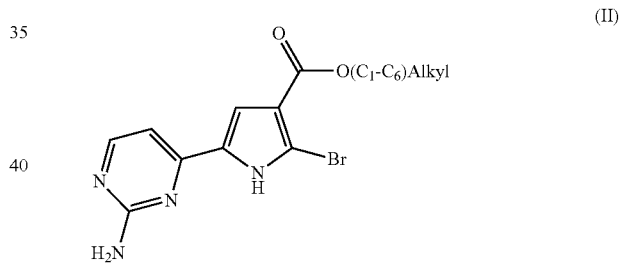

with a substituted aryl boronic acid of formula (IIIa) or an aryl boronic-ester of formula (IIIb):

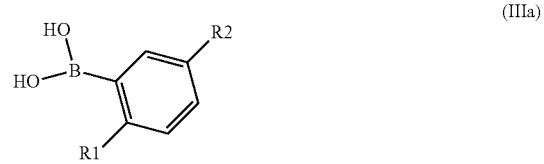

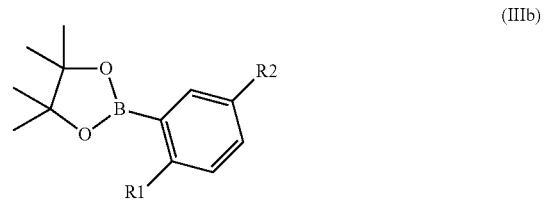

wherein R1 and R2 are as defined in claim 1;

Step 2: hydrolysis of the resulting carboxylic ester of formula (IV)

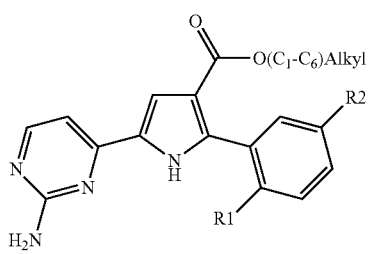

(IV)

wherein R1 and R2 are as defined above, through basic hydrolysis;

Step 3: amidation of the resulting carboxylic acid of formula (V)

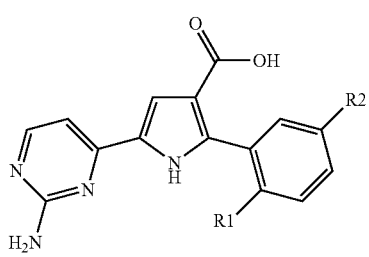

(V)

wherein R1 and R2 are as defined above, through reaction with a derivative of formula (VI) NHR8R9 (VI)

wherein R8 and R9 are as defined in claim 1, to give a compound of formula (I)

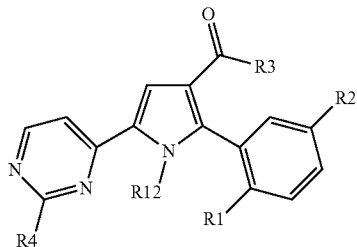

(I)

wherein R1 and R2 are as defined above, R3 is as defined in claim 1, R4 is NH$_2$ and R12 is hydrogen;

or

Step 3a: direct amidation of the carboxylic ester of formula (IV) as defined above through reaction with a derivative of formula (VI) as defined above to give a compound of formula (I)

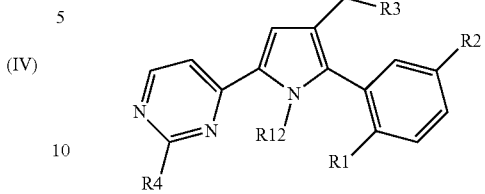

(I)

wherein R1, R2 and R3 are as defined above, R4 is NH$_2$ and R12 is hydrogen;

alternatively,

Step 4: metal-catalyzed coupling reaction of a halo derivative of formula (VII)

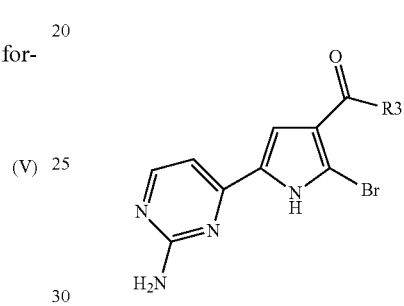

(VII)

wherein R3 is as defined above, with a substituted aryl boronic acid of formula (IIIa) or an aryl boronic-ester of formula (IIIb)

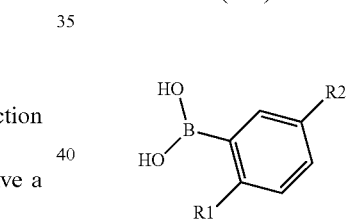

(IIIa)

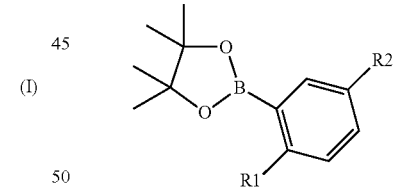

(IIIb)

wherein R1 and R2 are as defined above, to give a compound of formula (I)

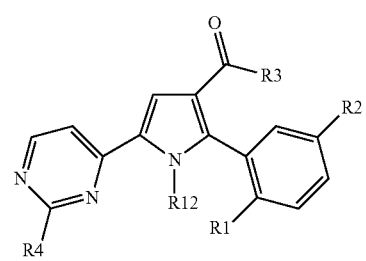

(I)

wherein R1, R2 and R3 are as defined above, R4 is NH$_2$ and R12 is hydrogen;

alternatively

Step 5: reacting a pyrrole of the formula (VIII)

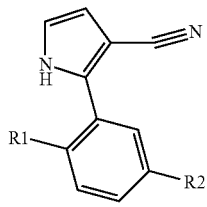
(VIII)

wherein R1 and R2 are as defined above, with acetyl chloride in the presence of a Lewis acid or in the presence of zinc metal;

Step 6: reacting the resultant compound of the formula (IX)

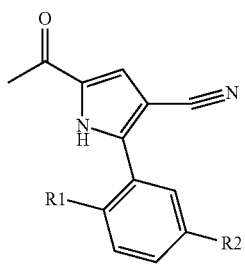
(IX)

wherein R1 and R2 are as defined above, with a dialkyl acetal of N,N-dimethylformamide;

Step 7: reacting the resultant enaminone of the formula (X)

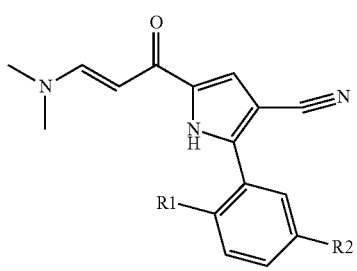
(X)

wherein R1 and R2 are as defined above, with an optionally substituted guanidine of formula (XI) or a salt thereof

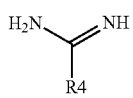
(XI)

wherein R4 is NR10R11, and R10 and R11 are as defined in claim 1;

Step 8: hydrolizing in acidic conditions the cyano group of the resultant compound of the formula (XII)

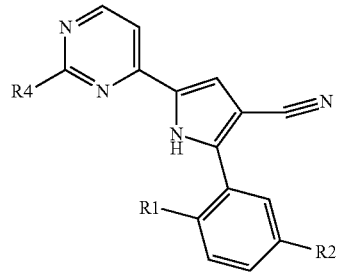
(XII)

wherein R4 is NR10R11, wherein R10 and R11 are as defined in claim 1, and R1 and R2 are as defined above, so as to obtain the compound of the formula (I)

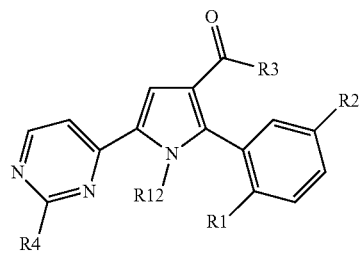
(I)

wherein R1 and R2 are as defined above, R3 is NH$_2$, R4 is NR10R11, wherein R10 and R11 are as defined above, and R12 is hydrogen;

alternatively

Step 9: reacting the enaminone of the formula (X) as defined above, with an optionally substituted amidine of the formula (XIII), or a salt thereof

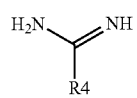
(XIII)

wherein R4 is hydrogen or optionally substituted straight or branched (C$_1$-C$_6$);

Step 10: hydrolizing the cyano group of the resultant compound of the formula (XIV)

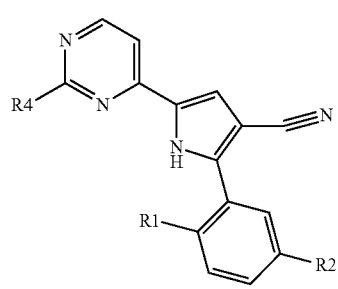
(XIV)

wherein R1 and R2 are as defined above and R4 is hydrogen or optionally substituted straight or branched (C$_1$-C$_6$) alkyl, in acidic conditions, so as to obtain the compound of the formula (I)

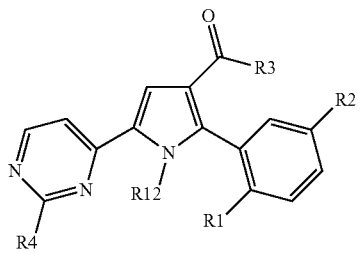

(I)

wherein R1 and R2 as defined above, R3 is —NH$_2$, R4 is hydrogen or optionally substituted straight or branched (C$_1$-C$_6$) alkyl, and R12 is hydrogen;

optionally converting a compound of the formula (I) into another different compound of the formula (I), and, if desired, converting a compound of the formula (I) into a pharmaceutically acceptable salt thereof or converting a salt into the free compound (I).

7. A method for treating a disease caused by and/or associated with a dysregulated protein kinase activity, wherein the disease is selected from the group consisting of cancer, hematopoietic tumors of myeloid lineage, a myeloproliferative disorder, and an immune-related disorder, wherein the cancer is selected from the group consisting of hematopoietic tumors of lymphoid lineage, leukaemia, T and B acute lymphoblastic leukemia (ALL), DS-ALL, B-cell lymphoma, T-cell-lymphoma, Hodgkin's lymphoma, non-Hodgkin's lymphoma, Multiple Myeloma, hairy cell lymphoma, Burkett's lymphoma and mantle cell lymphoma; wherein the hematopoietic tumors of myeloid lineage is selected from the group consisting of, acute and chronic myelogenous leukemias, acute megakaryoblastic leukaemia, myelodysplastic syndrome and promyelocytic leukaemia; wherein the myeloproliferative disorder is selected from the group consisting of, Polycythemia Vera (PV), Essential Thrombocythemia (ET), Primary myelofibrosis and myelofibrosis secondary to PV and ET, chronic myelomonocytic leukemia; and wherein the immune-related disorder is selected from the group consisting of rheumatoid arthritis and psoriasis, the method comprising: administering to a mammal in need thereof an effective amount of a compound of formula (I) as defined in claim 1.

8. The method according to claim 7 further comprising subjecting the mammal in need thereof to a radiation therapy or chemotherapy regimen in combination with at least one cytostatic or cytotoxic agent.

9. The method according to claim 7 wherein the mammal in need thereof is a human.

10. The method according to claim 7 which provides tumor angiogenesis and metastasis inhibition.

11. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

12. A pharmaceutical composition according to claim 11 further comprising one or more chemotherapeutic agents.

13. A product comprising a compound of formula (I) or a pharmaceutically acceptable salt thereof, as defined in claim 1, and one or more chemotherapeutic agents, as a combined preparation for simultaneous, separate or sequential use in anticancer therapy.

14. An intermediate of formula (IIIa):

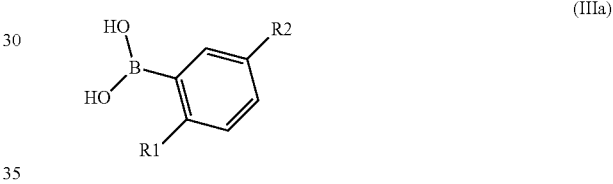

(IIIa)

wherein
R1 is isopropyl and R2 is chlorine.

* * * * *

SEQUENCE LISTING

<160> NUMBER OF SEQ ID NOS: 2

<210> SEQ ID NO 1
<211> LENGTH: 15
<212> TYPE: PRT
<213> ORGANISM: Artificial
<220> FEATURE:
<223> OTHER INFORMATION: peptide substrate -continued

```
<400> SEQUENCE: 1

Leu Pro Leu Asp Lys Asp Tyr Tyr Val Val Arg Glu Pro Gly Gln
1               5                   10                  15

<210> SEQ ID NO 2
<211> LENGTH: 16
<212> TYPE: PRT
<213> ORGANISM: Artificial
<220> FEATURE:
<223> OTHER INFORMATION: Peptide substrate

<400> SEQUENCE: 2

Lys Lys His Thr Asp Asp Gly Tyr Met Pro Met Ser Pro Gly Val Ala
1               5                   10                  15
```